US012773213B2

(12) United States Patent
Nguyen et al.

(10) Patent No.: US 12,773,213 B2
(45) Date of Patent: Oct. 27, 2026

(54) DEVICES, SYSTEMS, AND METHODS FOR TREATING ANEURYSMS

(71) Applicant: Covidien LP, Mansfield, MA (US)

(72) Inventors: Kevin Nguyen, Westminster, CA (US); Junwei Li, Irvine, CA (US); Andyanhdzung Huynh, Westminster, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 19/180,564

(22) Filed: Apr. 16, 2025

(65) Prior Publication Data

US 2025/0241649 A1 Jul. 31, 2025

Related U.S. Application Data

(63) Continuation of application No. 18/313,530, filed on May 8, 2023, now Pat. No. 12,295,582, which is a (Continued)

(51) Int. Cl.
*A61B 17/12* (2006.01)
*A61B 17/00* (2006.01)
(Continued)

(52) U.S. Cl.
CPC .. *A61B 17/12113* (2013.01); *A61B 17/12031* (2013.01); *A61B 17/1214* (2013.01); *A61B 17/12145* (2013.01); *A61B 17/12172* (2013.01); *A61B 17/12186* (2013.01); *A61B 2017/00526* (2013.01); *A61B 2017/00557* (2013.01);
(Continued)

(58) Field of Classification Search
CPC ................ A61B 2017/00526; A61B 17/12172
See application file for complete search history.

(56) References Cited

U.S. PATENT DOCUMENTS 5,041,090 A 8/1991 Scheglov et al.
5,250,071 A 10/1993 Palermo
(Continued)

FOREIGN PATENT DOCUMENTS

CA 3031482 A1 8/2017
CN 101460102 A 6/2009
(Continued)

OTHER PUBLICATIONS

Medtronic ENT. (2021). Discover Novapak: Beyond Structural Stability [Brochure]. Medtronic.
(Continued)

*Primary Examiner* — Jason L Vaughan
(74) *Attorney, Agent, or Firm* — Fortem IP LLP

(57) ABSTRACT

Occlusive devices and associated methods of manufacturing are disclosed herein. Manufacturing an occlusive device can include conforming a mesh to a forming assembly and setting a shape of the mesh based on the forming assembly. In some embodiments, the forming assembly comprises multiple forming members, a mandrel, and/or one or more coupling elements. The method may include everting the mesh over the forming assembly such that the mesh encloses an open volume with a shape based, at least in part, on the shape of the forming assembly. According to some embodiments, setting a shape of the mesh comprises heat-treating the mesh and forming assembly.

20 Claims, 31 Drawing Sheets

Related U.S. Application Data continuation of application No. 16/949,570, filed on Nov. 3, 2020, now Pat. No. 11,679,458.

(60) Provisional application No. 62/930,357, filed on Nov. 4, 2019, provisional application No. 62/930,303, filed on Nov. 4, 2019, provisional application No. 62/930,333, filed on Nov. 4, 2019, provisional application No. 62/930,421, filed on Nov. 4, 2019, provisional application No. 62/930,324, filed on Nov. 4, 2019, provisional application No. 62/930,487, filed on Nov. 4, 2019.

(51) Int. Cl.
*A61B 90/00* (2016.01)
*B23P 19/04* (2006.01)

(52) U.S. Cl.
CPC ............... *A61B 2017/00862* (2013.01); *A61B 2017/00929* (2013.01); *A61B 2017/12054* (2013.01); *A61B 2017/12063* (2013.01); *A61B 17/12168* (2013.01); *A61B 2090/376* (2016.02); *A61B 2090/3966* (2016.02); *B23P 19/047* (2013.01)

(56) References Cited

U.S. PATENT DOCUMENTS 5,261,916 A 11/1993 Engelson
5,284,488 A 2/1994 Sideris
5,326,350 A 7/1994 Li
5,354,295 A 10/1994 Guglielmi et al.
5,405,379 A 4/1995 Lane
5,417,708 A 5/1995 Hall et al.
5,601,600 A 2/1997 Ton
5,645,558 A 7/1997 Horton
5,669,931 A 9/1997 Kupiecki et al.
5,725,552 A 3/1998 Kotula et al.
5,733,294 A 3/1998 Forber et al.
5,741,333 A 4/1998 Frid
5,749,891 A 5/1998 Ken et al.
5,749,894 A 5/1998 Engelson
5,749,895 A 5/1998 Sawyer et al.
5,749,919 A 5/1998 Blanc
5,814,062 A 9/1998 Sepetka et al.
5,823,198 A 10/1998 Jones et al.
5,846,261 A 12/1998 Kotula et al.
5,911,731 A 6/1999 Pham et al.
5,916,235 A 6/1999 Guglielmi
5,925,060 A 7/1999 Forber
5,928,260 A 7/1999 Chin et al.
5,935,148 A 8/1999 Villar et al.
5,941,249 A 8/1999 Maynard
5,944,730 A 8/1999 Nobles et al.
5,944,738 A 8/1999 Amplatz et al.
5,951,599 A 9/1999 Mccrory
5,964,797 A 10/1999 Ho
5,976,169 A 11/1999 Imran
5,980,554 A 11/1999 Lenker et al.
6,022,374 A 2/2000 Imran
6,033,423 A 3/2000 Ken et al.
6,036,720 A 3/2000 Abrams et al.
6,063,070 A 5/2000 Eder
6,063,104 A 5/2000 Villar et al.
6,086,577 A 7/2000 Ken et al.
6,090,125 A 7/2000 Horton
6,093,199 A 7/2000 Brown et al.
6,096,021 A 8/2000 Helm et al.
6,123,715 A 9/2000 Amplatz
6,139,564 A 10/2000 Teoh
6,152,144 A 11/2000 Lesh et al.
6,159,531 A 12/2000 Dang et al.
6,165,193 A 12/2000 Greene et al.
6,168,615 B1 1/2001 Ken et al.
6,168,622 B1 1/2001 Mazzocchi
6,238,403 B1 5/2001 Greene et al.
6,299,619 B1 10/2001 Greene et al.
6,309,367 B1 10/2001 Boock
6,322,576 B1 11/2001 Wallace et al.
6,344,048 B1 2/2002 Chin et al.
6,346,117 B1 2/2002 Greenhalgh
6,350,270 B1 2/2002 Roue
6,368,339 B1 4/2002 Amplatz
6,371,980 B1 4/2002 Rudakov et al.
6,375,668 B1 4/2002 Gifford et al.
6,379,329 B1 4/2002 Naglreiter et al.
6,383,174 B1 5/2002 Eder
6,391,037 B1 5/2002 Greenhalgh
6,428,558 B1 8/2002 Jones et al.
6,447,531 B1 9/2002 Amplatz
6,451,050 B1 9/2002 Rudakov et al.
6,454,780 B1 9/2002 Wallace
6,494,884 B2 12/2002 Gifford et al.
6,506,204 B2 1/2003 Mazzocchi
6,511,468 B1 1/2003 Cragg et al.
6,547,804 B2 4/2003 Porter et al.
6,551,303 B1 4/2003 Van et al.
6,569,179 B2 5/2003 Teoh et al.
6,579,303 B2 6/2003 Amplatz
6,585,748 B1 7/2003 Jeffree
6,589,256 B2 7/2003 Forber
6,589,265 B1 7/2003 Palmer et al.
6,591,472 B1 7/2003 Noone et al.
6,592,605 B2 7/2003 Lenker et al.
6,599,308 B2 7/2003 Amplatz
6,602,261 B2 8/2003 Greene et al.
6,605,101 B1 8/2003 Schaefer et al.
6,605,102 B1 8/2003 Mazzocchi et al.
6,605,111 B2 8/2003 Bose et al.
6,613,074 B1 9/2003 Mitelberg et al.
6,626,939 B1 9/2003 Burnside et al.
6,635,068 B1 10/2003 Dubrul et al.
6,652,555 B1 11/2003 Vantassel et al.
6,652,556 B1 11/2003 Vantassel et al.
6,666,882 B1 12/2003 Bose et al.
6,669,717 B2 12/2003 Marotta et al.
6,669,721 B1 12/2003 Bose et al.
6,682,546 B2 1/2004 Amplatz
6,689,150 B1 2/2004 Vantassel et al.
6,689,486 B2 2/2004 Ho et al.
6,723,112 B2 4/2004 Ho et al.
6,723,116 B2 4/2004 Taheri
6,730,108 B2 5/2004 Van et al.
6,746,468 B1 6/2004 Sepetka et al.
6,746,890 B2 6/2004 Gupta et al.
6,780,196 B2 8/2004 Chin et al.
6,802,851 B2 10/2004 Jones et al.
6,811,560 B2 11/2004 Jones et al.
6,855,153 B2 2/2005 Saadat
6,855,154 B2 2/2005 Abdel-gawwad
6,878,384 B2 4/2005 Cruise et al.
6,905,503 B2 6/2005 Gifford et al.
6,936,055 B1 8/2005 Ken et al.
6,936,058 B2 8/2005 Forde et al.
6,949,113 B2 9/2005 Van et al.
6,953,473 B2 10/2005 Porter
6,989,019 B2 1/2006 Mazzocchi et al.
6,991,617 B2 1/2006 Hektner et al.
6,994,092 B2 2/2006 Van et al.
6,994,717 B2 2/2006 Konya et al.
7,011,671 B2 3/2006 Welch
7,014,645 B2 3/2006 Greene et al.
7,029,487 B2 4/2006 Greene et al.
7,029,949 B2 4/2006 Farnworth et al.
7,070,609 B2 7/2006 West
7,083,632 B2 8/2006 Avellanet et al.
7,098,194 B2 8/2006 Chenite et al.
7,128,073 B1 10/2006 Van et al.
7,128,736 B1 10/2006 Abrams et al.
7,153,323 B1 12/2006 Teoh et al.
7,169,177 B2 1/2007 Obara
7,195,636 B2 3/2007 Avellanet et al.
7,229,461 B2 6/2007 Chin et al.

(56) References Cited

U.S. PATENT DOCUMENTS

| | | | |
|---|---|---|---|
| 7,232,461 | B2 | 6/2007 | Ramer |
| 7,306,622 | B2 | 12/2007 | Jones et al. |
| 7,326,225 | B2 | 2/2008 | Ferrera et al. |
| 7,331,980 | B2 | 2/2008 | Dubrul et al. |
| 7,367,986 | B2 | 5/2008 | Mazzocchi et al. |
| 7,410,482 | B2 | 8/2008 | Murphy et al. |
| 7,419,503 | B2 | 9/2008 | Pulnev et al. |
| 7,473,266 | B2 | 1/2009 | Glaser |
| 7,481,821 | B2 | 1/2009 | Fogarty et al. |
| 7,491,214 | B2 | 2/2009 | Greene et al. |
| 7,569,066 | B2 | 8/2009 | Gerberding et al. |
| 7,572,288 | B2 | 8/2009 | Cox |
| 7,597,704 | B2 | 10/2009 | Frazier et al. |
| 7,601,160 | B2 | 10/2009 | Richter |
| 7,608,088 | B2 | 10/2009 | Jones et al. |
| 7,695,488 | B2 | 4/2010 | Berenstein et al. |
| 7,699,056 | B2 | 4/2010 | Tran et al. |
| 7,708,754 | B2 | 5/2010 | Balgobin et al. |
| 7,727,189 | B2 | 6/2010 | Vantassel et al. |
| 7,744,583 | B2 | 6/2010 | Seifert et al. |
| 7,744,652 | B2 | 6/2010 | Morsi |
| 7,799,767 | B2 | 9/2010 | Lamberti et al. |
| 7,879,065 | B2 | 2/2011 | Gesswein et al. |
| 7,976,527 | B2 | 7/2011 | Cragg et al. |
| RE42,625 | E | 8/2011 | Guglielmi |
| 7,993,364 | B2 | 8/2011 | Morsi |
| RE42,758 | E | 9/2011 | Ken et al. |
| 8,012,210 | B2 | 9/2011 | Lin et al. |
| 8,043,326 | B2 | 10/2011 | Hancock et al. |
| 8,062,379 | B2 | 11/2011 | Morsi |
| 8,075,585 | B2 | 12/2011 | Lee et al. |
| 8,137,293 | B2 | 3/2012 | Zhou et al. |
| 8,142,456 | B2 | 3/2012 | Rosqueta et al. |
| 8,153,612 | B2 | 4/2012 | Ben-shalom et al. |
| 8,202,280 | B2 | 6/2012 | Richter |
| 8,211,160 | B2 | 7/2012 | Garrison et al. |
| 8,221,445 | B2 | 7/2012 | Van et al. |
| 8,333,783 | B2 | 12/2012 | Braun et al. |
| 8,343,167 | B2 | 1/2013 | Henson |
| 8,361,104 | B2 | 1/2013 | Jones et al. |
| 8,361,138 | B2 | 1/2013 | Adams |
| 8,372,062 | B2 | 2/2013 | Murphy et al. |
| 8,398,670 | B2 | 3/2013 | Amplatz et al. |
| 8,425,541 | B2 | 4/2013 | Masters et al. |
| 8,470,013 | B2 | 6/2013 | Duggal et al. |
| 8,530,632 | B2 | 9/2013 | Tijsma et al. |
| 8,597,320 | B2 | 12/2013 | Sepetka et al. |
| 8,603,128 | B2 | 12/2013 | Greene et al. |
| 8,653,319 | B2 | 2/2014 | Amery et al. |
| 8,690,936 | B2 | 4/2014 | Nguyen et al. |
| 8,715,317 | B1 | 5/2014 | Janardhan et al. |
| 8,809,301 | B2 | 8/2014 | Athanasiadis et al. |
| 8,834,515 | B2 | 9/2014 | Win et al. |
| 8,840,867 | B2 | 9/2014 | Sophie et al. |
| 8,906,057 | B2 | 12/2014 | Connor et al. |
| 8,974,512 | B2 | 3/2015 | Aboytes et al. |
| 8,998,947 | B2 | 4/2015 | Aboytes et al. |
| 9,034,348 | B2 | 5/2015 | Ben-shalom et al. |
| 9,192,574 | B2 | 11/2015 | Medina et al. |
| 9,192,692 | B2 | 11/2015 | Medina et al. |
| 9,211,202 | B2 | 12/2015 | Strother et al. |
| 9,301,769 | B2 | 4/2016 | Brady et al. |
| 9,314,248 | B2 | 4/2016 | Molaei |
| 9,333,220 | B2 | 5/2016 | Tijsma et al. |
| 9,339,275 | B2 | 5/2016 | Trommeter et al. |
| 9,433,636 | B2 | 9/2016 | Tijsma et al. |
| 9,486,224 | B2 | 11/2016 | Riina et al. |
| 9,555,120 | B2 | 1/2017 | Andersson |
| 9,629,636 | B2 | 4/2017 | Fogarty et al. |
| 9,655,842 | B1 | 5/2017 | Girdhar et al. |
| 9,681,861 | B2 | 6/2017 | Heisel et al. |
| 9,700,648 | B2 | 7/2017 | Hissong et al. |
| 9,713,475 | B2 | 7/2017 | Divino et al. |
| 9,731,043 | B2 | 8/2017 | Lerouge et al. |
| 9,833,309 | B2 | 12/2017 | Levi et al. |
| 9,844,380 | B2 | 12/2017 | Furey |
| 9,901,543 | B2 | 2/2018 | Chausson et al. |
| 9,907,684 | B2 | 3/2018 | Connor et al. |
| 9,918,718 | B2 | 3/2018 | Lorenzo |
| 9,925,210 | B2 | 3/2018 | Mccarthy et al. |
| 9,962,146 | B2 | 5/2018 | Hebert et al. |
| 10,028,745 | B2 | 7/2018 | Morsi |
| 10,130,372 | B2 | 11/2018 | Griffin |
| 10,517,986 | B2 | 12/2019 | Sherman et al. |
| 10,576,099 | B2 | 3/2020 | Li et al. |
| 10,632,143 | B2 | 4/2020 | Mccarthy et al. |
| 10,932,933 | B2 | 3/2021 | Bardsley et al. |
| 10,952,740 | B2 | 3/2021 | Dasnurkar et al. |
| 11,076,860 | B2 | 8/2021 | Lorenzo |
| 11,134,953 | B2 | 10/2021 | Solaun |
| 11,179,159 | B2 | 11/2021 | Cox et al. |
| 11,389,309 | B2 | 7/2022 | Ruvalcaba et al. |
| 11,504,816 | B2 | 11/2022 | Nguyen et al. |
| 11,679,458 | B2 | 6/2023 | Nguyen et al. |
| 11,685,007 | B2 | 6/2023 | Li et al. |
| 11,690,628 | B2 | 7/2023 | Divino et al. |
| 11,717,924 | B2 | 8/2023 | Nguyen et al. |
| 11,786,253 | B2 | 10/2023 | Divino et al. |
| 11,813,282 | B2 | 11/2023 | Li et al. |
| 11,826,863 | B2 | 11/2023 | Li et al. |
| 12,193,675 | B2 | 1/2025 | Divino et al. |
| 12,251,110 | B2 | 3/2025 | Nguyen et al. |
| 12,256,936 | B2 | 3/2025 | Li et al. |
| 12,295,582 | B2 | 5/2025 | Nguyen et al. |
| 12,569,252 | B2 | 3/2026 | Li et al. |
| 2001/0000797 | A1 | 5/2001 | Mazzocchi |
| 2001/0001835 | A1 | 5/2001 | Greene et al. |
| 2002/0026210 | A1 | 2/2002 | Abdel-gawwad |
| 2002/0042628 | A1 | 4/2002 | Chin et al. |
| 2002/0062145 | A1 | 5/2002 | Rudakov et al. |
| 2002/0119177 | A1 | 8/2002 | Bowman et al. |
| 2002/0147462 | A1 | 10/2002 | Mair et al. |
| 2002/0165572 | A1 | 11/2002 | Saadat |
| 2002/0169473 | A1 | 11/2002 | Sepetka et al. |
| 2002/0193812 | A1 | 12/2002 | Patel et al. |
| 2002/0193813 | A1 | 12/2002 | Helkowski et al. |
| 2003/0004533 | A1 | 1/2003 | Dieck et al. |
| 2003/0004568 | A1 | 1/2003 | Ken et al. |
| 2003/0018294 | A1 | 1/2003 | Cox |
| 2003/0028209 | A1 | 2/2003 | Teoh et al. |
| 2003/0040772 | A1 | 2/2003 | Hyodoh et al. |
| 2003/0055440 | A1 | 3/2003 | Jones et al. |
| 2003/0065303 | A1 | 4/2003 | Wellman et al. |
| 2003/0093097 | A1 | 5/2003 | Avellanet et al. |
| 2003/0093111 | A1 | 5/2003 | Ken et al. |
| 2003/0113478 | A1 | 6/2003 | Dang et al. |
| 2003/0114918 | A1 | 6/2003 | Garrison et al. |
| 2003/0149490 | A1 | 8/2003 | Ashman |
| 2003/0171739 | A1 | 9/2003 | Murphy et al. |
| 2003/0187473 | A1 | 10/2003 | Berenstein et al. |
| 2003/0195553 | A1 | 10/2003 | Wallace et al. |
| 2003/0212419 | A1 | 11/2003 | West |
| 2004/0034386 | A1 | 2/2004 | Fulton et al. |
| 2004/0044361 | A1 | 3/2004 | Frazier et al. |
| 2004/0044391 | A1 | 3/2004 | Porter |
| 2004/0064093 | A1 | 4/2004 | Hektner et al. |
| 2004/0098027 | A1 | 5/2004 | Teoh et al. |
| 2004/0106945 | A1 | 6/2004 | Thramann et al. |
| 2004/0115164 | A1 | 6/2004 | Pierce et al. |
| 2004/0122467 | A1 | 6/2004 | Vantassel et al. |
| 2004/0133222 | A1 | 7/2004 | Tran et al. |
| 2004/0138758 | A1 | 7/2004 | Kronengold et al. |
| 2004/0161451 | A1 | 8/2004 | Pierce et al. |
| 2004/0167597 | A1 | 8/2004 | Costantino et al. |
| 2004/0176798 | A1 | 9/2004 | Foy et al. |
| 2004/0181253 | A1 | 9/2004 | Sepetka et al. |
| 2004/0236344 | A1 | 11/2004 | Monstadt et al. |
| 2005/0021077 | A1 | 1/2005 | Chin et al. |
| 2005/0038470 | A1 | 2/2005 | Van et al. |
| 2005/0049625 | A1 | 3/2005 | Shaya et al. |
| 2005/0089554 | A1 | 4/2005 | Cormier et al. |
| 2005/0119684 | A1 | 6/2005 | Guterman et al. |
| 2005/0131443 | A1 | 6/2005 | Abdel-gawwad |
| 2005/0222580 | A1 | 10/2005 | Gifford et al. |

(56) References Cited

U.S. PATENT DOCUMENTS

| | | | |
|---|---|---|---|
| 2005/0267510 | A1 | 12/2005 | Razack |
| 2005/0267511 | A1 | 12/2005 | Marks et al. |
| 2005/0267527 | A1 | 12/2005 | Sandoval et al. |
| 2005/0277978 | A1 | 12/2005 | Greenhalgh |
| 2005/0278023 | A1 | 12/2005 | Zwirkoski |
| 2006/0028209 | A1 | 2/2006 | Walker |
| 2006/0034883 | A1 | 2/2006 | Dang et al. |
| 2006/0052816 | A1 | 3/2006 | Bates et al. |
| 2006/0064151 | A1 | 3/2006 | Guterman et al. |
| 2006/0106421 | A1 | 5/2006 | Teoh |
| 2006/0116709 | A1 | 6/2006 | Sepetka et al. |
| 2006/0116712 | A1 | 6/2006 | Sepetka et al. |
| 2006/0116713 | A1 | 6/2006 | Sepetka et al. |
| 2006/0116714 | A1 | 6/2006 | Sepetka et al. |
| 2006/0122548 | A1 | 6/2006 | Abrams |
| 2006/0155323 | A1 | 7/2006 | Porter et al. |
| 2006/0190070 | A1 | 8/2006 | Dieck et al. |
| 2006/0200234 | A1 | 9/2006 | Hines |
| 2006/0206140 | A1 | 9/2006 | Shaolian et al. |
| 2006/0206198 | A1 | 9/2006 | Churchwell et al. |
| 2006/0206199 | A1 | 9/2006 | Churchwell et al. |
| 2006/0241686 | A1 | 10/2006 | Ferrera et al. |
| 2006/0247680 | A1 | 11/2006 | Amplatz et al. |
| 2006/0271162 | A1 | 11/2006 | Vito et al. |
| 2006/0276824 | A1 | 12/2006 | Mitelberg et al. |
| 2006/0276829 | A1 | 12/2006 | Balgobin et al. |
| 2006/0276830 | A1 | 12/2006 | Balgobin et al. |
| 2007/0003594 | A1 | 1/2007 | Brady et al. |
| 2007/0010850 | A1 | 1/2007 | Balgobin et al. |
| 2007/0014831 | A1 | 1/2007 | Sung et al. |
| 2007/0083226 | A1 | 4/2007 | Buiser et al. |
| 2007/0100426 | A1 | 5/2007 | Rudakov et al. |
| 2007/0135907 | A1 | 6/2007 | Wilson et al. |
| 2007/0167876 | A1 | 7/2007 | Euteneuer et al. |
| 2007/0167877 | A1 | 7/2007 | Euteneuer et al. |
| 2007/0167972 | A1 | 7/2007 | Euteneuer et al. |
| 2007/0175536 | A1 | 8/2007 | Monetti et al. |
| 2007/0179507 | A1 | 8/2007 | Shah |
| 2007/0179520 | A1 | 8/2007 | West |
| 2007/0185442 | A1 | 8/2007 | Euteneuer et al. |
| 2007/0185443 | A1 | 8/2007 | Euteneuer et al. |
| 2007/0185444 | A1 | 8/2007 | Euteneuer et al. |
| 2007/0185457 | A1 | 8/2007 | Euteneuer et al. |
| 2007/0186933 | A1 | 8/2007 | Domingo et al. |
| 2007/0191924 | A1 | 8/2007 | Rudakov |
| 2007/0198059 | A1 | 8/2007 | Patel et al. |
| 2007/0198075 | A1 | 8/2007 | Levy |
| 2007/0219619 | A1 | 9/2007 | Dieck et al. |
| 2007/0221230 | A1 | 9/2007 | Thompson et al. |
| 2007/0265656 | A1 | 11/2007 | Amplatz et al. |
| 2007/0270902 | A1 | 11/2007 | Slazas et al. |
| 2007/0276426 | A1 | 11/2007 | Euteneuer |
| 2007/0276427 | A1 | 11/2007 | Euteneuer |
| 2007/0282373 | A1 | 12/2007 | Ashby et al. |
| 2007/0288083 | A1 | 12/2007 | Hines |
| 2007/0299461 | A1 | 12/2007 | Elliott |
| 2008/0033366 | A1 | 2/2008 | Matson et al. |
| 2008/0065145 | A1 | 3/2008 | Carpenter |
| 2008/0069801 | A1 | 3/2008 | Lee et al. |
| 2008/0081763 | A1 | 4/2008 | Swetlin et al. |
| 2008/0082176 | A1 | 4/2008 | Slazas |
| 2008/0086196 | A1 | 4/2008 | Truckai et al. |
| 2008/0109057 | A1 | 5/2008 | Calabria et al. |
| 2008/0114391 | A1 | 5/2008 | Dieck et al. |
| 2008/0114436 | A1 | 5/2008 | Dieck et al. |
| 2008/0119886 | A1 | 5/2008 | Greenhalgh et al. |
| 2008/0125852 | A1 | 5/2008 | Garrison et al. |
| 2008/0132820 | A1 | 6/2008 | Buckman et al. |
| 2008/0140177 | A1 | 6/2008 | Hines |
| 2008/0195137 | A1 | 8/2008 | Alleyne et al. |
| 2008/0200945 | A1 | 8/2008 | Amplatz et al. |
| 2008/0200979 | A1 | 8/2008 | Dieck et al. |
| 2008/0221554 | A1 | 9/2008 | Oconnor et al. |
| 2008/0221600 | A1 | 9/2008 | Dieck et al. |
| 2008/0221703 | A1 | 9/2008 | Que et al. |
| 2008/0281350 | A1 | 11/2008 | Sepetka et al. |
| 2008/0283066 | A1 | 11/2008 | Delgado et al. |
| 2009/0018637 | A1 | 1/2009 | Paul et al. |
| 2009/0024224 | A1 | 1/2009 | Chen et al. |
| 2009/0025820 | A1 | 1/2009 | Adams |
| 2009/0036877 | A1 | 2/2009 | Nardone et al. |
| 2009/0043375 | A1 | 2/2009 | Rudakov et al. |
| 2009/0056722 | A1 | 3/2009 | Swann |
| 2009/0062899 | A1 | 3/2009 | Dang et al. |
| 2009/0076540 | A1 | 3/2009 | Marks et al. |
| 2009/0099592 | A1 | 4/2009 | Buiser et al. |
| 2009/0112249 | A1 | 4/2009 | Miles et al. |
| 2009/0112251 | A1 | 4/2009 | Qian et al. |
| 2009/0125119 | A1 | 5/2009 | Obermiller et al. |
| 2009/0148492 | A1 | 6/2009 | Dave et al. |
| 2009/0155367 | A1 | 6/2009 | Neuwirth et al. |
| 2009/0187214 | A1 | 7/2009 | Amplatz et al. |
| 2009/0264978 | A1 | 10/2009 | Dieck et al. |
| 2009/0270974 | A1 | 10/2009 | Berez et al. |
| 2009/0275974 | A1 | 11/2009 | Marchand et al. |
| 2009/0287291 | A1 | 11/2009 | Becking et al. |
| 2009/0287292 | A1 | 11/2009 | Becking et al. |
| 2009/0287294 | A1 | 11/2009 | Rosqueta et al. |
| 2009/0287297 | A1 | 11/2009 | Cox |
| 2009/0297582 | A1 | 12/2009 | Meyer et al. |
| 2009/0306702 | A1 | 12/2009 | Miloslavski et al. |
| 2009/0306706 | A1 | 12/2009 | Osypka |
| 2009/0318892 | A1 | 12/2009 | Aboytes et al. |
| 2009/0318941 | A1 | 12/2009 | Sepetka et al. |
| 2009/0319023 | A1 | 12/2009 | Hildebrand et al. |
| 2010/0021545 | A1 | 1/2010 | Chaput et al. |
| 2010/0023046 | A1 | 1/2010 | Heidner et al. |
| 2010/0023048 | A1 | 1/2010 | Mach |
| 2010/0030200 | A1 | 2/2010 | Strauss et al. |
| 2010/0036410 | A1 | 2/2010 | Krolik et al. |
| 2010/0106178 | A1 | 4/2010 | Obermiller et al. |
| 2010/0121350 | A1 | 5/2010 | Mirigian |
| 2010/0131002 | A1 | 5/2010 | Connor et al. |
| 2010/0139465 | A1 | 6/2010 | Christian et al. |
| 2010/0144895 | A1 | 6/2010 | Porter |
| 2010/0160949 | A1 | 6/2010 | Takuma |
| 2010/0174269 | A1 | 7/2010 | Tompkins et al. |
| 2010/0184720 | A1 | 7/2010 | Gavard et al. |
| 2010/0185271 | A1 | 7/2010 | Zhang |
| 2010/0228184 | A1 | 9/2010 | Mavani et al. |
| 2010/0249830 | A1 | 9/2010 | Nelson |
| 2010/0256527 | A1 | 10/2010 | Lippert et al. |
| 2010/0256528 | A1 | 10/2010 | Lippert et al. |
| 2010/0256601 | A1 | 10/2010 | Lippert et al. |
| 2010/0256602 | A1 | 10/2010 | Lippert et al. |
| 2010/0256603 | A1 | 10/2010 | Lippert et al. |
| 2010/0256604 | A1 | 10/2010 | Lippert et al. |
| 2010/0256605 | A1 | 10/2010 | Lippert et al. |
| 2010/0256606 | A1 | 10/2010 | Lippert et al. |
| 2010/0262014 | A1 | 10/2010 | Huang |
| 2010/0268201 | A1 | 10/2010 | Tieu et al. |
| 2010/0274276 | A1 | 10/2010 | Chow et al. |
| 2010/0298791 | A1 | 11/2010 | Jones et al. |
| 2010/0312061 | A1 | 12/2010 | Hess et al. |
| 2011/0022149 | A1 | 1/2011 | Cox et al. |
| 2011/0046658 | A1 | 2/2011 | Connor et al. |
| 2011/0077620 | A1 | 3/2011 | Debeer |
| 2011/0125110 | A1 | 5/2011 | Cotton |
| 2011/0137332 | A1 | 6/2011 | Sepetka et al. |
| 2011/0137405 | A1 | 6/2011 | Wilson et al. |
| 2011/0144669 | A1 | 6/2011 | Becking et al. |
| 2011/0152993 | A1 | 6/2011 | Marchand et al. |
| 2011/0166588 | A1 | 7/2011 | Connor et al. |
| 2011/0196415 | A1 | 8/2011 | Ujiie et al. |
| 2011/0202085 | A1 | 8/2011 | Loganathan et al. |
| 2011/0208227 | A1 | 8/2011 | Becking |
| 2011/0224776 | A1 | 9/2011 | Sepetka et al. |
| 2011/0238041 | A1 | 9/2011 | Lim et al. |
| 2011/0245862 | A1 | 10/2011 | Dieck et al. |
| 2011/0251699 | A1 | 10/2011 | Ladet |
| 2011/0265943 | A1 | 11/2011 | Rosqueta et al. |
| 2011/0319926 | A1 | 12/2011 | Becking et al. |
| 2012/0010644 | A1 | 1/2012 | Sideris et al. |
| 2012/0022572 | A1 | 1/2012 | Braun et al. |

(56) References Cited

U.S. PATENT DOCUMENTS

2012/0041472 A1 2/2012 Tan et al.
2012/0101510 A1 4/2012 Lenker et al.
2012/0116350 A1 5/2012 Strauss et al.
2012/0123510 A1 5/2012 Liungman
2012/0143237 A1 6/2012 Cam et al.
2012/0143243 A1 6/2012 Hill et al.
2012/0143301 A1 6/2012 Maslanka et al.
2012/0165919 A1 6/2012 Cox et al.
2012/0197283 A1 8/2012 Marchand et al.
2012/0239074 A1 9/2012 Aboytes et al.
2012/0271344 A1 10/2012 Ford et al.
2012/0283768 A1 11/2012 Cox et al.
2012/0283769 A1 11/2012 Cruise et al.
2012/0310269 A1 12/2012 Fearnot et al.
2012/0316598 A1 12/2012 Becking et al.
2012/0316632 A1 12/2012 Gao
2012/0323271 A1 12/2012 Obermiller et al.
2012/0330341 A1 12/2012 Becking et al.
2012/0330347 A1 12/2012 Becking et al.
2012/0330348 A1 12/2012 Strauss et al.
2013/0066357 A1 3/2013 Aboytes et al.
2013/0066360 A1 3/2013 Becking et al.
2013/0073026 A1 3/2013 Russo et al.
2013/0085522 A1 4/2013 Becking et al.
2013/0116722 A1 5/2013 Aboytes et al.
2013/0138136 A1 5/2013 Beckham et al.
2013/0211495 A1 8/2013 Halden et al.
2013/0244972 A1 9/2013 Ben-shalom et al.
2013/0274866 A1 10/2013 Cox et al.
2013/0296912 A1 11/2013 Ottma
2014/0012307 A1 1/2014 Franano et al.
2014/0017210 A1 1/2014 Laurencin et al.
2014/0039542 A1 2/2014 Trommeter et al.
2014/0058420 A1 2/2014 Hannes et al.
2014/0135810 A1 5/2014 Divino et al.
2014/0135811 A1 5/2014 Divino et al.
2014/0135812 A1 5/2014 Divino et al.
2014/0200607 A1 7/2014 Sepetka et al.
2014/0215792 A1 8/2014 Leopold et al.
2014/0257360 A1 9/2014 Keillor
2014/0257361 A1 9/2014 Prom
2014/0257374 A1 9/2014 Heisel et al.
2014/0316012 A1 10/2014 Freyman et al.
2014/0371734 A1 12/2014 Truckai
2014/0377187 A1 12/2014 Lerouge et al.
2015/0005808 A1 1/2015 Chouinard et al.
2015/0133989 A1 5/2015 Lubock et al.
2015/0216684 A1 8/2015 Enzmann et al.
2015/0250628 A1 9/2015 Monstadt et al.
2015/0272589 A1 10/2015 Lorenzo
2015/0272590 A1 10/2015 Aboytes et al.
2015/0313605 A1 11/2015 Griffin
2015/0313737 A1 11/2015 Tippett et al.
2015/0327843 A1 11/2015 Garrison
2015/0335333 A1 11/2015 Jones et al.
2015/0342613 A1 12/2015 Aboytes et al.
2015/0343181 A1 12/2015 Bradway et al.
2016/0022445 A1 1/2016 Ruvalcaba et al.
2016/0030050 A1 2/2016 Franano et al.
2016/0066921 A1 3/2016 Seifert et al.
2016/0082037 A1 3/2016 Kirsch et al.
2016/0106437 A1 4/2016 Van Der Burg et al.
2016/0128699 A1 5/2016 Hadley et al.
2016/0135984 A1 5/2016 Rudakov et al.
2016/0206320 A1 7/2016 Connor
2016/0206321 A1 7/2016 Connor
2016/0249935 A1 9/2016 Hewitt et al.
2016/0256170 A1 9/2016 Busold et al.
2016/0296714 A1 10/2016 Mide et al.
2016/0331381 A1 11/2016 Ma
2017/0105739 A1 4/2017 Dias et al.
2017/0150971 A1 6/2017 Hines
2017/0156734 A1 6/2017 Griffin
2017/0156903 A1 6/2017 Shobayashi
2017/0189035 A1 7/2017 Porter
2017/0224350 A1 8/2017 Shimizu et al.
2017/0224355 A1 8/2017 Bowman et al.
2017/0266023 A1 9/2017 Thomas
2017/0296466 A1 10/2017 Girdhar et al.
2017/0312364 A1 11/2017 Bossy et al.
2017/0340333 A1 11/2017 Badruddin et al.
2017/0354419 A1 12/2017 Teoh et al.
2017/0354421 A1 12/2017 Maguire et al.
2017/0367707 A1 12/2017 Divino
2017/0367708 A1 12/2017 Mayer et al.
2017/0367713 A1 12/2017 Greene et al.
2018/0049859 A1 2/2018 Stoppenhagen et al.
2018/0070955 A1 3/2018 Greene et al.
2018/0110797 A1 4/2018 Li et al.
2018/0125686 A1 5/2018 Lu
2018/0132856 A1 5/2018 Wierzbicki et al.
2018/0140305 A1 5/2018 Connor
2018/0161185 A1 6/2018 Kresslein et al.
2018/0193025 A1 7/2018 Walzman
2018/0193026 A1 7/2018 Yang et al.
2018/0206849 A1 7/2018 Hewitt et al.
2018/0206852 A1 7/2018 Moeller
2018/0242979 A1 8/2018 Lorenzo
2018/0256171 A1 9/2018 Chow et al.
2018/0317932 A1 11/2018 H'doubler
2019/0008522 A1 1/2019 Lorenzo
2019/0009057 A1 1/2019 Li et al.
2019/0053807 A1 2/2019 Tassoni et al.
2019/0053811 A1 2/2019 Garza et al.
2019/0192167 A1 6/2019 Lorenzo
2019/0223876 A1 7/2019 Badruddin et al.
2019/0223881 A1 7/2019 Hewitt et al.
2019/0282242 A1 9/2019 Divino et al.
2019/0336132 A1 11/2019 Warner et al.
2019/0343532 A1 11/2019 Divino et al.
2019/0351107 A1 11/2019 Sawhney et al.
2020/0060965 A1 2/2020 Supper
2020/0061099 A1 2/2020 Li et al.
2020/0113576 A1 4/2020 Gorochow et al.
2020/0138448 A1 5/2020 Dasnurkar et al.
2020/0268392 A1 8/2020 Choi et al.
2020/0315644 A1 10/2020 Bowman
2020/0360419 A1 11/2020 Mccarthy et al.
2021/0022743 A1 1/2021 Delaney et al.
2021/0128160 A1 5/2021 Li et al.
2021/0128161 A1 5/2021 Nageswaran et al.
2021/0128162 A1 5/2021 Rhee et al.
2021/0128165 A1 5/2021 Pulugurtha et al.
2021/0128167 A1 5/2021 Patel et al.
2021/0128168 A1 5/2021 Nguyen et al.
2021/0128169 A1 5/2021 Li et al.
2021/0129275 A1 5/2021 Nguyen et al.
2021/0137530 A1 5/2021 Greene et al.
2021/0153872 A1 5/2021 Nguyen et al.
2021/0161643 A1 6/2021 Totten et al.
2021/0196284 A1 7/2021 Gorochow et al.
2021/0212698 A1 7/2021 Connor
2022/0008082 A1 1/2022 Connor
2022/0296788 A1 9/2022 Hussain et al.
2022/0304696 A2 9/2022 Rhee et al.
2023/0023511 A1 1/2023 Nguyen et al.
2023/0294223 A1 9/2023 Li et al.
2023/0301660 A1 9/2023 Sonmez et al.
2023/0311254 A1 10/2023 Nguyen et al.
2023/0355243 A1 11/2023 Zaidat et al.
2023/0373040 A1 11/2023 Nguyen et al.
2024/0033281 A1 2/2024 Li et al.
2024/0050099 A1 2/2024 Pecor et al.
2024/0075565 A1 3/2024 Li et al.
2025/0169824 A1 5/2025 Li et al.
2025/0195077 A1 6/2025 Nguyen et al.
2026/0182992 A1 7/2026 Li et al.

FOREIGN PATENT DOCUMENTS

CN 102083493 A 6/2011
CN 102202585 A 9/2011
CN 202313544 U 7/2012
CN 102740799 A 10/2012

(56) References Cited

FOREIGN PATENT DOCUMENTS

| | | | |
|---|---|---|---|
| CN | 105105812 | A | 12/2015 |
| CN | 105209075 | A | 12/2015 |
| DE | 102011102933 | A1 | 12/2012 |
| EP | 0717969 | A2 | 6/1996 |
| EP | 1188414 | A1 | 3/2002 |
| EP | 1813213 | A2 | 8/2007 |
| EP | 2208483 | A1 | 7/2010 |
| EP | 1448607 | B1 | 1/2011 |
| EP | 2566454 | B1 | 3/2014 |
| EP | 2468348 | B1 | 10/2016 |
| EP | 2121026 | B1 | 6/2017 |
| JP | 2005261951 | A | 9/2005 |
| JP | 2008521492 | A | 6/2008 |
| WO | 9406502 | A2 | 3/1994 |
| WO | 9905977 | A1 | 2/1999 |
| WO | 03011151 | A1 | 2/2003 |
| WO | 2006034149 | A2 | 3/2006 |
| WO | 2007006139 | A1 | 1/2007 |
| WO | 2007079402 | A2 | 7/2007 |
| WO | 2007121405 | A2 | 10/2007 |
| WO | 2008074027 | A1 | 6/2008 |
| WO | 2009014528 | A1 | 1/2009 |
| WO | 2009134337 | A1 | 11/2009 |
| WO | 2010009019 | A1 | 1/2010 |
| WO | 2010027363 | A1 | 3/2010 |
| WO | 2010028300 | A1 | 3/2010 |
| WO | 2010077599 | A1 | 7/2010 |
| WO | 2011066962 | A1 | 6/2011 |
| WO | 2011095966 | A1 | 8/2011 |
| WO | 2012034135 | A1 | 3/2012 |
| WO | 2013112944 | A1 | 8/2013 |
| WO | 2013138615 | A2 | 9/2013 |
| WO | 2013138615 | A3 | 9/2014 |
| WO | 2014169708 | A1 | 10/2014 |
| WO | 2015160721 | A1 | 10/2015 |
| WO | 2015166013 | A1 | 11/2015 |
| WO | 2016098057 | A1 | 6/2016 |
| WO | 2017074411 | A1 | 5/2017 |
| WO | 2018050262 | A1 | 3/2018 |
| WO | 2018051187 | A1 | 3/2018 |
| WO | 2019038293 | A1 | 2/2019 |
| WO | 2020162764 | A1 | 8/2020 |
| WO | 2020236917 | A1 | 11/2020 |
| WO | 2020262817 | A1 | 12/2020 |
| WO | 2021046389 | A1 | 3/2021 |

OTHER PUBLICATIONS

Ashland, "Formulating Elegant Liquid and Semisolid Drug Products," Natrosol 250, Hydroxyethylcellulose (HEC), (2018) pp. 1-32 (Year: 2018).

Barnett, et al., "Assessment of EmboGel—A Selectively Dissolvable Radiopaque Hydrogel for Embolic Applications", J Vasc Interv Radiol 2011; vol. 22, No. 2, Feb. 2011, pp. 203-211.

Berenstein, et al., "Treatment of Experimental Aneurysms With an Embolic-Containing Device and Liquid Embolic Agent: Feasibility and Angiographic and Histological Results" Neurosurgery, vol. 64, No. 2, Feb. 2009, pp. 367-373.

Brennecka, et al., "In vivo embolization of lateral wall aneurysms in canines using the liquid-to-solid gelling PPODA-QT polymer system: 6-month pilot study", Laboratory investigation, J Neurosurg, vol. 119,, Jul. 2013, pp. 228-238.

Coutu, et al., "A new radiopaque embolizing agent for the treatment of endoleaks after endovascular repair: Influence of contrast agent on chitosan thermogel properties", Journal of Biomedical Materials Research Part B: Applied Biomaterials, 101B(1), 153-161. https://doi.org/10.1002/jbm.b.32828.

Fawal, Gomaaf. , "Hydroxyethyl Cellulose Hydrogel for Wound Dressing: Fabrication Characterization and in Vitro Evaluation,", International Journal of Biological Macromolecules 111 (2018); pp. 649-659 (Year: 2018).

Jalani, et al., "Tough, In-Situ Thermogelling, Injectable Hydrogels for Biomedical Applications", Macromolecular Bioscience, 2014, 8 Pages.

Murayama, et al., "Endovascular Treatment of Experimental Aneurysms by Use of a Combination of Liquid Embolic Agents and Protective Devices", Experimental Aneurysms, AJNR Am J Neuroradiol, vol. 21, Oct. 2000, pp. 1726-1735.

Naderi-Meshkin, et al., "Chitosan-Based Injectable Hydrogel as a Promising in Situ Forming Scaffold for Cartilage Tissue Engineering,", Cell Biol Int 38 (2014) pp. 72-84 (Year: 2014).

Ning, et al., "Experimental study of temperature-sensitive chitosan/β-glycerophosphate embolic material in embolizing the basicranial rete mirabile in swines", Experimental and Therapeutic Medicine, vol. 10, Feb. 19, 2015. pp. 316-322.

Shive, et al., "BST-Cargel® treatment maintains cartilage repair superiority over microfracture at 5 years in a multicenter randomized controlled trial.", Cartilage, 6(2), 62-72. https://doi.org/10.1177/1947603514562064.

Supper, et al., "Chitosan/glucose 1-phosphate as new stable in situ forming depot system for controlled drug delivery", European Journal of Pharmaceutics and Biopharmaceutics, 88(2), 361-373. https://doi.org/10.1016/j.ejpb.2014.05.015.

Supper, et al., "Rheological Study of Chitosan/Polyol-phosphate Systems: Influence of the Polyol Part on the Thermo-Induced Gelation Mechanism", Langmuir, 29(32), 10229-10237. https://doi.org/10.1021/la401993q.

Wang, et al., "In Vivo Assessment of Chitosan/β-Glycerophosphate as a New Liquid Embolic Agent", Interventional Neuroradiology, vol. 17, 2011, pp. 87-92.

Zhen, et al., "Embolization of aneurysm by chitosan-glycerophosphate-fibroblast tissue hydrogel, a tissue engineering material: experiment with rabbits", Natl Med J China, vol. 89, No. 11, Mar. 24, 2009, pp. 727-731.

International Search Report and Written Opinion mailed Feb. 17, 2021, International Application No. PCT/US20/70741, 6 pages.

International Search Report and Written Opinion mailed Feb. 23, 2021, International Application No. PCT/US20/70743, 14 pages.

International Search Report and Written Opinion mailed Aug. 9, 2022; International Application No. PCT/US2022/071166; 10 pages.

International Search Report and Written Opinion mailed Apr. 13, 2021, International Application No. PCT/US20/70742,18 pages.

DEVICES, SYSTEMS, AND METHODS FOR TREATING ANEURYSMS

CROSS-REFERENCE TO RELATED APPLICATION(S)

The present application is a continuation of U.S. patent application Ser. No. 18/313,530, filed May 8, 2023, which is a continuation of U.S. patent application Ser. No. 16/949,570, filed Nov. 3, 2020, now issued as U.S. Pat. No. 11,679,458, which claims the benefit of priority of U.S. Provisional Application No. 62/930,421, filed Nov. 4, 2019, U.S. Provisional Application No. 62/930,487, filed Nov. 4, 2019, U.S. Provisional Application No. 62/930,303, filed Nov. 4, 2019, U.S. Provisional Application No. 62/930,324, filed Nov. 4, 2019, U.S. Provisional Application No. 62/930,333, filed Nov. 4, 2019, and U.S. Provisional Application No. 62/930,357, filed Nov. 4, 2019, each of which is incorporated by reference herein in its entirety.

The following applications are also incorporated by reference herein in their entireties: U.S. patent application Ser. No. 16/949,567, filed Nov. 3, 2020, and titled DEVICES, SYSTEMS, AND METHODS FOR TREATMENT OF INTRACRANIAL ANEURYSMS; U.S. patent application Ser. No. 16/949,568, filed Nov. 3, 2020, and titled DEVICES, SYSTEMS, AND METHODS FOR TREATMENT OF INTRACRANIAL ANEURYSMS; U.S. patent application Ser. No. 16/949,561, filed Nov. 3, 2020, and titled SYSTEMS AND METHODS FOR TREATING ANEURYSMS; U.S. patent application Ser. No. 16/949,563, filed Nov. 3, 2020, and titled SYSTEMS AND METHODS FOR TREATING ANEURYSMS; U.S. patent application Ser. No. 16/949,564, filed Nov. 3, 2020, and titled SYSTEMS AND METHODS FOR TREATING ANEURYSMS; U.S. patent application Ser. No. 16/949,565, filed Nov. 3, 2020, and titled ANEURYSM TREATMENT DEVICE; U.S. patent application Ser. No. 16/949,569, filed Nov. 3, 2020, and titled DEVICES, SYSTEMS, AND METHODS FOR TREATMENT OF INTRACRANIAL ANEURYSMS; U.S. patent application Ser. No. 16/949,566, filed Nov. 3, 2020, and titled SYSTEMS AND METHODS FOR TREATING ANEURYSMS; International Application No. PCT/US2020/070743, filed Nov. 3, 2020, titled DEVICES, SYSTEMS, AND METHODS FOR TREATMENT OF INTRACRANIAL ANEURYSMS; International Application No. PCT/US2020/070741, filed Nov. 3, 2020, titled DEVICES, SYSTEMS, AND METHODS FOR TREATMENT OF INTRACRANIAL ANEURYSMS; and International Application No. PCT/US2020/070742, filed Nov. 3, 2020, titled SYSTEMS AND METHODS FOR TREATING ANEURYSMS.

TECHNICAL FIELD

The present technology relates to occlusive devices and associated methods of manufacturing.

BACKGROUND

An intracranial aneurysm is a portion of an intracranial blood vessel that bulges outward from the blood vessel's main channel. This condition often occurs at a portion of a blood vessel that is abnormally weak because of a congenital anomaly, trauma, high blood pressure, or for another reason. Once an intracranial aneurysm forms, there is a significant risk that the aneurysm will eventually rupture and cause a medical emergency with a high risk of mortality due to hemorrhaging. When an unruptured intracranial aneurysm is detected or when a patient survives an initial rupture of an intracranial aneurysm, vascular surgery is often indicated. One conventional type of vascular surgery for treating an intracranial aneurysm includes using a microcatheter to dispose a platinum coil within an interior volume of the aneurysm. Over time, the presence of the coil should induce formation of a thrombus. Ideally, the aneurysm's neck closes at the site of the thrombus and is replaced with new endothelial tissue. Blood then bypasses the aneurysm, thereby reducing the risk of aneurysm rupture (or re-rupture) and associated hemorrhaging. Unfortunately, long-term recanalization (i.e., restoration of blood flow to the interior volume of the aneurysm) after this type of vascular surgery occurs in a number of cases, especially for intracranial aneurysms with relatively wide necks and/or relatively large interior volumes.

Another conventional type of vascular surgery for treating an intracranial aneurysm includes deploying a flow diverter within the associated intracranial blood vessel. The flow diverter is often a mesh tube that causes blood to preferentially flow along a main channel of the blood vessel while blood within the aneurysm stagnates. The stagnant blood within the aneurysm should eventually form a thrombus that leads to closure of the aneurysm's neck and to growth of new endothelial tissue, as with the platinum coil treatment. One significant drawback of flow diverters is that it may take weeks or months to form aneurysmal thrombus and significantly longer for the aneurysm neck to be covered with endothelial cells for full effect. This delay may be unacceptable when risk of aneurysm rupture (or re-rupture) is high. Moreover, flow diverters typically require antiplatelet therapy to prevent a thrombus from forming within the main channel of the blood vessel at the site of the flow diverter. Antiplatelet therapy may be contraindicated shortly after an initial aneurysm rupture has occurred because risk of re-rupture at this time is high and antiplatelet therapy tends to exacerbate intracranial hemorrhaging if re-rupture occurs. For these and other reasons, there is a need for innovation in the treatment of intracranial aneurysms. Given the severity of this condition, innovation in this field has immediate life-saving potential.

SUMMARY

The present technology is illustrated, for example, according to various aspects described below. Various examples of aspects of the present technology are described as numbered clauses (1, 2, 3, etc.) for convenience. These are provided as examples and do not limit the present technology. It is noted that any of the dependent clauses may be combined in any combination, and placed into a respective independent clause, e.g., clause (1, 15, 25, 34, etc.). The other clauses can be presented in a similar manner.

1. A method for making an occlusive device, the method comprising:
- obtaining a tubular mesh having a lumen therethrough;
- obtaining a forming member having an outer surface and an inner surface;
- everting the mesh over the forming member such that a first portion of the mesh conforms to the outer surface of the forming member and a second portion of the mesh conforms to the inner surface of the forming member;
- setting a shape of the mesh while positioned over the forming member.

2. The method of Clause 1, wherein the inner surface of the forming member is arcuate and defines a cavity in the forming member.

3. The method of Clause 1 or Clause 2, wherein the forming member has a substantially hemispherical shape.

4. The method of any one of Clauses 1 to 3, wherein the forming member includes a lumen extending therethrough.

5. The method of any one of Clauses 1 to 4, wherein the forming member is a first forming member, the inner surface is a first mating surface, and the method further comprises positioning the second portion of the mesh between the first mating surface of the first forming member and a second mating surface of a second forming member such that the second portion of the mesh conforms to the first and second mating surfaces of the first and second forming members, respectively.

6. The method of Clause 5, further comprising compressing the second portion of the mesh between the first and second mating surfaces.

7. The method of any one of Clauses 1 to 6, wherein setting the shape of the mesh comprises heat-treating the mesh while positioned on the forming member.

8. The method of any one of Clauses 1 to 7, wherein, after setting the shape of the mesh, the first and second portions of the mesh form a dual-layer sidewall that encloses an open volume.

9. The method of Clause 8, wherein the dual-layer sidewall has a generally hollow, hemispherical shape.

10. The method of Clause 8 or Clause 9, wherein the open volume has a substantially hemispherical shape.

11. The method of Clause 9, wherein the open volume is generally disc shaped.

12. The method of any one of Clauses 1 to 11, wherein, after setting the shape of the mesh, the mesh comprises a third portion that is generally tubular.

13. The method of any one of Clauses 8 to 12, further comprising coupling a coupling element to the mesh between the third portion of the mesh and the first and second portions of the mesh.

14. The method of any one of Clauses 1 to 13, further comprising positioning an elongate member within the lumen of the mesh.

15. The method of any one of Clauses 1 to 14, further comprising positioning an elongate member within a lumen of the forming member.

16. The method of Clause 14 or Clause 15, wherein the elongate member is a mandrel.

17. The method of any one of Clauses 14 to 16, wherein the elongate member comprises a generally tubular shape.

18. The method of any one of Clauses 1 to 17, wherein the mesh has a porosity sufficiently low to prevent blood flow across the mesh.

19. The method of any one of Clauses 1 to 18, wherein the mesh comprises a plurality of braided filaments.

20. The method of any one of Clauses 1 to 19, wherein the mesh comprises a plurality of interwoven filaments.

21. The method of any one of Clauses 1 to 20, wherein the mesh is a laser-cut tube.

22. The method of any one of Clauses 1 to 21, wherein the mesh comprises at least two layers.

23. The method of any one of Clauses 1 to Clause 22, wherein the mesh comprises a resilient and/or superelastic material.

24 The method of any one of Clauses 1 to 23, further comprising coupling a coupling element to the mesh.

25 The method of Clause 24, wherein the coupling element is coupled to the mesh such that the coupling element surrounds a circumference of the mesh.

26. The method of Clause 24 or Clause 25, wherein the coupling element comprises a marker band or wire tie.

27. The method of any one of Clauses 24 to 26, wherein the coupling element is radiopaque.

28. The method of any one of Clauses 1 to 27, wherein the forming member has a substantially cylindrical shape.

29. The method of Clause 28, wherein the forming member defines a lumen extending therethrough.

30. The method of Clause 29, wherein the inner surface is a wall of the lumen.

31. The method of any one of Clauses 1 to 30, wherein, after the shape of the mesh is set and the mesh is removed from the forming member, the mesh comprises a bowl shape with an opening extending through a thickness of the bowl.

32. The method of any one of Clauses 1 to 31, wherein, when positioned over the forming member, the first portion of the mesh is spaced apart from the second portion of the mesh by a thickness of the forming member between the inner and outer surfaces.

33. A method for making an occlusive device, the method comprising:

obtaining a tubular mesh having a lumen extending therethrough and a porosity configured to substantially prevent blood flow through the mesh, the mesh comprising first and second end portions and an intermediate portion therebetween;

obtaining a forming assembly comprising:

a first member having a generally globular shape and a lumen extending therethrough, wherein the first member has a first mating surface comprising at least a portion of an outer surface of the first member; and a second member having a generally hemispherical shape and a cavity with an arcuate surface, the second member having a lumen extending therethrough;

positioning at least a first portion of the intermediate portion of the mesh over an outer surface of the second member;

positioning at least a portion of the first end portion of the mesh within the lumen of the first member;

positioning at least a second portion of the intermediate portion of the mesh between the first mating surface of the first member and the arcuate surface of the second member such that the second portion substantially conforms to the first mating surface and the arcuate surface;

setting a shape of the mesh while the mesh is positioned on the forming assembly.

34. The method of Clause 33, further comprising positioning an elongate member within the lumen of the tubular mesh.

35. The method of Clause 33 or Clause 34, further comprising positioning an elongate member within the lumen of the second member.

36. The method of any one of Clauses 33 to 35, further comprising positioning an elongate member within the lumen of the first member.

37. The method of any one of Clauses 34 to 36, further comprising conforming the first and second end portions of the mesh to an outer surface of the elongate member.

38. The method of any one of Clauses 33 to 37, further comprising coupling a coupling element to the second end portion of the mesh at a location adjacent an outer surface of the second member.

39. The method of any one of Clauses 33 to 38, further comprising coupling a coupling element to the first end portion of the mesh at a location adjacent the arcuate surface of the second member.

40. The method of Clause 38 or Clause 39, wherein the coupling element surrounds a circumference of the mesh at the respective first or second end portion.

41. The method of any one of Clauses 38 to 40, wherein the coupling element comprises a marker band or wire tie.

42. The method of any one of Clauses 33 to 41, wherein the mesh is self-expanding.

43. The method of any one of Clauses 33 to 42, wherein the tubular mesh comprises a plurality of braided or interwoven filaments.

44. The method of Clause 43, wherein at least some of the filaments comprise a resilient and/or superelastic material.

45. The method of any one of Clauses 33 to 44, wherein positioning the second portion of the intermediate portion of the mesh between the first mating surface of the first member and the arcuate surface of the second member comprises positioning the first member at least partially within the cavity of the second member.

46. The method of any one of Clauses 33 to 45, further comprising compressing the second portion of the intermediate portion of the mesh between the first mating surface and the arcuate surface.

47. The method of any one of Clauses 33 to 46, further comprising fixing the position of the mesh relative to the forming assembly prior to setting the shape of the mesh.

48. The method of any one of Clauses 33 to 47, wherein setting the shape of the mesh comprises heat treating the mesh and forming assembly.

49. The method of any one of Clauses 33 to 48, wherein, after setting the shape of the mesh, the mesh comprises a contoured configuration in which the first and second end portions of the mesh have a substantially tubular shape and the intermediate portion of the mesh is substantially bowl-shaped.

50. A method for making an occlusive device, the method comprising:

- obtaining a tubular mesh having a lumen extending therethrough and a porosity configured to substantially prevent blood flow through the mesh, the mesh comprising first and second end portions and an intermediate portion therebetween;
- obtaining a forming member having a first surface, a second surface opposite the first surface along a thickness of the forming member, a sidewall therebetween, and a lumen extending through the first and second surfaces of the forming member;
- positioning at least a first portion of the intermediate portion of the mesh within the lumen of the forming member such that the first end portion of the mesh extends away from the first surface of the forming member in a first direction and the second end portion of the mesh extends away from the second surface of the forming member in a second direction opposite the first direction;
- everting the mesh over the forming member such that the first and second end portions of the mesh extend away from the second surface of the forming member in the second direction, wherein everting the mesh causes the first end portion of the mesh to substantially conform to the first and second surfaces and the sidewall of the forming member; and
- setting a shape of the mesh while positioned on the forming member.

51. The method of Clause 50, further comprising positioning an elongate member within the lumen of the tubular mesh and the lumen of the forming member.

52. The method of Clause 51, further comprising conforming the first and second end portions of the mesh to an outer surface of the elongate member.

53. The method of any one of Clauses 50 to 52, wherein the sidewall is annular such that the forming member comprises a generally cylindrical shape.

54. The method of any one of Clauses 50 to 53, further comprising coupling a coupling element to the mesh at a location adjacent the second surface of the forming member.

55. The method of Clause 54, wherein the coupling element is a marker band or wire tie.

56 The method of any one of Clauses 50 to 53, wherein the tubular mesh comprises a single layer.

57. The method of any one of Clauses 50 to 56, wherein the tubular mesh comprises a plurality of braided or interwoven filaments.

58. The method of Clause 57, wherein at least some of the filaments comprise a resilient and/or superelastic material.

59. The method of any one of Clauses 50 to 58, wherein setting a shape of the mesh comprises subjecting the mesh and forming member to a heat treatment procedure.

60. The method of any one of Clauses 50 to 59, wherein, after setting a shape of the mesh, the mesh comprises a contoured configuration comprising a substantially tubular open end portion, a substantially tubular intermediate portion, and a substantially disc shaped closed end portion disposed at an angle to the open end and intermediate portions.

61. The method of Clause 60, wherein the forming member is a first forming member and, after setting the shape of the mesh, the mesh is a contoured mesh, the method further comprising:

- separating the contoured mesh from the first forming member;
- obtaining a forming assembly comprising a second forming member and a third forming member, wherein:
  - the second forming member comprises a body portion having a first surface, a second surface opposite the first surface along a thickness of the second forming member, a sidewall therebetween, a protrusion extending from the first surface in a first direction, and a lumen extending through the body portion and the protrusion; and
  - the third forming member comprises a body portion having a first surface, a second surface opposite the first surface along a thickness of the third forming member, a sidewall therebetween, and a lumen extending through the body portion;
- positioning the intermediate portion of the contoured mesh within the lumen of the second forming member such that the closed end portion of the contoured mesh extends from the first surface of the second forming member and the open end portion of the contoured mesh extends from the second surface of the second forming member;
- positioning the closed end portion of the contoured mesh between the first surface and the protrusion of the second forming member and the second surface of the third forming member such that the closed end portion of the contoured mesh conforms to the first surface and the protrusion of the second forming member; and
- setting a second shape of the contoured mesh based on the second and third forming members.

62. The method of Clause 61, wherein the protrusion is substantially cylindrical.

63. The method of Clause 61 or Clause 62, wherein a first portion of the lumen of the second forming member comprises a first diameter and a second portion of the lumen of the second forming member comprises a second diameter different than the first diameter.

64. The method of any one of Clauses 61 to 63, further comprising positioning an elongate shaft within the lumen of the contoured mesh, the lumen of the second forming member, and the lumen of the third forming member.

65. The method of any one of Clauses 61 to 64, further comprising coupling a coupling element to the contoured mesh.

66. The method of any one of Clauses 61 to 65, wherein, after setting a second shape of the contoured mesh, the contoured mesh comprises a substantially tubular open end portion, a substantially tubular intermediate portion, and a closed end portion disposed at an angle to the open end and intermediate portions, wherein the closed end portion is substantially disc shaped with a protruding region.

67. The method of Clause 66, wherein the protruding region is substantially cylindrical.

68. A method for treating an aneurysm, the method comprising:

- positioning a distal end of an elongated shaft in an aneurysm cavity;
- releasing an occlusive member from the elongated shaft while the distal end of the elongated shaft is positioned within the aneurysm cavity such that the occlusive member self-expands to assume a first expanded state in which the occlusive member forms a first shape, wherein, in the first expanded state, the occlusive member encloses an interior region having a first interior volume; and
- delivering an embolic element between the occlusive member and the aneurysm wall to transform the occlusive member into a second expanded state in which the occlusive member defines a second interior volume less than the first interior volume, wherein the occlusive member forms a second shape in the second expanded state that is different than the first shape in the first expanded state.

69. The method of any one of the previous Clauses, wherein transforming the occlusive member into the second expanded shape includes injecting the embolic material to urge a portion of a sidewall of the expandable mesh in a direction away from a wall of the aneurysm and towards the interior region of the occlusive member.

70. The method of any one of the previous Clauses, wherein transforming the occlusive member into the second expanded shape includes injecting the embolic material to invert a portion of a sidewall of the occlusive member such that the portion is convex towards the aneurysm wall in the first expanded state and concave towards the aneurysm wall in the second expanded state.

71. The method of any one of the previous Clauses, wherein the embolic element comprises a liquid embolic.

72. The method of any one of the previous Clauses, wherein the embolic element comprises one or more embolization coils.

73. The method of any one of the previous Clauses, wherein delivering the embolic element occurs after the occlusive member is in the first expanded state.

74. The method of any one of the preceding Clauses, wherein the occlusive member is a mesh.

75. The method of any one of the preceding Clauses, wherein the occlusive member is a braid.

76. The method of any one of the preceding Clauses, wherein the occlusive member is a dual-layered braid.

77. The method of any one of the preceding Clauses, wherein the occlusive member has a globular or generally spherical shape in the first expanded state.

78. The method of any one of the preceding Clauses, wherein the occlusive member is cup or bowl-shaped in the second expanded state.

79. The method of any one of the preceding Clauses, wherein the second shape is a predetermined three-dimensional shape.

80. The method of any one of the preceding Clauses, wherein the occlusive member forms a multi-layer braid at the neck of the aneurysm in the second expanded state.

81. The method of any one of the previous Clauses, wherein the occlusive member comprises a plurality of braided filaments that assume a pre-set, three-dimensional shape in the expanded state.

82. The method of any one of the previous Clauses, wherein the occlusive member comprises a braid formed of 24, 32, 36, 48, 64, or 72 filaments.

83. The method of any one of the previous Clauses, wherein the occlusive member comprises a braid formed of a plurality of wires, some or all of which have a diameter of about 0.001 inches (0.00254 cm).

84. The method of any one of the previous Clauses, wherein the occlusive member comprises a braid formed of a plurality of wires, some or all of which have the same diameter.

85. The method of any one of the previous Clauses, wherein the occlusive member comprises a braid formed of a plurality of wires, at least some of which have different diameters.

86. The method of any one of the previous Clauses, wherein the occlusive member forms a closed, globular shape in the expanded state, the mesh having an aperture at a distal portion.

87. The method of any one of the previous Clauses, wherein, in the expanded state, the occlusive member forms one of a sphere, a prolate spheroid, or an oblate spheroid.

88. The method of any one of the previous Clauses, wherein the occlusive member comprises an inner layer and an outer layer.

89. The method of any one of the previous Clauses, wherein the occlusive member comprises an inner layer and an outer layer that meet at a fold at a distal portion of the occlusive member.

90. The method of Clause 22, wherein the expandable mesh includes an aperture at a distal portion, the aperture being defined by the fold.

91. The method of any one of the previous Clauses, wherein the occlusive member comprises an inner layer and an outer layer that meet at a fold at a proximal portion of the occlusive member.

92. The method of Clause 24, wherein the expandable mesh includes an aperture at a distal portion, the aperture being defined by the fold.

93. The method of any one of the previous Clauses, wherein the occlusive member has a maximum cross-sectional dimension of 3.0 mm, 3.5 mm, 4.0 mm, 4.5 mm, 5.0 mm, 5.5 mm, 6.0 mm, 6.5 mm, 7.0 mm, 7.5 mm, or 8.0 mm.

94. The method of any one of the previous Clauses, wherein the occlusive member is formed of a plurality of filaments having first and second ends fixed at a coupler.

95. The method of any one of the previous Clauses, wherein the occlusive member is formed of a plurality of filaments formed of an inner core material surrounded by an outer material.

96. The method of Clause 28, wherein the inner core material is a radiopaque material and the outer material is a superelastic material.

97. The method of any one of the previous Clauses, wherein the occlusive member is a laser-cut tube.

98. The method of any one of the previous Clauses, wherein the occlusive member comprises a plurality of filaments.

99. The method of Clause 31, wherein the filaments are interwoven.

100. The method of Clause 31 or Clause 32, wherein the filaments are braided.

101. The method of any one of Clauses 31 to 33, wherein each of the filaments has a first end and a second end opposite the first end, and wherein both the first and second ends of the filaments are fixed relative to one another at a coupler.

102. The method of Clause 34, wherein the coupler is disposed at a distal end of the occlusive member.

103. The method of Clause 34, wherein the coupler is disposed at a proximal end of the occlusive member.

104. The method of any one of Clauses 31 to 36, wherein each of the filaments terminate at only one end of the occlusive member.

105. The method of Clause 37, wherein the filaments form an opening at an end of the occlusive member opposite the only one end.

106. The method of Clause 38, wherein an inverted portion of each of the filaments define the opening.

107. The method of Clause 39, wherein the inverted portions of the filaments are configured to move relative to one another.

108. The method of any one of the previous Clauses, wherein the embolic element comprises a biopolymer and a chemical crosslinking agent.

109. The method of Clause 42, wherein the biopolymer includes chitosan, a derivative of chitosan, an analog of chitosan, or a combination thereof.

110. The method of Clause 42 or Clause 43, wherein the chemical crosslinking agent includes genipin, a derivative of genipin, an analog of genipin, or a combination thereof.

111. The method of any one of Clauses 42 to 44, wherein the embolic element further comprises a physical crosslinking agent.

112. The method of Clause 45, the physical crosslinking agent includes β glycerophosphate, a derivative of β glycerophosphate, an analog of β glycerophosphate, or a combination thereof.

113. The method of Clause 42, wherein the biopolymer includes chitosan, a derivative of chitosan, an analog of chitosan, or a combination thereof;

the chemical crosslinking agent includes genipin, a derivative of genipin, an analog of genipin, or a combination thereof; and the physical crosslinking agent includes β glycerophosphate, a derivative of β glycerophosphate, an analog of β glycerophosphate, or a combination thereof.

114. The method of any one of the preceding Clauses, wherein the embolic element comprises a contrast agent.

115. The method of Clause 48, wherein the contrast agent is selected to provide diminishing radiopacity.

116. The method of Clause 48 or Clause 49, wherein the contrast agent includes iohexol, a derivative of iohexol, an analog of iohexol, or a combination thereof.

117. A method for treating an aneurysm, the method comprising:

positioning an expandable occlusive member in an initial expanded state within an aneurysm, wherein in the initial expanded state the expandable occlusive member provides a number of layers across a neck of the aneurysm; and doubling the number of layers of the occlusive device across the neck of the aneurysm by introducing an embolic element to the aneurysm cavity.

118. The method of Clause 51, wherein the number of layers is one.

119. The method of Clause 51, wherein the number of layers is two.

120. The method of any one of Clauses 51 to 53, wherein the layers are mesh layers.

121. The method of any one of Clauses 51 to 54, wherein the occlusive member has a first shape in the initial expanded state, and wherein introducing the embolic element transforms the occlusive member from the initial expanded state to a secondary expanded state in which the occlusive member forms a second shape different than the first shape.

122. The method of Clause 55, wherein a volume enclosed by the first shape is greater than a volume enclosed by the second shape.

123. A method for imaging treatment of an aneurysm, the method comprising:

acquiring a first image visualizing:

an occlusive member positioned within an aneurysm, the occlusive member including a first radiopaque marker; and a conduit having a distal portion positioned within an aneurysm, the distal portion of the conduit including a second radiopaque marker; and acquiring a second image in which the first radiopaque marker is further from the second radiopaque marker than in the first image.

124. The method of Clause 56, wherein, in the second image, the first radiopaque marker is positioned proximal to the second radiopaque marker.

125. The method of one of Clauses 56 to 57, wherein, in the second image, the first radiopaque marker is positioned closer to a neck of the aneurysm than in the first image.

126. The method of any one of Clauses 56 to 58, wherein, in the first image, the first radiopaque marker is positioned in a distal half of the occlusive member.

127. The method of any one of Clauses 56 to 59, wherein, in the first image, the first radiopaque marker is positioned on a distal-facing surface of the occlusive member.

128. The method of any one of Clauses 56 to 60, wherein, in the first image, the first radiopaque marker is positioned proximal to the second radiopaque marker.

129. The method of any one of Clauses 56 to 61, wherein, in the first image and in the second image, the second radiopaque marker is disposed nearer to a dome of the aneurysm than the first radiopaque marker.

130. The method of any one of Clauses 56 to 62, wherein, in the second image, a radiopaque occlusive element is visible in a space between the first radiopaque marker and the second radiopaque marker.

131. The method of any one of Clauses 56 to 63, further comprising acquiring a third image in which the first radiopaque marker is further from the second radiopaque marker than in the second image.

132. The method of any one of Clauses 56 to 64, wherein acquiring the first image and acquiring the second image each comprises acquiring a fluoroscopic image.

133. A device for treating an aneurysm, the device comprising:

a mesh having an expanded, unconstrained state, the mesh formed of a plurality of braided filaments, each of the filaments having a first end and a second end, wherein the mesh has a proximal portion configured to be positioned over the neck of an aneurysm and a distal portion;

a first coupler at the proximal portion, wherein the first ends are secured relative to one another at the first coupler; and a second coupler at the distal portion, wherein the second ends are secured relative to one another at the second coupler, wherein the mesh is formed of a wall comprising a first portion, a second portion, and a ridge, wherein the first portion extends between the first coupler and the ridge and the second portion extends between the ridge and the second coupler, and wherein the mesh includes a cavity at the distal portion, and wherein all or a portion of the distal coupler is positioned within the cavity.

134. The device of Clause 133, wherein the mesh has a single layer delivery configuration.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

The

Methods for treating intracranial aneurysms in accordance with at least some embodiments of the present technology include positioning an expandable occlusive member within the aneurysm and introducing an embolic element between the occlusive member and an aneurysm wall. Introduction of the embolic element both fills space within the aneurysm cavity and deforms the occlusive member from a first expanded state to a second expanded state to fortify the occlusive member at the neck of the aneurysm. Deformation of the occlusive member from a first expanded state to a second expanded state provides the additional advantage of giving visual confirmation to the physician that the delivered amount of embolic element sufficiently fills the aneurysm cavity. In addition to providing a structural support and anchor for the embolic element, the occlusive member provides a scaffold for tissue remodeling and diverts blood flow from the aneurysm. Moreover, the embolic element exerts a substantially uniform pressure on the occlusive member towards the neck of the aneurysm, thereby pressing the portions of the occlusive member positioned adjacent the neck against the inner surface of the aneurysm wall such that the occlusive member forms a complete and stable seal at the neck.

Specific details of systems, devices, and methods for treating intracranial aneurysms in accordance with embodiments of the present technology are described herein with reference to FIGS. 1A-5B. Although these systems, devices, and methods may be described herein primarily or entirely in the context of treating saccular intracranial aneurysms, other contexts are within the scope of the present technology. For example, suitable features of described systems, devices, and methods for treating saccular intracranial aneurysms can be implemented in the context of treating non-saccular intracranial aneurysms, abdominal aortic aneurysms, thoracic aortic aneurysms, renal artery aneurysms, arteriovenous malformations, tumors (e.g. via occlusion of vessel(s) feeding a tumor), perivascular leaks, varicose veins (e.g. via occlusion of one or more truncal veins such as the great saphenous vein), hemorrhoids, and sealing endoleaks adjacent to artificial heart valves, covered stents, and abdominal aortic aneurysm devices among other examples. Furthermore, it should be understood, in general, that other systems, devices, and methods in addition to those disclosed herein are within the scope of the present disclosure. For example, systems, devices, and methods in accordance with embodiments of the present technology can have different and/or additional configurations, components, procedures, etc. than those disclosed herein. Moreover, systems, devices, and methods in accordance with embodiments of the present disclosure can be without one or more of the configurations, components, procedures, etc. disclosed herein without deviating from the present technology.

I. Overview of Systems of the Present Technology

Figure 1A:
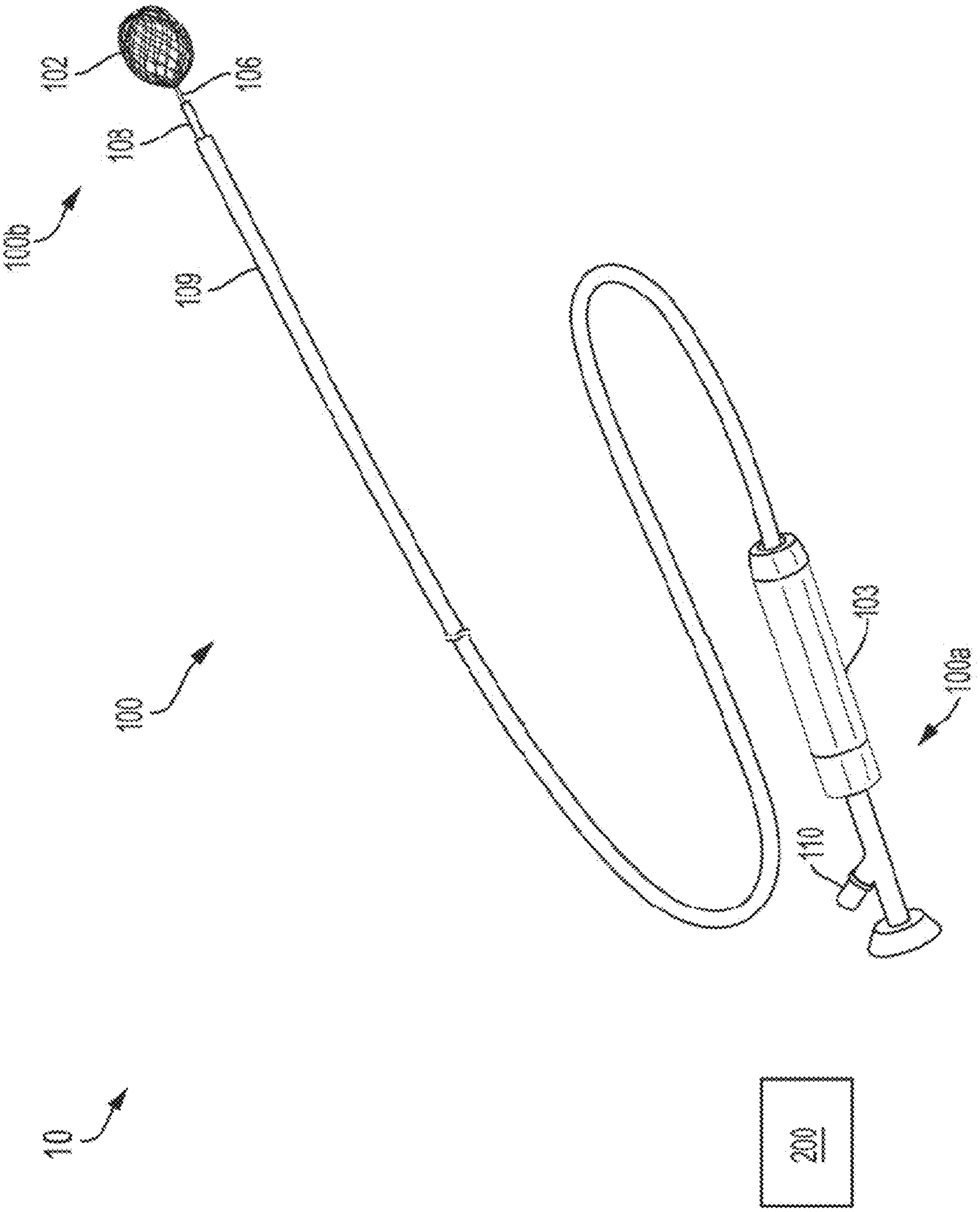
FIG. 1A shows a perspective view of a system for treating an aneurysm in accordance with the present technology.

FIG. 1A illustrates a view of a system 10 for treating intracranial aneurysms according to one or more embodiments of the present technology. As shown in FIG. 1A, the system 10 comprises a treatment system 100 and an embolic kit 200 for use with one or more components of the treatment system 100. The treatment system 100 may comprise an occlusive member 102 (shown in an expanded state) detachably coupled to a delivery system, and the delivery system may be configured to intravascularly position the occlusive member 102 within an aneurysm. The embolic kit 200 may comprise one or more substances or devices that alone or in combination form an embolic element that is configured to co-occupy the internal volume of the aneurysm with the occlusive member 102. In some embodiments, the treatment system 100 may be configured to deliver the embolic element (and/or one or more precursors thereof) to the aneurysm. Additionally or alternatively, the system 10 may include a separate delivery system (not shown) for delivering the embolic element (and/or one or more precursors thereof) to the aneurysm cavity.

As shown in FIG. 1A, the treatment system 100 has a proximal portion 100*a* configured to be extracorporeally positioned during treatment and a distal portion 100*b* configured to be intravascularly positioned within a blood vessel (such as an intracranial blood vessel) at a treatment site at or proximate an aneurysm. The treatment system 100 may include a handle 103 at the proximal portion 100*a*, the occlusive member 102 at the distal portion 100*b*, and a plurality of elongated shafts or members extending between the proximal and distal portions 100*a* and 100*b*. In some embodiments, such as that shown in FIG. 1A, the treatment system 100 may include a first elongated shaft 109 (such as a guide catheter or balloon guide catheter), a second elongated shaft 108 (such as a microcatheter) configured to be slidably disposed within a lumen of the first elongated shaft 109, and an elongated member 106 configured to be slidably disposed within a lumen of the second elongated shaft 108. In some embodiments, the treatment system 100 does not include the first elongated shaft 109 and only includes the second elongated shaft 108.

Figure 1B:
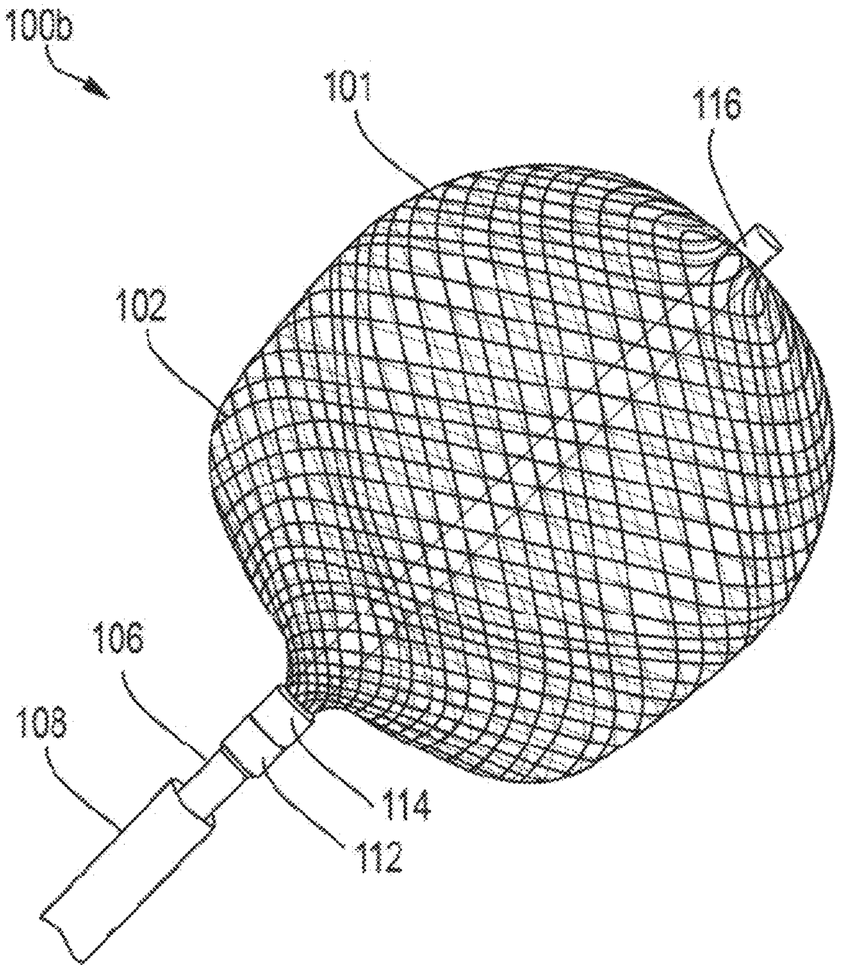
FIG. 1B shows an enlarged view of a distal portion of the treatment system of FIG. 1A in accordance with the present technology.

FIG. 1B is an enlarged view of the distal portion 100*b* of the treatment system 100. Referring to FIGS. 1A and 1B together, the occlusive member 102 may be detachably coupled to a distal end of the elongated member 106. For example, the elongated member 106 may include a first coupler 112 at its distal end, and the occlusive member 102 may include a second coupler 114 configured to detachably couple with the first coupler 112. The treatment system 100 may further comprise a conduit 116 extending from the handle 103 (for example, via port 110) distally to the distal portion 100*b* of the treatment system 100. The conduit 116 is configured to deliver the embolic element (and/or one or more precursors thereof) through one or more components of the delivery system (e.g., the first or second elongated shafts 109, 108, the elongated member 106, etc.) to a position at the exterior of the occlusive member 102. As such, the embolic element may be positioned between the occlusive member 102 and an inner wall of the aneurysm cavity, as described in greater detail below.

According to some embodiments, the second elongated shaft 108 is generally constructed to track over a conventional guidewire in the cervical anatomy and into the cerebral vessels associated with the brain and may also be chosen according to several standard designs that are generally available. Accordingly, the second elongated shaft 108 can have a length that is at least 125 cm long, and more particularly may be between about 125 cm and about 175 cm long. In some embodiments, the second elongated shaft 108 may have an inner diameter of about 0.015 inches (0.0381 cm), 0.017 inches (0.043 cm), about 0.021 inches (0.053 cm), or about 0.027 inches (0.069 cm). Other designs and dimensions are contemplated.

The elongated member 106 can be movable within the first and/or second elongated shafts 109, 108 to position the occlusive member 102 at a desired location. The elongated member 106 can be sufficiently flexible to allow manipulation, e.g., advancement and/or retraction, of the occlusive member 102 through tortuous passages. Tortuous passages can include, for example, catheter lumens, microcatheter lumens, blood vessels, urinary tracts, biliary tracts, and airways. The elongated member 106 can be formed of any material and in any dimensions suitable for the task(s) for which the system is to be employed. In some embodiments, the elongated member 106 can comprise a solid metal wire. In some embodiments, the elongated member 106 may comprise any other suitable form of shaft such as an elongated tubular shaft.

In some embodiments, the elongated member 106 can comprise stainless steel, nitinol, or other metal or alloy. In some embodiments, the elongated member 106 can be surrounded over some or all of its length by a coating, such as, for example, polytetrafluoroethylene. The elongated member 106 may have a diameter that is generally constant along its length, or the elongated member 106 may have a diameter that tapers radially inwardly, along at least a portion of its length, as it extends in a distal direction.

According to several embodiments, the conduit 116 may be a catheter or elongated shaft that is delivered separately from the second elongated shaft 108.

A. Selected Examples of Occlusive Members

Figure 1C:
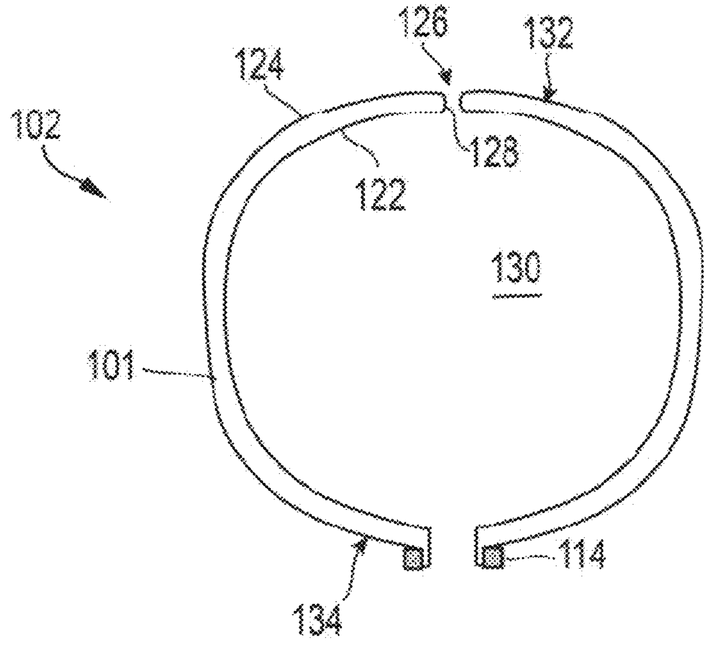
FIGS. 1C and 1D are sectioned views of occlusive members in an expanded state in accordance with the present technology.

FIG. 1C is a sectioned view of the occlusive member 102, shown in an expanded state and detached from the treatment system 100. Referring to FIGS. 1B and 1C, the occlusive member 102 may comprise an expandable element having a low-profile or constrained state while positioned within a catheter (such as the second elongated shaft 108) for delivery to the aneurysm and an expanded state in which the expandable element is configured to be positioned within an aneurysm (such as a cerebral aneurysm).

According to some embodiments, the occlusive member 102 may comprise a mesh 101 formed of a plurality of braided filaments that have been heat-set to assume a predetermined shape enclosing an interior volume 130 when the mesh 101 is in an expanded, unconstrained state. Example shapes include a globular shape, such as a sphere, a prolate spheroid, an oblate spheroid, and others. As depicted in FIG. 1C, the mesh 101 may have inner and outer layers 122, 124 that have proximal ends fixed relative to one another at the second coupler 114 and meet distally at a distal fold 128 surrounding an aperture 126. While the inner and outer layers 122, 124 are depicted spaced apart from one another along their lengths, the inner and outer layers 122, 124 may be in contact with one another along all or a portion of their lengths. For example, the inner layer 122 may press radially outwardly against the outer layer 124. In some embodiments, the occlusive member 102 may be formed of a single layer or mesh or braid.

In some embodiments, the inner and outer layers 122, 124 have their distal ends fixed relative to one another at a distal coupler and meet proximally at a proximal fold surrounding an aperture. In any case, in some embodiments the conduit 116 may be configured to be slidably positioned through some or all of the second coupler 114, the interior volume 130 of the expanded mesh 101, and the opening 126.

The inner and outer layers 122 and 124 may conform to one another at the distal portion (for example as shown in FIG. 1C) to form a curved distal surface. For example, at least at the distal portion of the occlusive member 102, the inner and outer layers 122 and 124 may extend distally and radially inwardly, towards the aperture 126. In some embodiments, the outer and/or inner layers 122 and 124 extend distally and radially outwardly from the second coupler 114, then extend distally and radially inwardly up to a distal terminus of the occlusive member 102 (e.g., the fold 128). The occlusive member 102 and/or layers thereof may be curved along its entire length, or may have one or more generally straight portions. In some embodiments, the curved surface transitions to a flat or substantially flat, distal-most surface that surrounds the aperture 126. In some embodiments, the curved surface transitions to a distal-most surface that surrounds the aperture 126 and has a radius of curvature that is greater than the average radius of curvature of the rest of the occlusive member 102. Having a flat or substantially flat distal surface, or a distal surface with a radius of curvature that is greater than the average radius of curvature of the rest of the occlusive member 102, may be beneficial for delivering the embolic element 230 in that it creates a small gap between the distal surface of the occlusive member 102 and the dome of the aneurysm A (see, for example, FIG. 3B). In some embodiments, the surface of the occlusive member 102 surrounding the aperture 126 is curved and/or has generally the same radius of curvature as the remainder of the occlusive member 102.

Figure 1D:
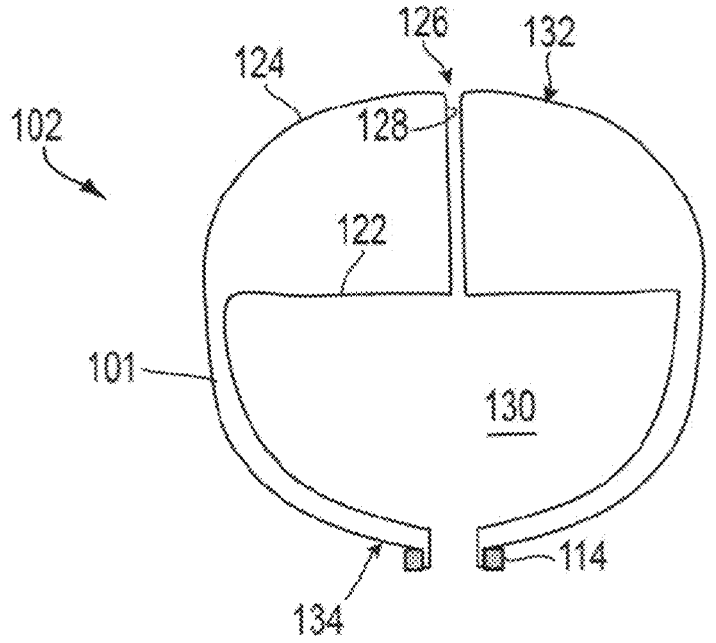
Figure 2:
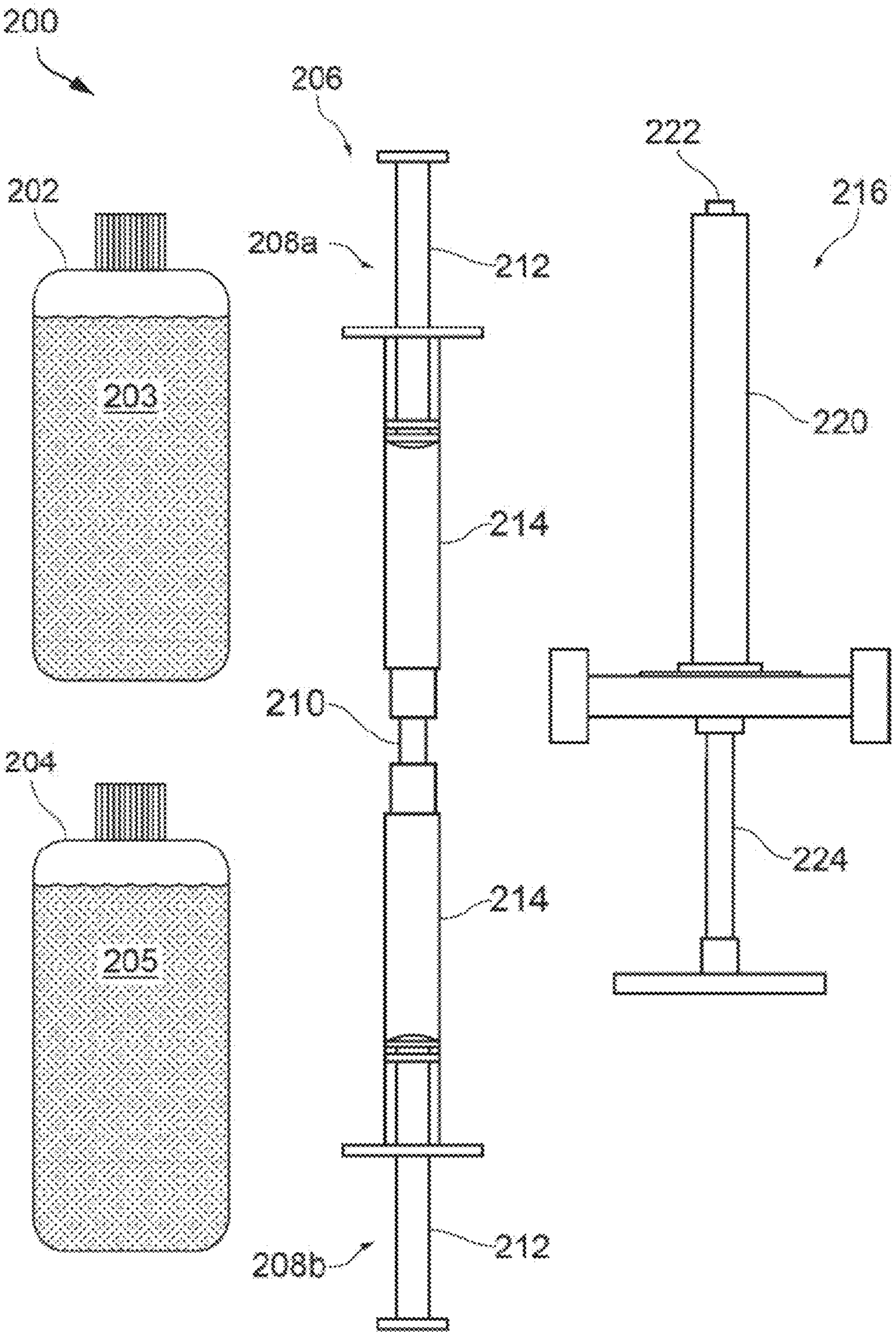
FIG. 2 shows an embolic kit according to the present technology.

In any case, the inner layer 122 may have a shape that substantially conforms to the shape of the outer layer 124, or the inner and outer layers 122, 124 may have different shapes. For example, as shown in FIG. 1D, the inner layer 122 may have a diameter or cross-sectional dimension that is less than the outer layer 124. Such a configuration may be beneficial in that the embolic element 230 experiences less resistance, at least initially, when pushing the distal wall of the occlusive member 102 downwardly towards the neck (as described in greater detail below).

In any case, both the proximal portion and the distal portion of the mesh 101 can form generally closed surfaces. However, unlike at the proximal portion of the mesh 101, the portion of the filaments at or near the fold 128 at the distal portion of the mesh 101 can move relative to one another. As such, the distal portion of the mesh 101 has both the properties of a closed end and also some properties of an open end (like a traditional stent), such as some freedom of movement of the distal-most portions of the filaments and an opening through which the conduit 116, a guidewire, guidetube, or other elongated member may pass through.

In some embodiments, each of the plurality of filaments have a first end positioned at the proximal portion of the mesh 101 and a second end also positioned at the proximal portion of the mesh 101. Each of the filaments may extend from its corresponding first end distally along the body of the mesh 101 to the fold 128, invert, then extend proximally along the mesh body to its corresponding second end at the proximal portion of the mesh 101. As such, each of the plurality of filaments have a first length that forms the inner layer 122 of the mesh 101, a second length that forms the outer layer 124 of the mesh 101, and both first and second ends fixed at the proximal portion of the mesh 101. In some embodiments, the occlusive member 102 may comprise a mesh formed of a single layer, or a mesh formed of three or more layers.

In some embodiments, the distal end surface of the mesh 101 is completely closed (i.e., does not include an aperture). In some embodiments the filaments are fixed relative to one another at both the proximal and distal ends of the occlusive member 102.

The mesh 101 may be formed of metal wires, polymer wires, or both, and the wires may have shape memory and/or superelastic properties. The mesh 101 may be formed of 24, 32, 36, 48, 64, 72, 96, 128, or 144 filaments. The mesh 101 may be formed of a range of filament or wire sizes, such as wires having a diameter of from about 0.0004 inches to about 0.0020 inches, or of from about 0.0009 inches to about 0.0012 inches. In some embodiments, each of the wires or filaments have a diameter of about 0.0004 inches, about 0.0005 inches, about 0.0006 inches, about 0.0007 inches, about 0.0008 inches, about 0.0009 inches, about 0.001 inches, about 0.0011 inches, about 0.0012 inches, about 0.0013 inches, about 0.0014 inches, about 0.0015 inches, about 0.0016 inches, about 0.0017 inches, about 0.0018 inches, about 0.0019 inches, or about 0.0020 inches. In some embodiments, all of the filaments of the braided mesh 101 may have the same diameter. For example, in some embodiments, all of the filaments have a diameter of about 0.001 inches. In some embodiments, some of the filaments may have different cross-sectional diameters. For example, some of the filaments may have a slightly thicker diameter to impart additional strength to the braided layers. In some embodiments, some of the filaments can have a diameter of about 0.001 inches, and some of the filaments can have a diameter of greater than 0.001 inches. The thicker filaments may impart greater strength to the braid without significantly increasing the device delivery profile, with the thinner wires offering some strength while filling-out the braid matrix density.

The occlusive member 102 can have different shapes and sizes in an expanded, unconstrained state. For example, the occlusive member 102 may have a bullet shape, a barrel-shape, an egg shape, a dreidel shape, a bowl shape, a disc shape, a cylindrical or substantially cylindrical shape, a barrel shape, a chalice shape, etc.

B. Selected Examples of Embolic Kits

The embolic kit 200 may include one or more precursors for creation of a liquid embolic. For example, the embolic kit 200 may include a first container 202 containing a first precursor material 203 (shown schematically), a second container 204 containing a second precursor material 205 (also shown schematically), and a mixing device 206 suitable for mixing the first and second precursor materials 203, 205. The mixing device 206 can include mixing syringes 208 (individually identified as mixing syringes 208*a*, 208*b*) and a coupler 210 extending between respective exit ports (not shown) of the mixing syringes 208. The mixing syringes 208*a*, 208*b* each include a plunger 212 and a barrel 214 in which the plunger 212 is slidably received.

The embolic kit 200 can further include an injection syringe 216 configured to receive a mixture of the first and second precursor materials 203, 205 and deliver the mixture to a proximal portion 100*b* of the treatment assembly 100. The injection syringe 216 can include a barrel 220, an exit port 222 at one end of the barrel 220, and a plunger 224 slidably received within the barrel 220 via an opposite end of the barrel 220. The handle 103 of the treatment system 100 may have a coupler configured to form a secure fluidic connection between the lumen and the exit port 222 of the injection syringe 216.

The first and second precursor materials 203, 205 can include a biopolymer and a chemical crosslinking agent, respectively. The chemical crosslinking agent can be selected to form covalent crosslinks between chains of the biopolymer. In some embodiments, the biopolymer of the first precursor material 203 includes chitosan or a derivative or analog thereof, and the chemical crosslinking agent of the second precursor material 205 includes genipin or a derivative or analog thereof. Other suitable crosslinking agents for use with chitosan include glutaraldehyde, functionalized polyethylene glycol, and derivatives and analogs thereof. In other embodiments, the biopolymer of the first precursor material 203 can include collagen or a derivative or analog thereof, and the chemical crosslinking agent of the second precursor material 205 can include hexamethylene diisocyanate or a derivative or analog thereof. Alternatively or in addition, genipin or a derivative or analog thereof can be used as a chemical crosslinking agent for a collagen-based biopolymer. In still other embodiments, the biopolymer of the first precursor material 203 and the chemical crosslinking agent of the second precursor material 205 can include other suitable compounds alone or in combination.

Mixing the biopolymer of the first precursor material 203 and the chemical crosslinking agent of the second precursor material 205 can initiate chemical crosslinking of the biopolymer. After the first and second precursor materials 203, 205 are mixed, chemical crosslinking of the biopolymer occurs for enough time to allow the resulting embolic element 230 be delivered to the aneurysm before becoming too viscous to move through the lumen of the conduit 116. In addition, the period of time during which chemical crosslinking of the biopolymer occurs can be short enough to reach a target deployed viscosity within a reasonable time (e.g., in the range of 10-60 minutes; or at most 40 minutes, 30 minutes, 20 minutes, or 10 minutes) after delivery. The target deployed viscosity can be high enough to cause an agglomeration of the embolic element 230 to remain within the internal volume of the aneurysm without reinforcing the neck.

In at least some cases, the biopolymer has a non-zero degree of chemical crosslinking within the first precursor material 203 before mixing with the chemical crosslinking agent. This can be useful, for example, to customize the curing window for the embolic element 230 so that it corresponds well with an expected amount of time needed to deliver the material to the aneurysm. The degree of chemical crosslinking of the biopolymer within the first precursor material 203 before mixing with the chemical crosslinking agent, the ratio of the biopolymer to the chemical crosslinking agent, and/or one or more other variables can be selected to cause the embolic element 230 to have a viscosity suitable for delivery to the aneurysm via the lumen of the conduit 116 for a suitable period of time (e.g., a period within a range from 10 minutes to 40 minutes) after mixing of the first and second precursor materials 203, 205. In at least some cases, the first and second precursor materials 203, 205 are mixed in proportions that cause a weight ratio of the biopolymer to the chemical crosslinking agent in the resulting embolic element 230 to be within a range from 10:1 to 100:1, such as from 10:1 to 30:1, or from 15:1 to 50:1, or from 15:1 to 25:1. In a particular example, the first and second precursor materials 203, 205 are mixed in proportions that cause a weight ratio of the biopolymer to the chemical crosslinking agent in the resulting embolic element 230 to be 30:1.

Use of a biopolymer instead of an artificial polymer in the first precursor material 203 may be advantageous because biopolymers tend to be more readily bioabsorbed than artificial polymers and/or for other reasons. Furthermore, use of a chemical crosslinking agent instead of a physical crosslinking agent (i.e., a crosslinking agent that forms noncovalent crosslinks between chains of the biopolymer) in the second precursor material 205 may be advantageous because chemically crosslinked polymers tend to be more cohesive than physically crosslinked polymers and/or for other reasons. In the context of forming a tissue scaffold within an aneurysm, high cohesiveness of the embolic element 230 may be more important than it is in other contexts to secure the cured embolic element 230 within the aneurysm 302. For example, high cohesiveness of the embolic element 230 may reduce or eliminate the possibility of a piece of the embolic element 230 breaking free and entering a patient's intracerebral blood stream during delivery.

The first and second precursor materials 203, 205 may include other components and/or the system 200 may include other precursor materials intended for mixing with the first and second precursor materials 203, 205. For example, the first, second, and/or another precursor material may include a physical crosslinking agent. The presence of a physical crosslinking agent may be useful to form physical crosslinks that complement chemical crosslinks from the chemical crosslinking agent. The combination of chemical and physical crosslinks may enhance the cohesiveness of the embolic element 230. Suitable physical crosslinking agents for use with chitosan-based biopolymers include β glycerophosphate, mannitol, glucose, and derivatives and analogs thereof. In these and other cases, the embolic element 230 may include multiple chemical crosslinking agents and/or multiple physical crosslinking agents.

A contrast agent is another component that may be added to the precursor materials. The presence of a contrast agent within the embolic element 230 can be useful to visualize delivery of the embolic element 230 using fluoroscopy. One problem with using conventional platinum coils in intracranial aneurysms is that the persistent radiopacity of the coils tends to interfere with visualizing other aspects of the treatment in follow-up imaging. For example, the presence of platinum coils within an aneurysm may make it difficult or impossible to detect by fluoroscopy the presence of blood-carried contrast agent that would otherwise indicate recanalization. In at least some embodiments of the present technology, a contrast agent within the embolic element 230 is selected to provide radiopacity that diminishes over time. For example, the contrast agent may initially be radiopaque to facilitate delivery of the embolic element 230 and then become less radiopaque to facilitate follow-up imaging. In a particular example, the first, second, and/or another precursor material includes iohexol or a derivative or analog thereof as a suitable contrast agent.

In animal studies, the liquid embolics of the present technology were shown to provide (a) complete or nearly complete volumetric filling of the aneurysm internal volume, and (b) complete or nearly complete coverage of the aneurysm neck with new endothelial tissue. These features, among others, are expected to result in a lower recanalization rate than that of platinum coil treatments and faster aneurysm occlusion than that of flow diverters. Furthermore, the injectable scaffold material is expected to be bioabsorbed and thereby reduced in volume over time. Thus, unlike platinum coils, the injectable scaffold is expected to have little or no long-term mass effect. Furthermore, the injectable scaffold material can be configured to have diminishing radiopacity; therefore, when so configured it will not interfere future CT and MRI imaging and procedures. Embodiments of the present technology can have these and/or other features and advantages relative to conventional counterparts whether or not such features and advantages are described herein.

In some embodiments, the embolic kit 200 and/or embolic element 230 may be any embolic or occlusive device, such as one or more embolic coils, polymer hydrogel(s), polymer fibers, mesh devices, or combinations thereof. The embolic kit 200 may include one or more precursors that, once mixed together, form the embolic element 230 that remains within the aneurysm. In some embodiments, the embolic kit 200 may include the embolic element pre-mixed.

II. Selected Methods for Treating Aneurysms

FIGS. 3A-3G depict an example method for treating an aneurysm A with the systems 10 of the present technology. To begin, a physician may intravascularly advance the second elongated shaft 108 towards an intracranial aneurysm (or other treatment location such as any of those described herein) with the occlusive member 102 in a low-profile state. A distal portion of the second elongated shaft 108 may be advanced through a neck N of the aneurysm A to locate a distal opening of the second elongated shaft 108 within an interior cavity of the aneurysm A. The elongated member 106 may be advanced distally relative to the second elongated shaft 108 to push the occlusive member 102 through the opening at the distal end of the second elongated shaft 108, thereby releasing the occlusive member 102 from the shaft 108 and allowing the occlusive member 102 to self-expand into a first expanded state.

Figure 3A:
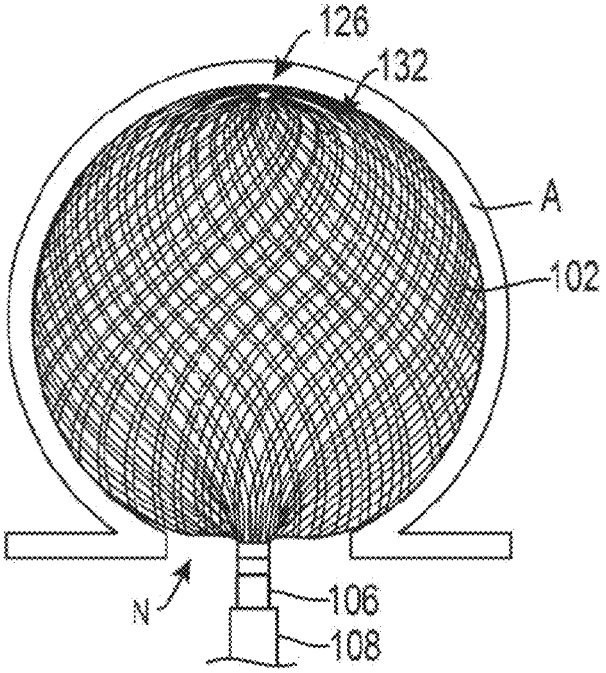
FIGS. 3A-3G depict an example method of treating an aneurysm with the treatment systems of the present technology.
Figure 3B:
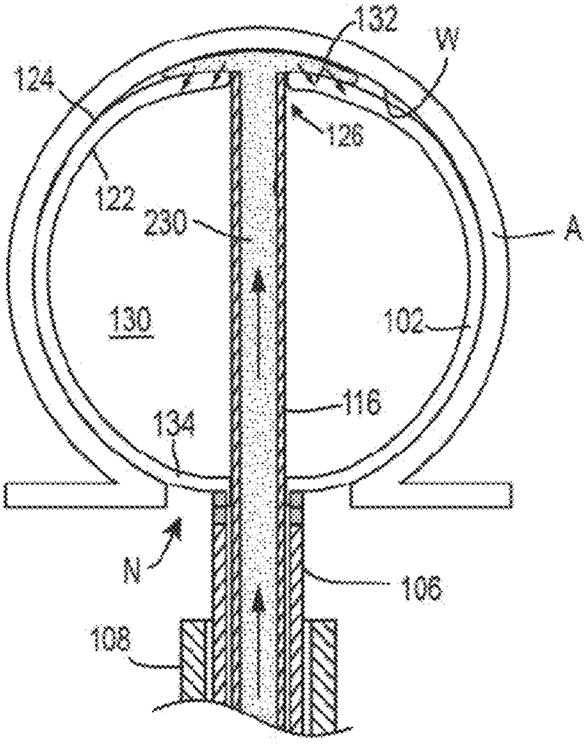

FIG. 3A shows the occlusive member 102 in a first expanded state, positioned in an aneurysm cavity and still coupled to the elongated member 106. As shown in FIG. 3A, in the first expanded state, the occlusive member 102 may assume a predetermined shape that encloses an internal volume 130 (see FIG. 1C). In this first expanded state, the occlusive member 102 may generally conform to the shape of the aneurysm A. As illustrated in FIG. 3B with the occlusive member 102 and delivery system shown in cross-section, the conduit 116 may be advanced through the internal volume 130 of the occlusive member 102 such that a distal opening of the conduit 116 is at or distal to the aperture 126 at the distal portion of the occlusive member 102. The embolic element 230 may be delivered through the conduit 116 to a space between the occlusive member 102 and an inner surface of the aneurysm wall W.

In some embodiments, the method includes mixing the first and second precursor materials 203, 205 (FIG. 2) to form the embolic element 230. Mixing of the first and second precursor materials 203, 205 may occur prior to introducing the embolic element 230 to the treatment system 100 and/or during delivery of the embolic element through the conduit 116 to the aneurysm. In a particular example, the first precursor material 203 is loaded into one of the barrels 214, the second precursor materials 205 is loaded into the other barrel 214, and the mixing syringes 208 are coupled via the coupler 210. To mix the first and second precursor materials 203, 205, the plungers 212 are alternately depressed, thereby causing the first and second precursor materials 203, 205 to move repeatedly from one barrel 214 to the other barrel 214. After suitably mixing the precursor materials, the resulting embolic element 230 can be loaded into the barrel 220 of the injection syringe 216. The injection syringe 216 may then be coupled to a proximal end of the conduit 116 to deliver the embolic element 230 through the conduit 116 and into the aneurysm A. As the embolic element 230 passes through the lumen of the conduit 116, chemical crosslinking of the biopolymer can continue to occur.

Figure 3C:
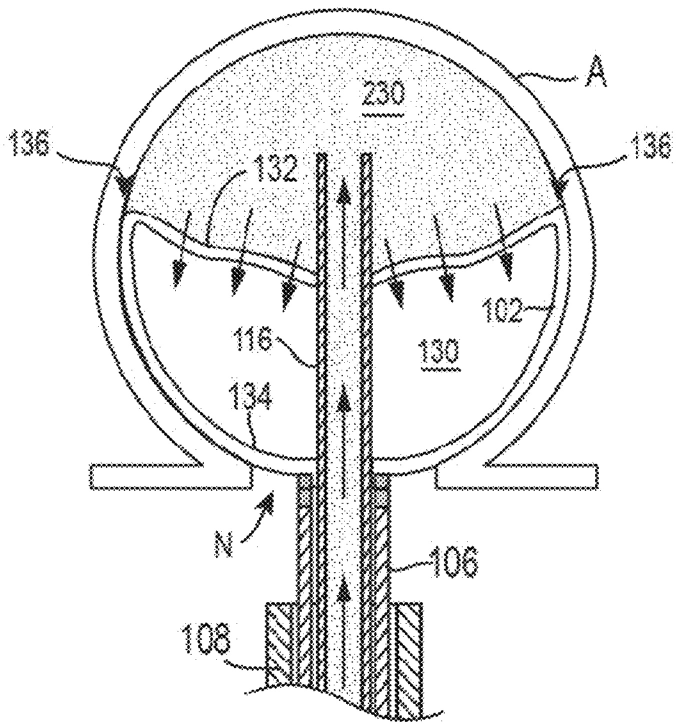
Figure 3D:
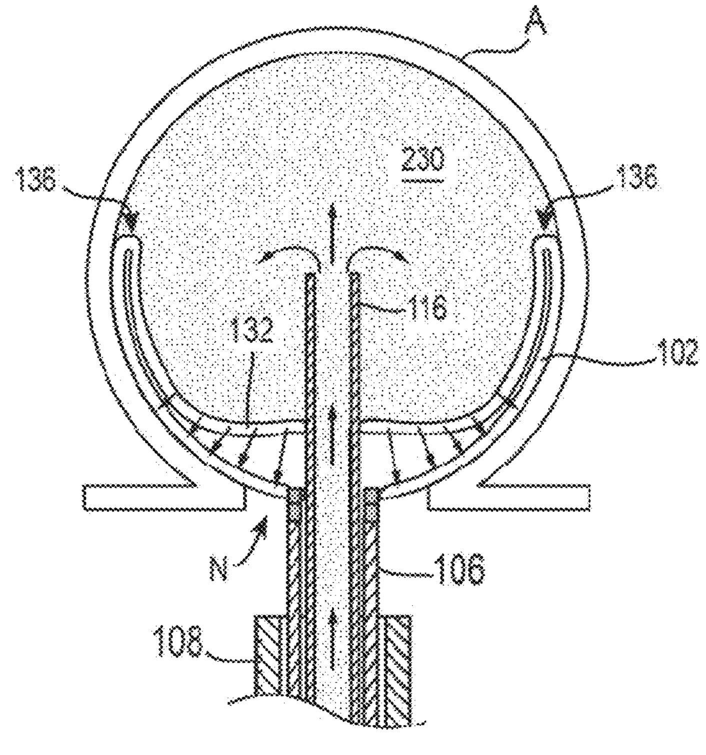

Still with reference to FIG. 3B, as the embolic element 230 is delivered between the dome of the aneurysm A and the distal portion 132 of the wall of the occlusive member 102, pressure builds between the aneurysm wall W and the occlusive member 102. As shown in the progression of FIGS. 3B-3D, when the forces on the occlusive member 102 reach a threshold level, the embolic element 230 pushes the distal wall 132 downwardly towards the neck N of the aneurysm A. The embolic element 230 exerts a substantially uniform pressure across the distal surface of the occlusive member 102 that collapses the occlusive member 102 inwardly on itself such that the rounded distal wall 132 transitions from concave towards the neck N of the aneurysm A to convex towards the neck N. The pressure and inversion of the distal portion of the wall 132 creates an annular fold 136 that defines the distal-most edge of the occlusive member 102. As the occlusive member 102 continues to invert, the position of the fold 136 moves towards the neck N, which continues until a distal-most half of the occlusive member 102 has inverted. In some embodiments, the occlusive member 102 may include one or more portions configured to preferentially flex or bend such that the occlusive member 102 folds at a desired longitude. Moreover, as the occlusive member 102 collapses, a distance between the wall at the distal portion 132 and the wall at the proximal portion decreases, and thus the internal volume 130 of the occlusive member 102 also decreases. As the occlusive member 102 collapses, the conduit 116 may be held stationary, advanced distally, and/or retracted proximally.

During and after delivery of the embolic element 230, none or substantially none of the embolic element 230 migrates through the pores of the occlusive member 102 and into the internal volume 130. Said another way, all or substantially all of the embolic element 230 remains at the exterior surface or outside of the occlusive member 102. Compression of the occlusive member with the embolic element 230 provides a real-time "leveling" or "aneurysm-filling indicator" to the physician under single plane imaging methods (such as fluoroscopy) so that the physician can confirm at what point the volume of the aneurysm is completely filled. Additional details regarding devices, systems, and methods for monitoring and/or confirming deployment are described below with reference to FIGS. 4A-5B. It is beneficial to fill as much space in the aneurysm as possible, as leaving voids within the aneurysm sac may cause delayed healing and increased risk of aneurysm recanalization and/or rupture. While the scaffolding provided by the occlusive member 102 across the neck helps thrombosis of blood in any gaps and healing at the neck, the substantial filling of the cavity prevents rupture acutely and does not rely on the neck scaffold (i.e., the occlusive member 102). Confirmation of complete or substantially complete aneurysm filling under single plane imaging cannot be provided by conventional devices.

Once delivery of the embolic element 230 is complete, the conduit 116 may be withdrawn. In some embodiments, the embolic element 230 may fill greater than 40% of the aneurysm sac volume. In some embodiments, the embolic element 230 may fill greater than 50% of the aneurysm sac volume. In some embodiments, the embolic element 230 may fill greater than 60% of the aneurysm sac volume. In some embodiments, the embolic element may fill greater than 65%, 70%, 75%, 80%, 85%, or 90% of the aneurysm sac volume.

Figure 3E:
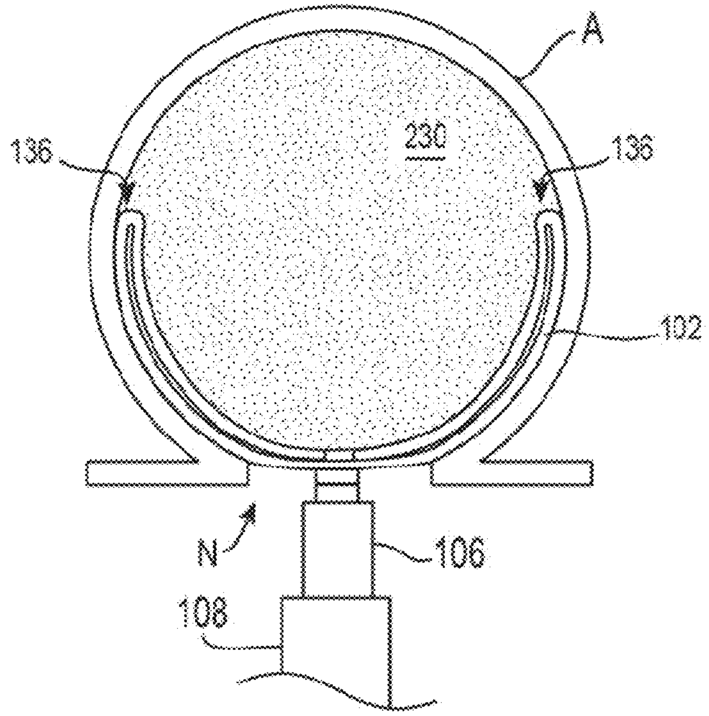
Figure 3F:
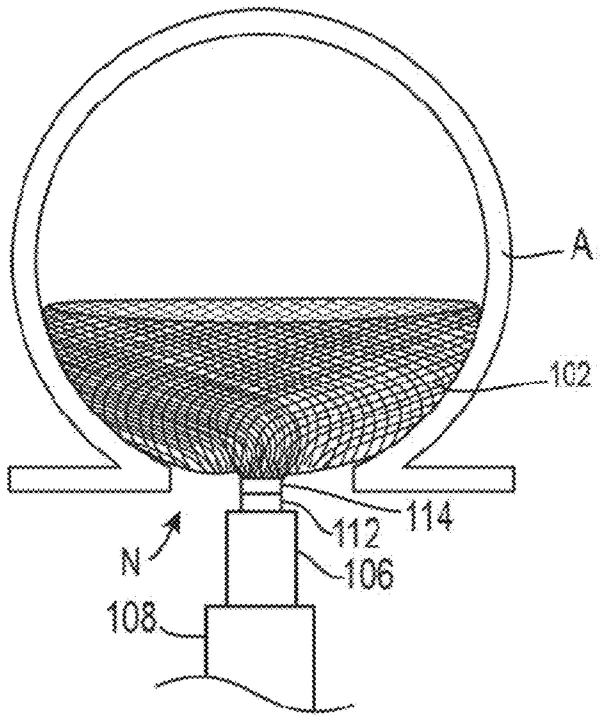

FIG. 3E shows a second expanded state of the occlusive member 102, shown in cross-section, with the embolic element 230 occupying the remaining volume of the aneurysm A. FIG. 3F shows the occlusive member 102 in full with the embolic element 230 removed so the second shape of the occlusive member 102 is visible. As shown, the embolic element 230 may be delivered until the occlusive member 102 is fully-collapsed such that the occlusive member 102 has substantially no internal volume.

In the second expanded state, the occlusive member 102 may form a bowl shape that extends across the neck of the aneurysm A. The wall of the occlusive member 102 at the distal portion may now be positioned in contact with or immediately adjacent the wall of the occlusive member 102 at the proximal portion. The distal wall 132 may be in contact with the proximal wall 134 along all or substantially all of its length. In some embodiments, the distal wall 132 may be in contact with the proximal wall 134 along only a portion of its length, while the remainder of the length of the distal wall 132 is in close proximity—but not in contact with—the proximal wall 134.

Collapse of the occlusive member 102 onto itself, towards the neck N of the aneurysm, may be especially beneficial as it doubles the number of layers across the neck and thus increases occlusion at the neck N. For example, the distal wall 132 collapsing or inverting onto the proximal wall 134 may decrease the porosity of the occlusive member 102 at the neck N. In those embodiments where the occlusive member 102 is a mesh or braided device such that the distal wall 132 has a first porosity and the proximal wall 134 has a second porosity, deformation of the distal wall 132 onto or into close proximity within the proximal wall 134 decreases the effective porosity of the occlusive member 102 over the neck N. The resulting multi-layer structure thus has a lower porosity than the individual first and second porosities. Moreover, the embolic element 230 along the distal wall 132 provides additional occlusion. In some embodiments, the embolic element 230 completely or substantially completely occludes the pores of the adjacent layer or wall of the occlusive member 102 such that blood cannot flow past the embolic element 230 into the aneurysm cavity. It is desirable to occlude as much of the aneurysm as possible, as leaving voids of gaps can allow blood to flow in and/or pool, which may continue to stretch out the walls of aneurysm A. Dilation of the aneurysm A can lead to recanalization and/or herniation of the occlusive member 102 and/or embolic element 230 into the parent vessel and/or may cause the aneurysm A to rupture. Both conditions can be fatal to the patient.

In those embodiments where the wall of the occlusive member 102 comprises an inner and outer layer, the deformed or second shape of the occlusive member 102 forms four layers over the neck N of the aneurysm A In those embodiments where the wall of the occlusive member 102 comprises a single layer, the deformed or second shape of the occlusive member 102 forms two layers over the neck N of the aneurysm A As previously mentioned, the neck coverage provided by the doubled layers provides additional surface area for endothelial cell growth, decreases the porosity of the occlusive member 102 at the neck N (as compared to two layers or one layer), and prevents herniation of the embolic element 230 into the parent vessel. During and after delivery, the embolic element 230 exerts a substantially uniform pressure on the occlusive member 102 towards the neck N of the aneurysm A, thereby pressing the portions of the occlusive member 102 positioned adjacent the neck against the inner surface of the aneurysm wall such that the occlusive member 102 forms a complete and stable seal at the neck N.

Figure 3G:
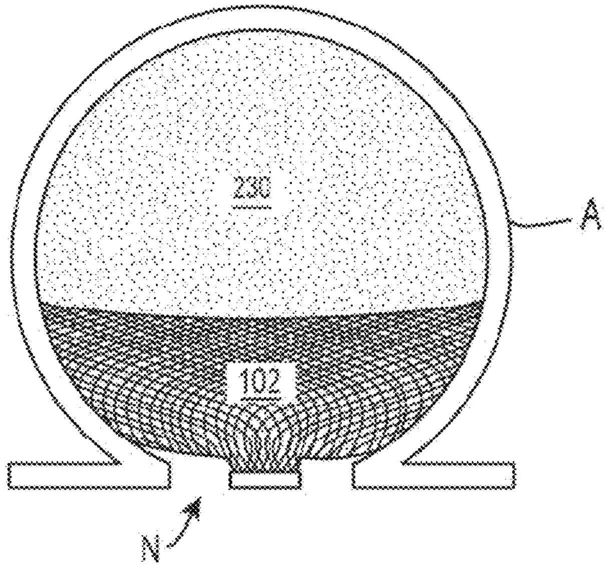

As shown in FIG. 3G, the first coupler 112 may be detached from the second coupler 114 and the elongated member 106 and second elongated shaft 108 may be withdrawn, thereby leaving the occlusive member 102 and embolic element 230 implanted within the aneurysm A.

Over time natural vascular remodeling mechanisms and/or bioabsorption of the embolic element 230 may lead to formation of a thrombus and/or conversion of entrapped thrombus to fibrous tissue within the internal volume of the aneurysm A. These mechanisms also may lead to cell death at a wall of the aneurysm and growth of new endothelial cells between and over the filaments or struts of the occlusive device 102. Eventually, the thrombus and the cells at the wall of the aneurysm may fully degrade, leaving behind a successfully remodeled region of the blood vessel.

In some embodiments, contrast agent can be delivered during advancement of the occlusive member 102 and/or embolic element 230 in the vasculature, deployment of the occlusive member 102 and/or embolic element 230 at the aneurysm A, and/or after deployment of the occlusive member 102 and/or embolic element 230 prior to initiation of withdrawal of the delivery system. The contrast agent can be delivered through the second elongated shaft 108, the conduit 116, or through another catheter or device commonly used to delivery contrast agent. The aneurysm (and devices therein) may be imaged before, during, and/or after injection of the contrast agent, and the images may be compared to confirm a degree of occlusion of the aneurysm.

According to some aspects of the technology, the system 10 may comprise separate first and second elongated shafts (e.g., microcatheters) (not shown), the first dedicated to delivery of the embolic element, and the second dedicated to the delivery of the occlusive member. In example methods of treating an aneurysm, the first elongated shaft may be intravascularly advanced to the aneurysm and through the neck such that that a distal tip of the first elongated shaft is positioned within the aneurysm cavity. In some embodiments, the first elongated shaft may be positioned within the aneurysm cavity such that the distal tip of the shaft is near the dome of the aneurysm.

The second elongated shaft containing the occlusive member (such as occlusive member 102) may be intravascularly advanced to the aneurysm and positioned within the aneurysm cavity adjacent the first elongated shaft. The occlusive member may then be deployed within the aneurysm sac. As the occlusive member is deployed, it pushes the first elongated shaft outwardly towards the side of the aneurysm, and when fully deployed the occlusive member holds or "jails" the first elongated shaft between an outer surface of the occlusive member and the inner surface of the aneurysm wall.

The embolic element (such as embolic element 230) may then be delivered through the first elongated shaft to a position between the inner surface of the aneurysm wall and the outer surface of the occlusive member. For this reason, it may be beneficial to initially position the distal tip of the first elongated shaft near the dome (or more distal surface) of the aneurysm wall. This way, the "jailed" first elongated shaft will be secured by the occlusive member such that the embolic element gradually fills the open space in the aneurysm sac between the dome and the occlusive member. As described elsewhere herein, the filling of the embolic element pushes and compresses the occlusive member against the tissue surrounding the aneurysm neck as the space in the sac above the occlusive member is being filled from the dome to the neck. Also as described elsewhere herein, the compression of the occlusive member with the embolic element provides a "leveling or aneurysm filling indicator" which is not provided by conventional single plane imaging methods. The filling of the embolic element may complete, for example, when it occupies about 50-80% of the volume of the aneurysm.

III. Selected Devices, Systems, and Methods for Monitoring Deployment

Proper deployment of the embolic element 230 and the occlusive member 102 can be monitored and/or confirmed using one or more medical imaging techniques, such as fluoroscopy. FIGS. 4A-5B illustrate examples of various types of fluoroscopic images that may be employed by a physician at different stages of deployment to monitor the position of the occlusive member 102 within the aneurysm A, monitor the degree of filling of the aneurysm A with the embolic element 230, and/or confirm a degree of occlusion of the aneurysm A by the deployed system. As described in greater detail below, the devices and systems of the present technology may be configured to provide unique visual indicators that provide confirmation to the physician via one or more medical imaging techniques regarding a degree of occlusion of the aneurysm. As described in greater detail below, the visual indicators may include a particular change in shape of all or a portion of the occlusive member 102, a particular change in relative position of one or more radiopaque markers on the occlusive member 102 and/or delivery system (such as the conduit 116), a particular change in shape of the embolic element 230, and others.

Although the following discussion is made with reference to the two-dimensional images shown in FIGS. 4A-5B, the systems and methods of the present technology can be employed with three-dimensional imaging techniques. Moreover, FIGS. 4A-5B represent a two-dimensional image in which only a slice of the aneurysm (and devices therein) is visible. While in some cases the inner and outer layers of the occlusive member 102 (when such are present) may be distinguishable from one another in the radiographic image, in the present example the layers appear as one thick layer. As used herein, "proper deployment" or "successful deployment" may refer to (a) complete (e.g., greater than 80%) or substantially complete (e.g., greater than 50%) filling of the aneurysm A with the embolic element 230, (b) complete or substantially complete inversion or collapse of the occlusive member 102 onto itself over the neck N of the aneurysm A, (c) or both.

Figure 4A:
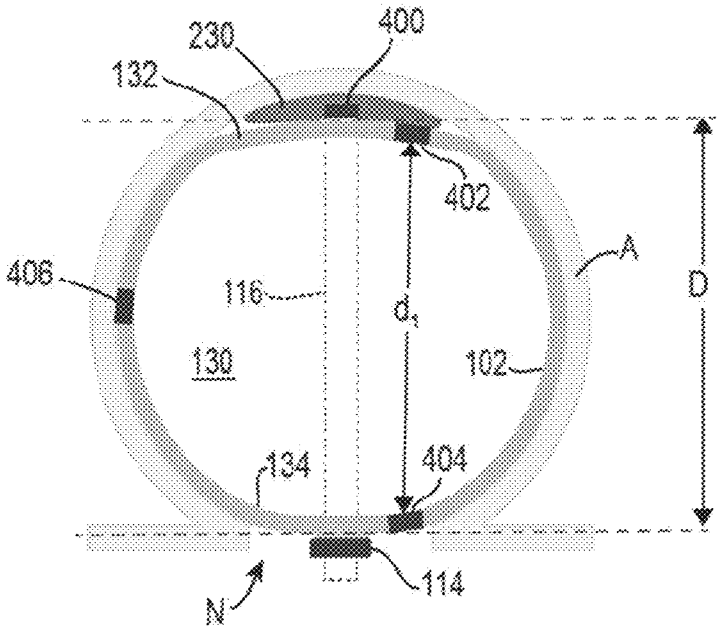
FIGS. 4A-5B show various types of images that may be employed to confirm and/or monitor deployment of the treatment system of the present technology.
Figure 4B:
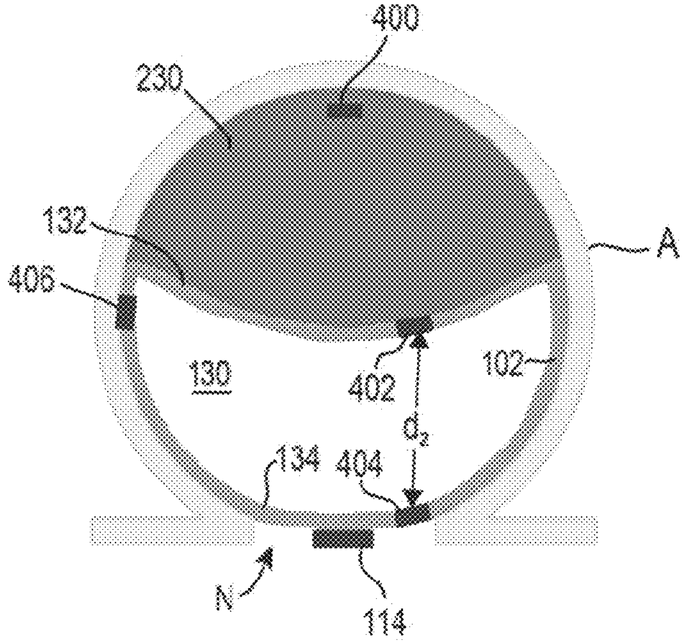
Figure 4C:
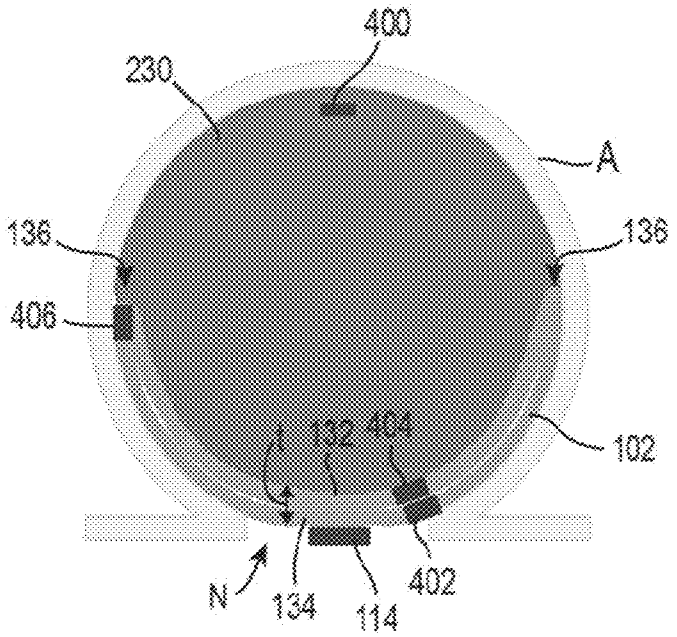

The occlusive member 102 may include one or more radiopaque markers, such as markers 402, 404, 406, and 114 (referred to collectively as "markers 401") shown in FIGS. 4A-4C. The markers 401 may be disposed about the occlusive member 102 in a specific spatial arrangement such that relative movement of the markers is indicative of a degree of stage of deployment of the occlusive member 102 and/or embolic element 230. The markers 401 may be positioned at any location along the occlusive member 102. For example, the occlusive member 102 may include one or more radiopaque markers 402 at or along its distal wall 132 (only one shown for ease of illustration), one or more radiopaque markers 404 at or along its proximal wall 134 (only one shown for ease of illustration), and one or more radiopaque markers 406 at or along the intermediate portion of the wall (only one shown for ease of illustration). Moreover, the coupler 114 of the occlusive member 102 may be radiopaque. The markers 401 may be positioned at one, some, or all of the layers of the occlusive member 102 (at least in those embodiments where the occlusive member 102 includes multiple layers). In some embodiments, the individual markers 401 may comprise a radiopaque band or clip coupled to the one or more struts, filaments, wires, etc. of the occlusive member 102. In some embodiments, the individual markers 401 may comprise a radiopaque material coated on or otherwise incorporated into the wall of the occlusive member 102. The individual markers 401 may have the same or different shapes, lengths, and/or profiles.

In some embodiments, in addition to or instead of having one or more markers 401, the occlusive member 102 itself may be partially or completely formed of a radiopaque material, such as one or more radiopaque wires. In the example depicted in FIGS. 4A-4C, the occlusive member 102 is formed of a radiopaque material and also includes radiopaque markers 402, 404, 406. The occlusive member 102 is formed of a plurality of drawn-filled tube ("DFT") wires, which comprise a core formed of a radiopaque material (such as platinum) surrounded by an outer non-radiopaque material (at least relative to the core material). The markers 402, 404, 406 are completely formed of a radiopaque material and thus have a higher density of radiopaque material. As such, the markers 402, 404, 406 appear darker than the occlusive member 102 in the images. In some embodiments, the occlusive member 102 may have a radiopacity that is different than the radiopacity of one or more of the markers 402, 404, 406 such that the wall of the occlusive member 102 wall and the marker(s) 406 can be distinguished from one another on the radiographic image. The wall of the occlusive member 102 may be more or less radiopaque than one or more of the markers 402, 404, 406.

In some embodiments, one or more components of the delivery system may include one or more radiopaque markers. For example, the conduit 116 may include one or more radiopaque markers positioned along its length. In the embodiment depicted in FIGS. 4A-4C, the conduit 116 may include a radiopaque marker 400 positioned at or near its distal end. The conduit 116 may have one or more additional markers (not shown) positioned along its length, such as along the length of the conduit 116 that extends through the interior volume 130 of the occlusive member 102.

As shown in FIG. 4A, when the occlusive member 102 is first deployed (e.g., allowed to self-expand) within the aneurysm, the radiopaque marker(s) 402, 404, 406 of the occlusive member 102 will be in a first position relative to one another, and to the radiopaque marker(s) of the conduit 116. By way of example, markers 402 and 404 are separated by a first distance $d_1$ when the occlusive member 102 is first deployed. As the embolic element 230 is conveyed through the conduit 116 and into the aneurysm sac, the occlusive member 102 may deform as described previously with respect to FIGS. 3A-3G. This deformation can cause the radiopaque marker(s) 401 carried by the occlusive member 102 to move to a second position relative to one another. For example, the physician may confirm progression of deployment by observing that markers 402 and 404 are now separated by a distance $d_2$. The radiopaque marker(s) 401 may also move relative to the radiopaque marker(s) 400 of the conduit 116, which may remain in the same or substantially the same place within the aneurysm. By comparing an image of the radiopaque markers 400 and/or 401 in the first relative positions and an image of the radiopaque markers 400 and/or 401 in the second relative positions, a clinician can visually confirm that the embolic element 230 has filled a certain percentage of the aneurysm A.

For example, according to some aspects of the technology, confirmation of sufficient filling of the aneurysm (i.e., 50% or greater) may be indicated by one or more distal wall markers 402 moving into close proximity to one or more proximal wall markers 404 and/or touching one or more proximal wall markers 404. Because the embolic element 230 applies a generally uniform pressure across the distal wall 132 and pushes downwardly towards the neck N as it fills in the space between the occlusive member 102 and the aneurysm wall, the movement of one or more distal wall markers 402 to a position adjacent a proximal wall marker 404 indicates to a physician that the aneurysm A is substantially filled (e.g., 50% or greater) with the embolic element 230. This relative positioning also indicates that the distal wall 132 is now providing additional occlusion at the neck N of the aneurysm and that the occlusive member 102 is in its second expanded shape. In some embodiments, the coupler 114 may be used as the proximal indicator instead of or in addition to the one or more proximal markers 404.

In some embodiments, confirmation of sufficient filling of the aneurysm (i.e., 50% or greater) may be indicated by one or more distal wall markers 402 moving away from the conduit marker 400 (or marker affixed to another component of the delivery system) by a predetermined distance. For example, when the occlusive member 102 is in the first expanded state or shape (FIG. 4A) the distal wall marker 402 may be adjacent the conduit marker 400. In the second expanded state or shape (FIG. 4C), the distal wall marker 402 may be separated from the conduit marker 400 by a distance that is generally equivalent to a diameter D of the occlusive member 102 in its expanded state while initially positioned in the aneurysm A. As explained above, such relative positioning of one or more distal wall markers 402 and conduit marker 400 indicates to a physician that the aneurysm A is substantially filled (e.g., 50% or greater) with the embolic element 230. This relative positioning also indicates that the distal wall 132 is now providing additional occlusion at the neck N of the aneurysm and that the occlusive member 102 is in its second expanded shape.

In some embodiments, one or more intermediate markers 406 may be used to confirm and/or monitor deployment. For example, one or more intermediate markers 406 may be positioned at or near a desired inversion plane of the occlusive member 102. In the present example using a generally spherical occlusive member 102 that deforms to assume a bowl shape, the inversion plane is at or near a midline of the occlusive member 102 in its expanded state. This is because, in a fully inverted state, the distal half of the occlusive member 102 will lie within/conform to the proximal half of the occlusive member 102 (as shown in FIG. 4C). As such, the midline of the occlusive member 102 is the desired plane of inversion. The occlusive member 102 may be radiopaque (as shown in FIGS. 4A-4C), but to a lesser extent than the intermediate marker(s) 406 such that the occlusive member 102 wall and the marker(s) 406 can be distinguished from one another on the radiographic image. As such, an image showing the top edge 136 (FIG. 4C) of the occlusive member 102 adjacent or at the intermediate marker(s) 406 may indicate that the aneurysm A is substantially filled (e.g., 50% or greater) with the embolic element 230. This relative positioning also indicates that the distal wall 132 is now providing additional occlusion at the neck N of the aneurysm and that the occlusive member 102 is in its second expanded shape.

The change in shape of the occlusive member 102 and/or change in position of different portions of the occlusive member 102 relatively to one another may also indicate proper deployment. As previously discussed, the occlusive member 102 assumes a first expanded shape when initially deployed and has a second expanded shape after deformation by the embolic element 230. In several embodiments, the second expanded shape represents a partially or completely inverted from of the first expanded shape, which can be confirmed on the radiographic image by observing the changing outline of the occlusive member 102. For instance, in the present example where the occlusive member 102 has a first expanded shape that is generally spherical, an image showing a C-shape (as shown in FIG. 4C) may indicate that the desired filling and/or deployment is complete. In a three-dimensional image, the second expanded shape may have a bowl shape. In some embodiments, confirmation of complete or substantially complete deployment may be indicated by the distal wall 500 being within a predetermined distance of the proximal wall 502.

In some embodiments, proper deployment may be confirmed by observing a distance between the inverted wall (here, distal wall 132) and the relatively stationary wall (here, proximal wall 134). As shown in FIG. 4C, when the distal wall 132 collapses down onto or near the proximal wall 134, the occlusive member 102 presents on the image as having twice the thickness at the proximal portion. Moreover, as the occlusive member 102 inverts, the density of the radiopaque material doubles, and thus the doubled-over portions of the occlusive member 102 appear darker on the image.

Figure 5A:
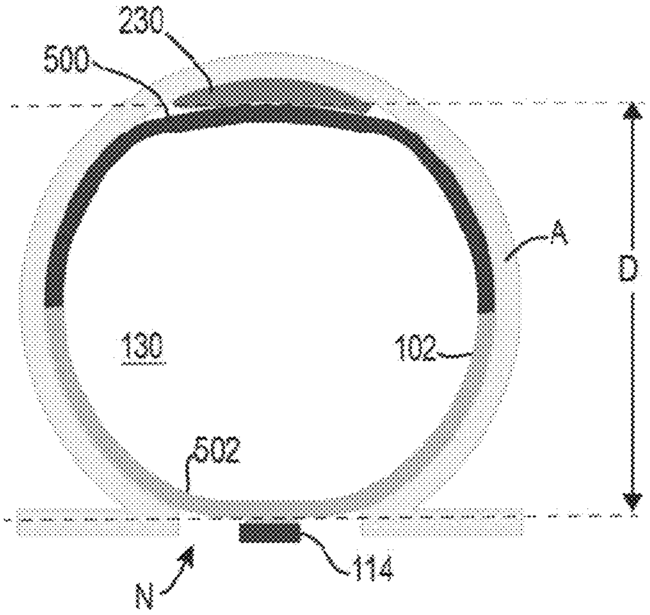
Figure 5B:
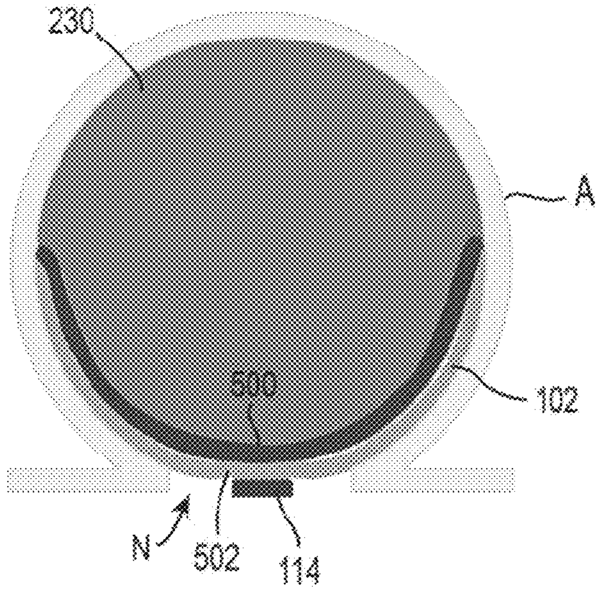

As shown in FIGS. 5A and 5B, in some embodiments, certain portions of the occlusive member 102 may be coated with a radiopaque material such that change in shape or orientation of those portions indicates a desired position of the occlusive member 102. For example, as shown in FIG. 5A, a distal-most half 500 of the occlusive member 102 may be coated with a radiopaque material while a proximal-most half 502 may not be coated or may otherwise be less radiopaque than the distal half 500. As such, confirmation of complete or substantially complete deployment may be indicated by the more radiopaque distal wall 500 being adjacent the proximal wall 502. For example, confirmation of complete or substantially complete deployment may be indicated by the distal wall 500 being within a predetermined distance of the proximal wall 502. Confirmation may also be gleaned from the distal wall 500 changing in shape from flat or convex (towards the dome) of the aneurysm A to concave.

A shape of the embolic element 230 may also provide an indication of deployment progress. For example, the shape of the lower (closer to the neck N) perimeter of the aneurysm A can be indicative of a degree of filling of the aneurysm with the embolic element 230 and/or degree of deformation of the occlusive member 102. As most aneurysms have a generally spherical or globular shape, a lower boundary of the embolic element 230 may have a decreasing radius of curvature as more is injected and more of the occlusive member 102 inverts. For example, in FIG. 4B, when the aneurysm A is partially filled with the embolic element 230 and the occlusive member 102 is only partially collapsed or inverted, the distal wall 132 has a first radius of curvature. In FIG. 4C, when the aneurysm A is substantially completely or completely filled, the distal wall 132 has a radius of curvature less than the radius of curvature of the distal wall 132 in the partially deformed state.

Additionally or alternatively, the degree of deployment of the occlusive member 102 and/or degree of filling of the aneurysm A can be further determined by injecting contrast into the parent blood vessel and imaging the aneurysm to determine how much of the contrast enters the aneurysm cavity. The shape of the The devices, systems, and methods of the present technology may be particularly beneficial over conventional devices for two-dimensional imaging. In two-dimensional imaging (such as fluoroscopy), the image may reflect only a slice or elevational view of the aneurysm (and device or substance therein). As such, any voids or gaps in filling may not be apparent in the slice because the image slice does not transect the void within the aneurysm A, or the cross-section or elevational view of the stagnated area may take on different shapes depending on how the image is observed. A physician may have to take a plurality of images to determine a general amount of filling in the aneurysm. In contrast, the occlusive members 102 of the present technology have a unique shape that dynamically adjusts to the introduction of an embolic element 230 in a predictable, measurable way that indicates a degree of filling of the embolic element 230 in a single two-dimensional radiographic image.

The devices, systems, and methods disclosed herein include confirming and/or observing various stages of deployment of the system in an aneurysm, including complete or substantially complete deployment, using one, some, or all of the methods disclosed above.

IV. Examples of Occlusive Members

Intrasaccular treatment of saccular aneurysms having a certain morphology (such as a wide-necked aneurysm) often requires the occlusive device to be oversized relative to the aneurysm to be treated to provide the radial force necessary for neck protection and stability. In several of the foregoing embodiments, the occlusive member has a substantially spherical first expanded state (see, for example, FIG. 3A). When oversized and implanted, some of these occlusive members elongate and cause the occlusive member to protrude into the parent vessel. To address this challenge and avoid or reduce elongation of the occlusive member, in some embodiments of the present technology the occlusive member is configured to assume a semi-collapsed shape (similar to the hemispherical shape shown in FIG. 3C) when initially deployed. However, occasionally these hemispherical occlusive members elongate during or after deployment such that the distal portion 132 of the occlusive member wall bows distally in the first expanded state (rather than being generally flat or bowing proximally towards the proximal wall 134), before introduction of the embolic element. In such instances, the elongated shape makes subsequent inversion of the occlusive member by delivery of the embolic element (as discussed herein) particularly challenging.

Several embodiments of the occlusive members of the present technology are configured to address the foregoing challenges. Several of such embodiments, for example, are described below with respect to FIGS. 6A-15B. The occlusive members detailed herein allow for sufficient oversizing without treatment-prohibitive elongation, obviate the need for device inversion when the embolic element is delivered, reduce or eliminate protrusion of the occlusive member into the parent vessel, and provide a good fit to the contour of the aneurysm neck.

Figure 6A:
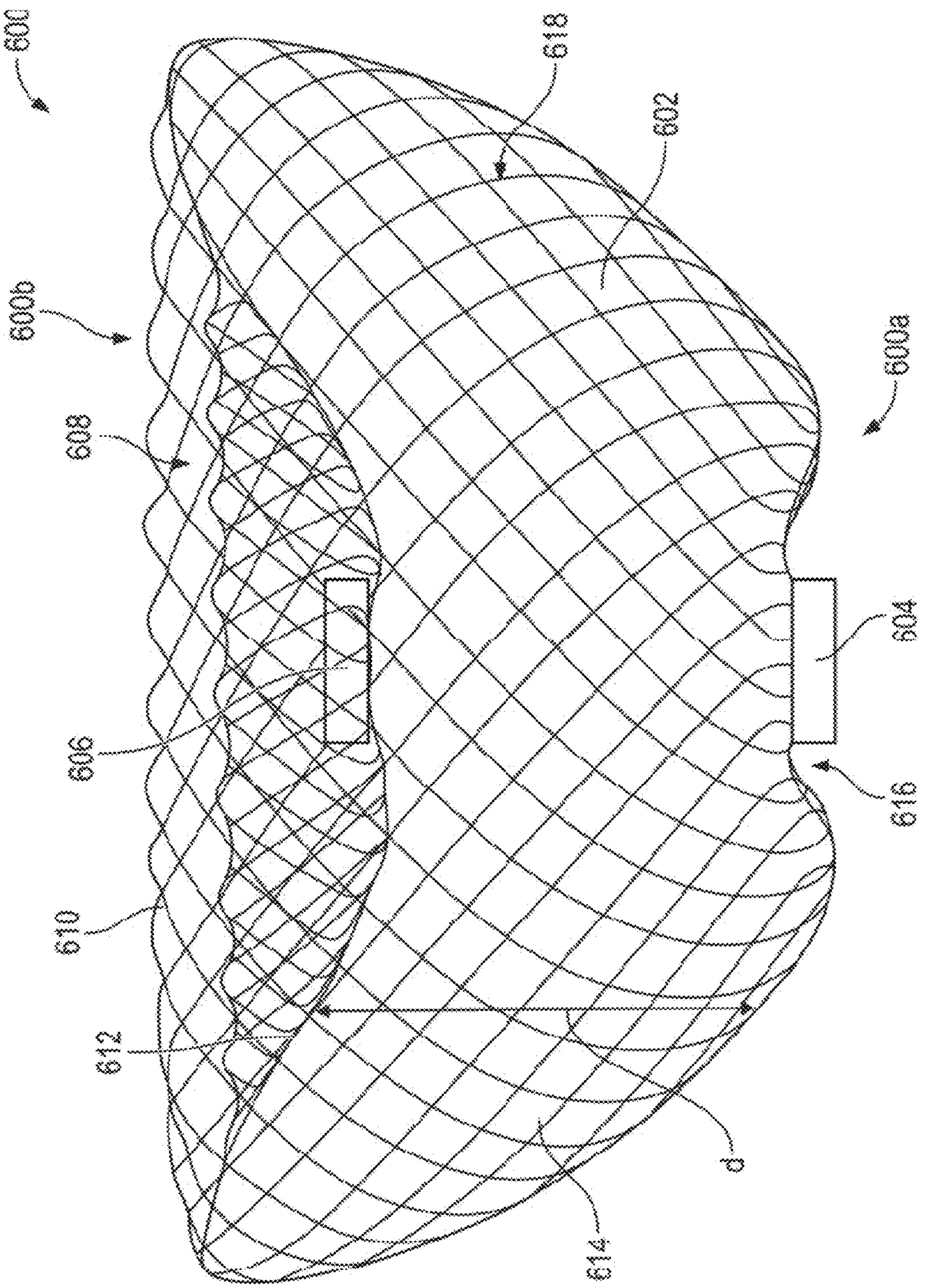
FIG. 6A is a side view of an occlusive member configured in accordance with several embodiments of the present technology.
Figure 6B:
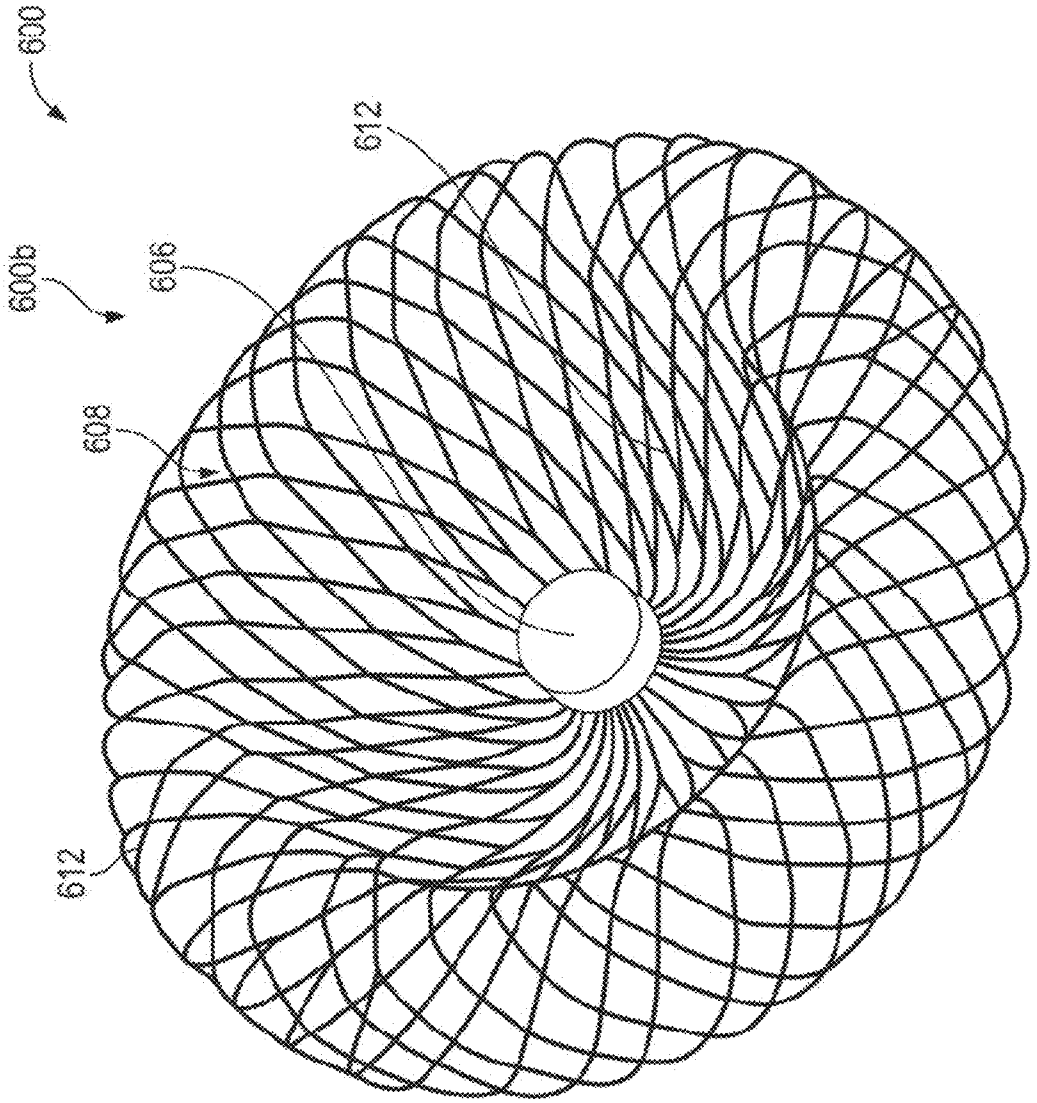
FIGS. 6B and 6C are isometric and cross-sectional views, respectively, of the occlusive member shown in FIG. 6A.
Figure 6C:
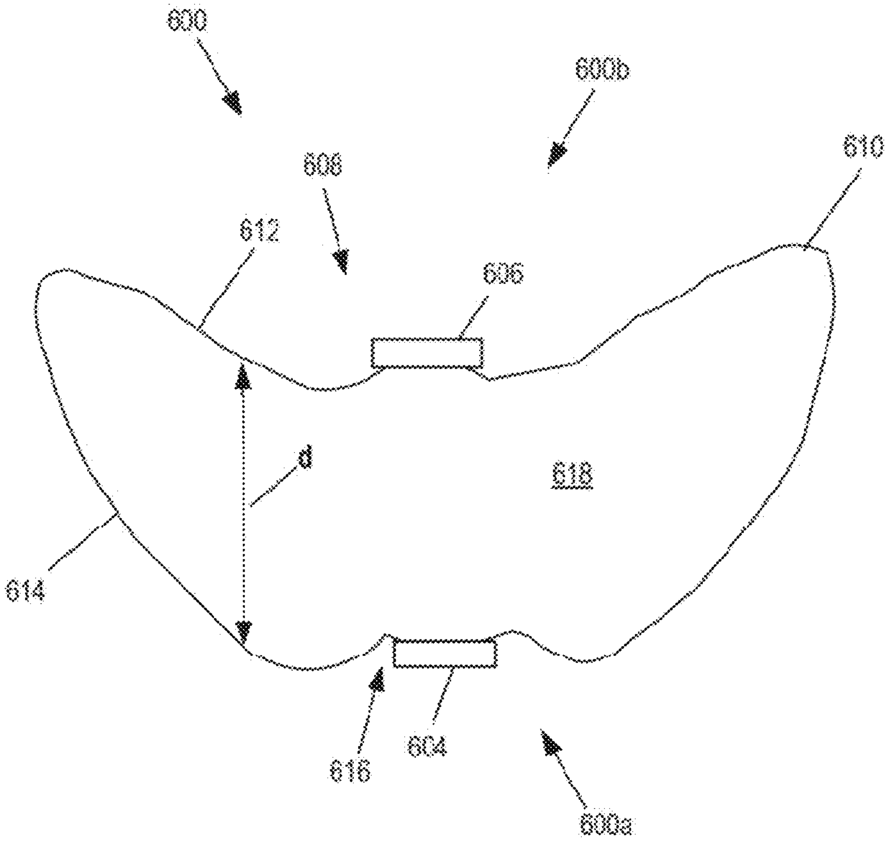

FIG. 6A is a slightly-angled side view of an occlusive member 600 configured in accordance with several embodiments of the present technology. FIGS. 6B and 6C are isometric and cross-sectional views, respectively, of the occlusive member 600. Referring to FIGS. 6A-6C together, the occlusive member 600 may comprise a mesh have a proximal portion 600*a* configured to be positioned over a neck of the aneurysm, a distal portion 600*b*, a proximal coupler 604, and a distal coupler 606. In some embodiments, the mesh is biased towards a predetermined shape when the mesh is in an expanded, unconstrained state. The mesh can be formed of a wall surrounding an interior region 618 and comprising a first portion 614, a second portion 612, and an annular ridge 610. The first portion 614 and the second portion 612 may be separated by a distance d that increases towards the central longitudinal axis of the occlusive member 600. In some embodiments, the distance d may be generally constant or may decrease towards the central longitudinal axis of the device. The first portion 614 of the wall can extend between the proximal coupler 604 and the ridge 610, and the second portion 612 of the wall can extend between the ridge 610 and the distal coupler 606.

In contrast to the occlusive members disclosed herein having a distal wall that bows outwardly away from the interior region in the first expanded state (see, for example, distal wall 132 in FIG. 1C), or is substantially flat in the first expanded state, the second portion 612 of the occlusive member 600 bows inwardly towards the interior portion 618 in the first expanded state, thereby forming a cavity 608 at the distal portion 600*b* of the occlusive member 600. The cavity 608, for example, can be bound by the second portion 612 of the wall and a plane lying on ridge 610. As shown in FIGS. 6A-6C, all or a portion of the distal coupler 606 may thus be positioned within the cavity 608, below the plane defined by the ridge 610. In some embodiments, the occlusive member 600 and/or mesh includes a recessed portion 616 at the proximal portion 600*a* that surround all or a portion of the proximal coupler 604. In some embodiments, the occlusive member 600 and/or mesh does not include a recessed portion 616 at the proximal portion 600*a*.

Because the second portion 612 bows proximally, the occlusive member 600 is less likely to elongate when deployed in the aneurysm and/or elongates less (as compared to the occlusive members with an outward bow or substantially flat distal wall). In addition, because the bowed second portion 612 mimics the semi-collapsed states discussed herein (for example with reference to FIGS. 1A-5B), the occlusive member 600 does not have to rely on the proximally-directed forces applied by the embolic element to cause inversion of the occlusive member 600. Instead, the embolic element can fill the space between the second portion 612 and the aneurysm wall with or without causing the second portion 612 to move towards the first portion 614.

In some embodiments, for example as shown in FIGS. 6A-6C, the occlusive member 600 and/or mesh is formed of a plurality of braided filaments 602, each having first and second ends and a length measured therebetween. In contrast to the occlusive members disclosed herein in which the first and second ends of the filaments are secured relative to one another at the same location (such as the proximal coupler), the first and second ends of the filaments 602 forming occlusive member 600 are secured relative to one another at separate couplers. For example, the first ends of the filaments 602 can be secured relative to one another at the proximal coupler 604, and the second ends of the filaments 602 can be secured relative to one another at the distal coupler 606. As such, the second ends of the filaments 602 terminate within the cavity 608, below the plane defined by the ridge 610. The resulting mesh structure thus has a "single layer" delivery configuration in which the distal coupler 606 is longitudinally spaced apart from the proximal coupler 604 by a distance greater than the longitudinal distance between the distal and proximal couplers 606, 604 when the occlusive member 600 is in an expanded state. As such, when the occlusive member 600 is in a delivery configuration, the occlusive member 600 is elongated such that no portion or substantially no portion of any filament 602 radially overlaps another portion of the same filament 602. When the occlusive member 602 is released from the delivery sheath, the proximal and distal couplers 604, 606 move longitudinally closer together, thus creating the bowed second portion 612 and cavity 608.

The single layer delivery configuration of occlusive member 600 (as well as occlusive member 700, occlusive member 800, occlusive member 900, etc.) advantageously allows for a mesh having a lower delivery profile, and thus enables delivery of the occlusive member through smaller diameter delivery catheters as compared to occlusive members having double layer delivery configurations (for example, occlusive member 102, occlusive member 1000, occlusive member 1100, occlusive member 1300, etc.) or quadruple layer delivery configurations (for example, occlusive member 1400, occlusive member 1500, etc.).

In some embodiments, the second portion 612 of the wall may have a contour and/or shape that substantially follows the contour and/or shape of the first portion 614 of the wall, or the first and second portions 612, 614 may have different contours and/or shapes. In these and other embodiments, a radius of curvature of all or a portion of the second portion 612 of the wall may be different than the radius of curvature of all or a portion of the first portion 614 of the wall. In these and other embodiments, the second portion 612 of the wall may have a radius of curvature that is greater than, less than, or substantially equal to the radius of curvature of the first portion 614 of the wall. The second portion 612 of occlusive member 600 can have a substantially constant slope along its length (i.e., between the ridge 610 and the distal coupler 606), or all or a portion of the length may be convex towards the aneurysm wall (while still maintaining cavity 608), and/or all or a portion of the length may be concave towards the aneurysm wall.

The mesh of occlusive member 600 may be formed of metal wires, polymer wires, or both, and the wires may comprise a resilient material and/or a material having shape memory and/or superelastic properties. The mesh may be formed of 24, 32, 36, 48, 64, 72, 96, 128, or 144 filaments. The mesh may be formed of a range of filament or wire sizes, such as wires having a diameter of from about 0.0004 inches to about 0.0020 inches, or of from about 0.0009 inches to about 0.0012 inches. In some embodiments, each of the wires or filaments have a diameter of about 0.0004 inches, about 0.0005 inches, about 0.0006 inches, about 0.0007 inches, about 0.0008 inches, about 0.0009 inches, about 0.001 inches, about 0.0011 inches, about 0.0012 inches, about 0.0013 inches, about 0.0014 inches, about 0.0015 inches, about 0.0016 inches, about 0.0017 inches, about 0.0018 inches, about 0.0019 inches, or about 0.0020 inches. In some embodiments, all of the filaments of the braided mesh may have the same diameter. For example, in some embodiments, all of the filaments have a diameter of about 0.001 inches. In some embodiments, some of the filaments may have different cross-sectional diameters. For example, some of the filaments may have a slightly thicker diameter to impart additional strength to the braided layers. In some embodiments, some of the filaments can have a diameter of about 0.001 inches, and some of the filaments can have a diameter of greater than 0.001 inches. The thicker filaments may impart greater strength to the braid without significantly increasing the device delivery profile, with the thinner wires offering some strength while filling-out the braid matrix density.

Figure 7:
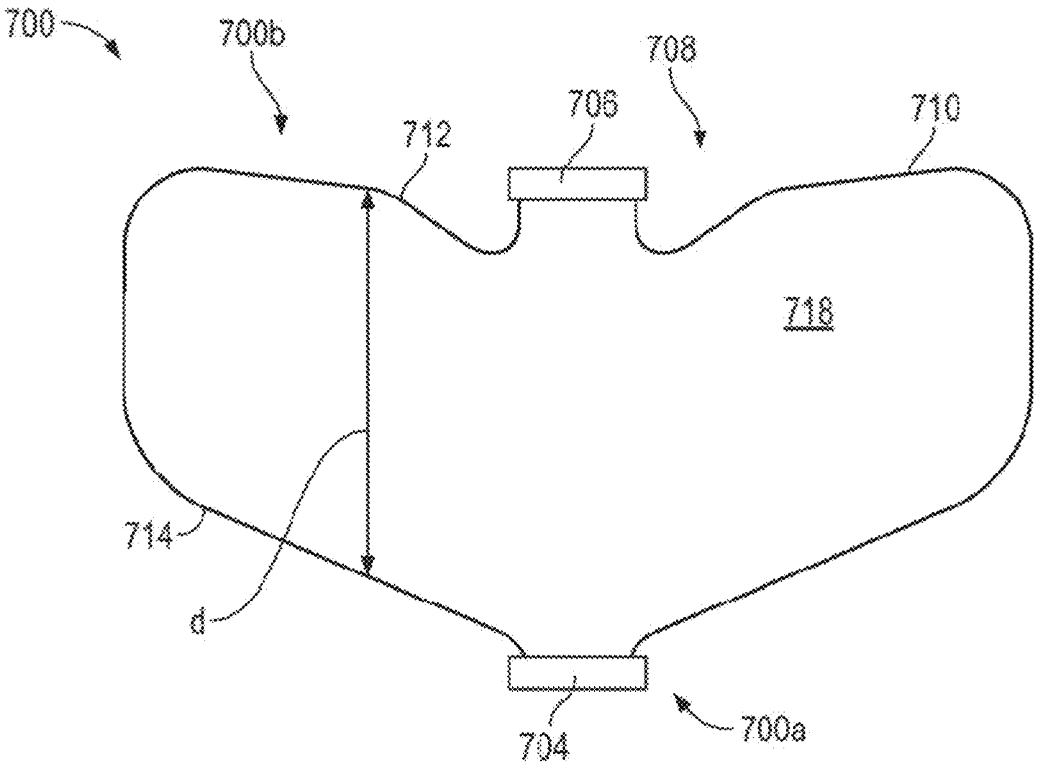
FIGS. 7 and 8 are cross-sectional views of different occlusive members configured in accordance with several embodiments of the present technology.
Figure 8:
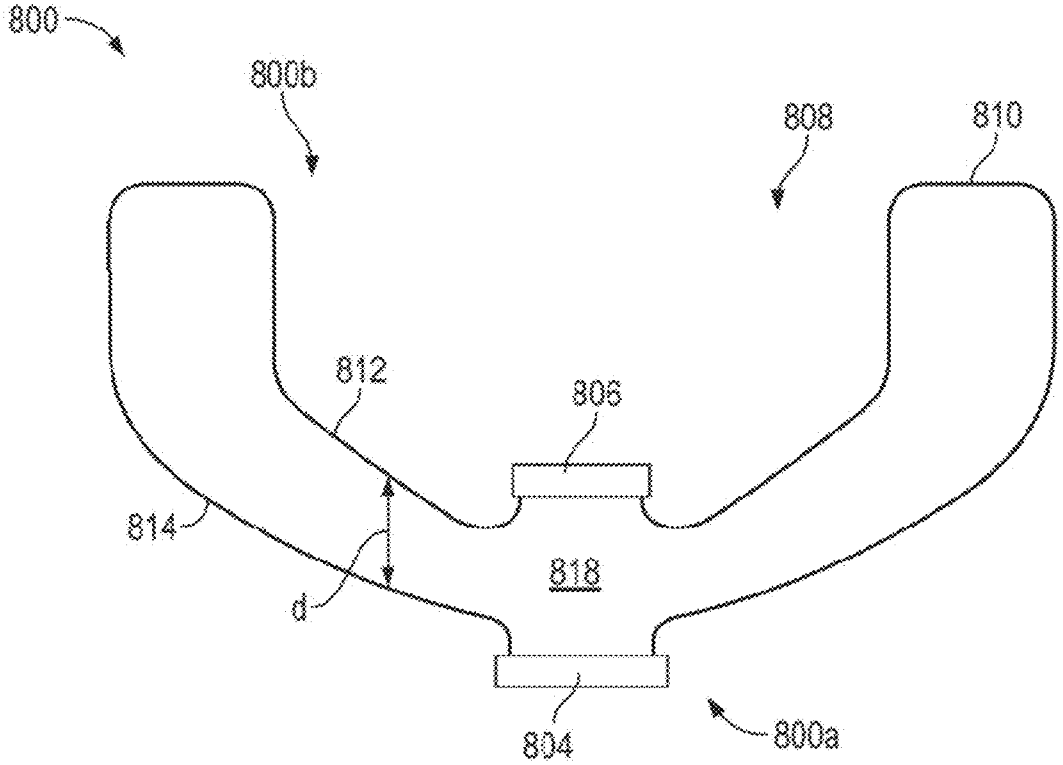

FIGS. 7 and 8 are cross-sectional views of different occlusive members 700, 800 configured in accordance with several embodiments of the present technology. Several features of the occlusive member 700 shown in FIG. 7 can be generally similar to the features of occlusive member 600. The occlusive member 700 shown in FIG. 7, however, has a second portion 712 that includes a region that is concave towards the interior region 718 along most of its length, and has a wider ridge 710 than ridge 610. Several features of the occlusive member 800 shown in FIG. 8 can be generally similar to the features of occlusive member 600. The occlusive member 800 of FIG. 8, however, has less separation between the first and second portions 812, 814, and a generally constant distance d between the first and second portions 812, 814. As a result, the occlusive member 800 has a bowl-shaped configuration in the first expanded state.

Figure 9A:
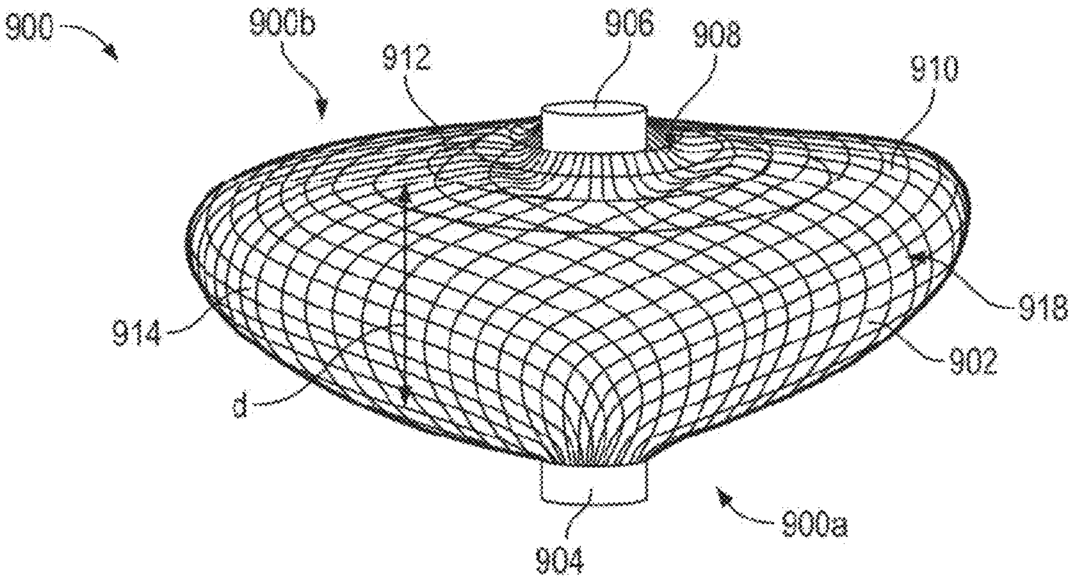
FIG. 9A is a side view of an occlusive member configured in accordance with several embodiments of the present technology.
Figure 9B:
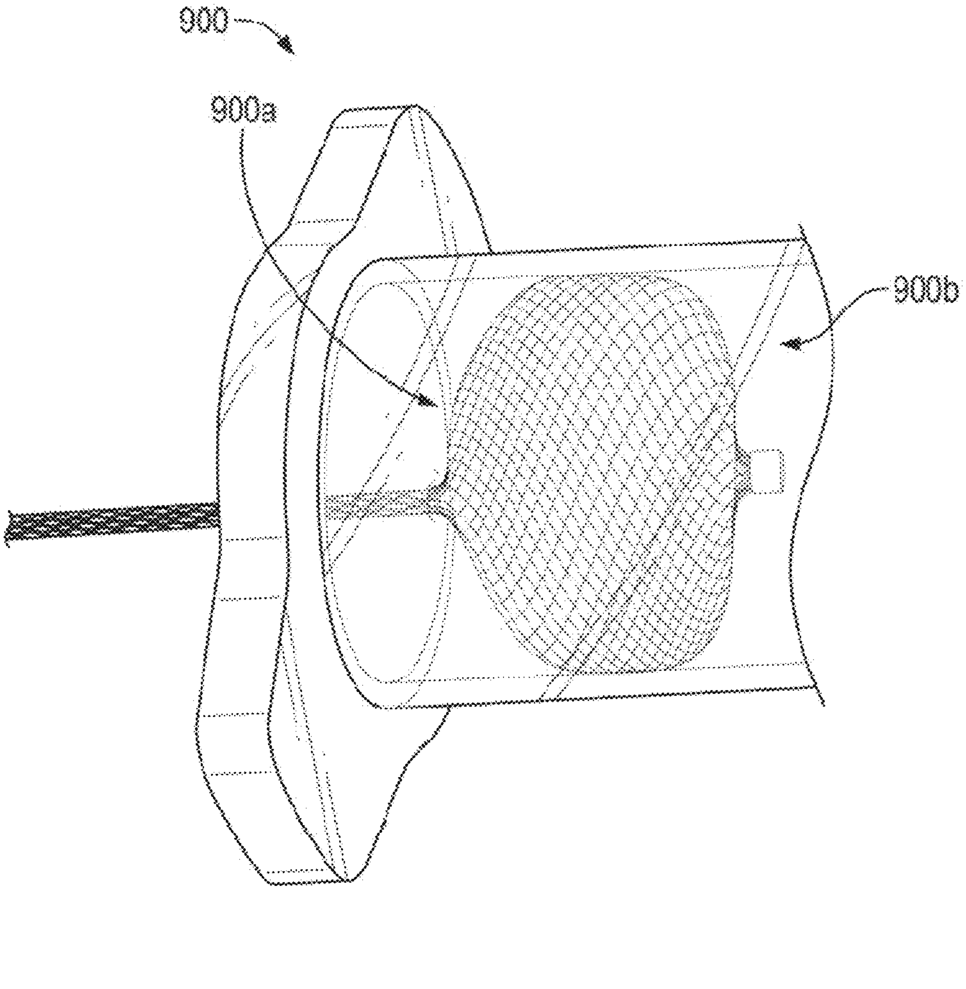
FIG. 9B is a side view of the occlusive member of FIG. 9A shown deployed in a transparent tube.

FIG. 9A is a side view of an occlusive member 900 configured in accordance with several embodiments of the present technology. Several features of the occlusive member 900 shown in FIG. 9A can be generally similar to the features of occlusive member 600. In FIG. 9A, the occlusive member 900 has a cavity 908 that is fairly shallow. FIG. 9B is a side view of the occlusive member of FIG. 9A shown in an elongated, expanded state in a transparent tube. As shown in FIG. 9B, the second portion 912 extends distally such that the distal portion 900*b* is farther from the proximal portion 900*a* than when the occlusive member 900 is in the first expanded state (FIG. 9A).

It will be appreciated that occlusive members of the present technology having a single layer delivery configuration can have different shapes, sizes, and configurations and are not limited to those embodiments depicted in the drawings. Moreover, an elongate shaft for delivery of the embolic element may be positioned through one or both of the proximal and distal couplers.

Figure 10A:
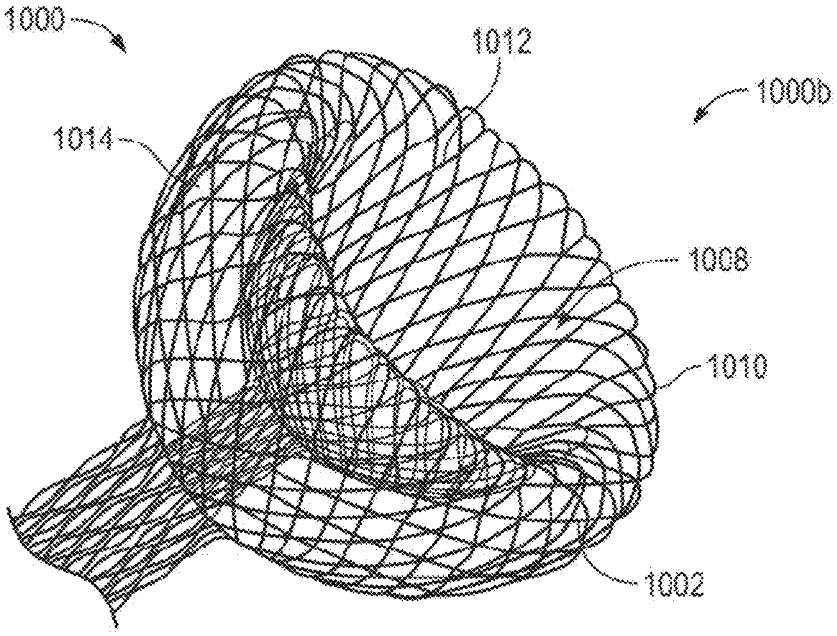
FIGS. 10A, 10B and 10C are isometric, cross-sectional, and side views, respectively, of an occlusive member configured in accordance with several embodiments of the present technology.
Figure 10B:
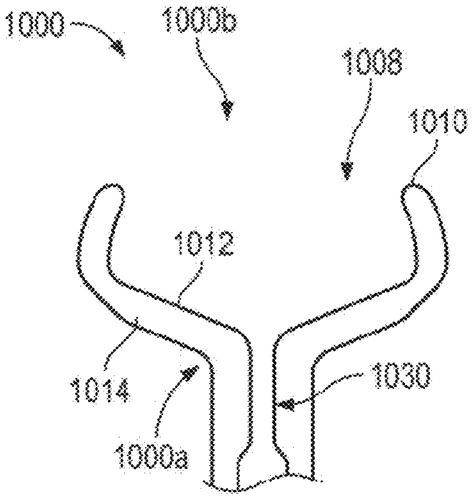
Figure 10C:
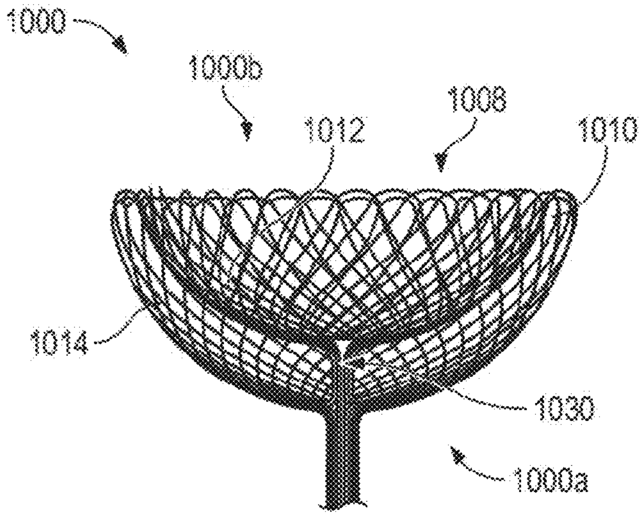

FIGS. 10A, 10B and 10C are isometric, cross-sectional, and side views, respectively, of an occlusive member 1000 configured in accordance with several embodiments of the present technology. Referring to FIGS. 10A-10C together, the occlusive member 1000 may comprise a mesh have a proximal portion 1000*a* configured to be positioned over a neck of the aneurysm, a distal portion 1000*b*, and a proximal coupler (not depicted in FIGS. 10A-10C) . . . . In some embodiments, the mesh is biased towards a predetermined shape when the mesh is in an expanded, unconstrained state. The mesh can be formed of a wall surrounding an interior region and comprising a first portion 1014, a second portion 1012, and an annular ridge 1010. The first portion 1014 and the second portion 1012 may be separated by a distance d. In some embodiments, the distance d may be generally constant or slightly increase towards the central longitudinal axis of the device. The first portion 1014 of the wall can extend between the proximal coupler and the ridge 1010, and the second portion 1012 of the wall can extend between the ridge 1010 and the proximal coupler.

In contrast to the occlusive members disclosed herein having a distal wall that bows outwardly away from the interior region in the first expanded state (see, for example, distal wall 132 in FIG. 1C), or is substantially flat in the first expanded state, the second portion 1012 of the occlusive member 1000 bows inwardly towards the interior portion in the first expanded state, thereby forming a cavity 1008 at the distal portion 1000*b* of the occlusive member 1000, thereby forming a bowl or chalice shape. The cavity 1008, for example, can be bound by the second portion 1012 of the wall and a plane lying on ridge 1010.

Because the second portion 1012 is biased proximally, the occlusive member 1000 is less likely to elongate when deployed in the aneurysm and/or elongates less (as compared to the occlusive members with an outward bow or substantially flat distal wall). In addition, because the bowed second portion 1012 mimics the semi-collapsed states discussed herein (for example with reference to FIGS. 1A-5B), the occlusive member 600 does not have to rely on the proximally-directed forces applied by the embolic element to cause inversion of the occlusive member 1000. Instead, the embolic element can fill the space between the second portion 1012 and the aneurysm wall with or without causing the second portion 1012 to move towards the first portion 1014.

In some embodiments, for example as shown in FIGS. 10A-10C, the occlusive member 1000 and/or mesh is formed of a plurality of braided filaments 1002, each having first and second ends and a length measured therebetween. In contrast to occlusive member 600, the first and second ends of the filaments of occlusive member 1000 are secured relative to one another at the same location (the proximal coupler, not shown). The proximal coupler is configured to be attached to the first and second ends at the distal-most region where the first and second ends come together. As shown in FIGS. 10A-10C, the second ends come together at the bottom of the cavity 1008 and form a proximally-extending column that extends into the collected first ends. The resulting mesh structure thus has a "double layer" delivery configuration in which the first and second portions 1014, 1012 of the wall radially overlap one another when the occlusive member 1000 is in a low-profile state and contained within a delivery catheter.

Figure 11A:
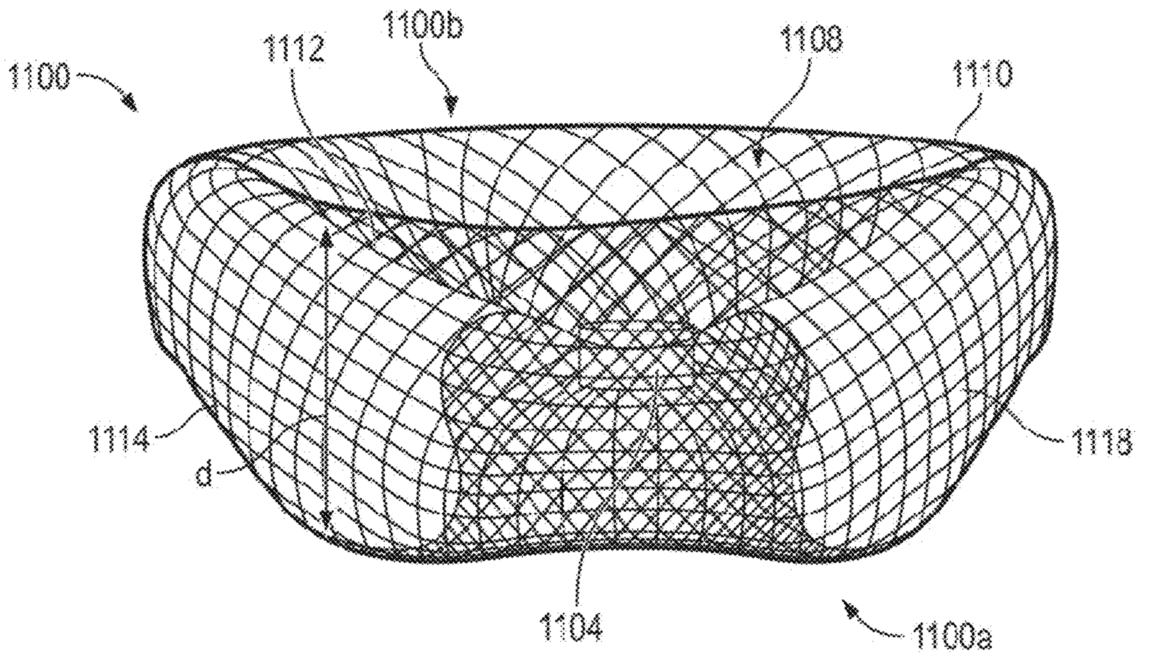
FIGS. 11A and 11B are side and cross-sectional views, respectively, of an occlusive member configured in accordance with several embodiments of the present technology.
Figure 11B:
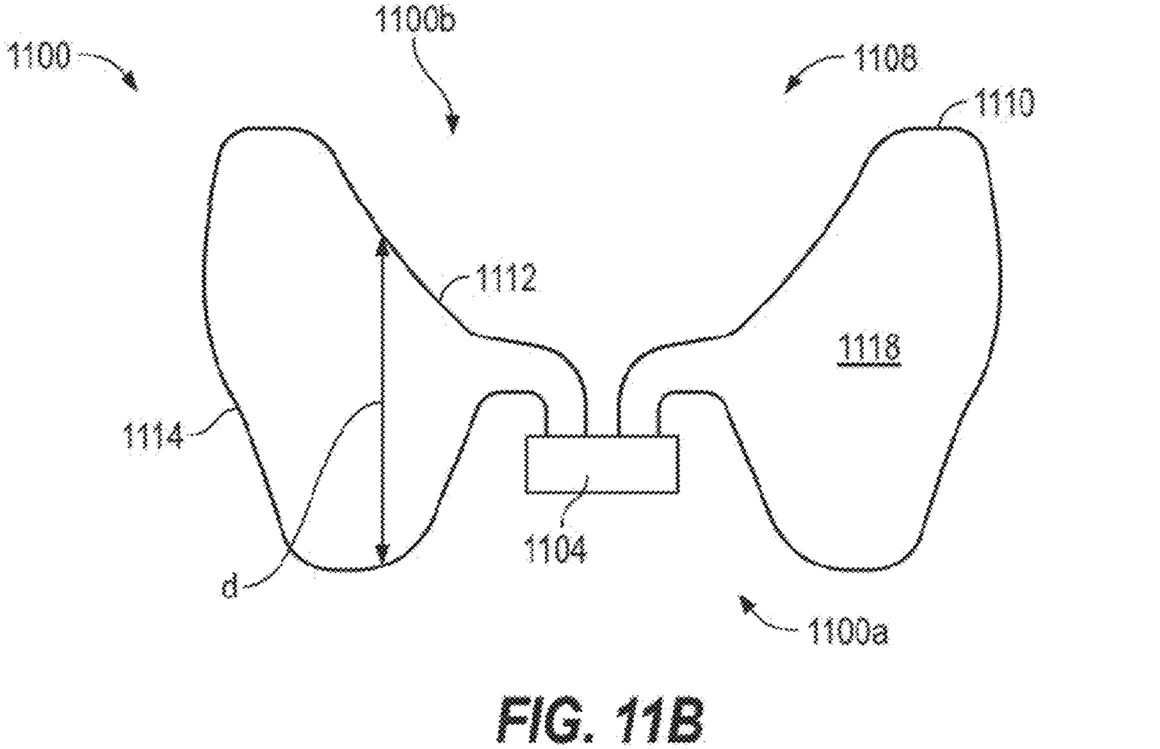
Figure 12:
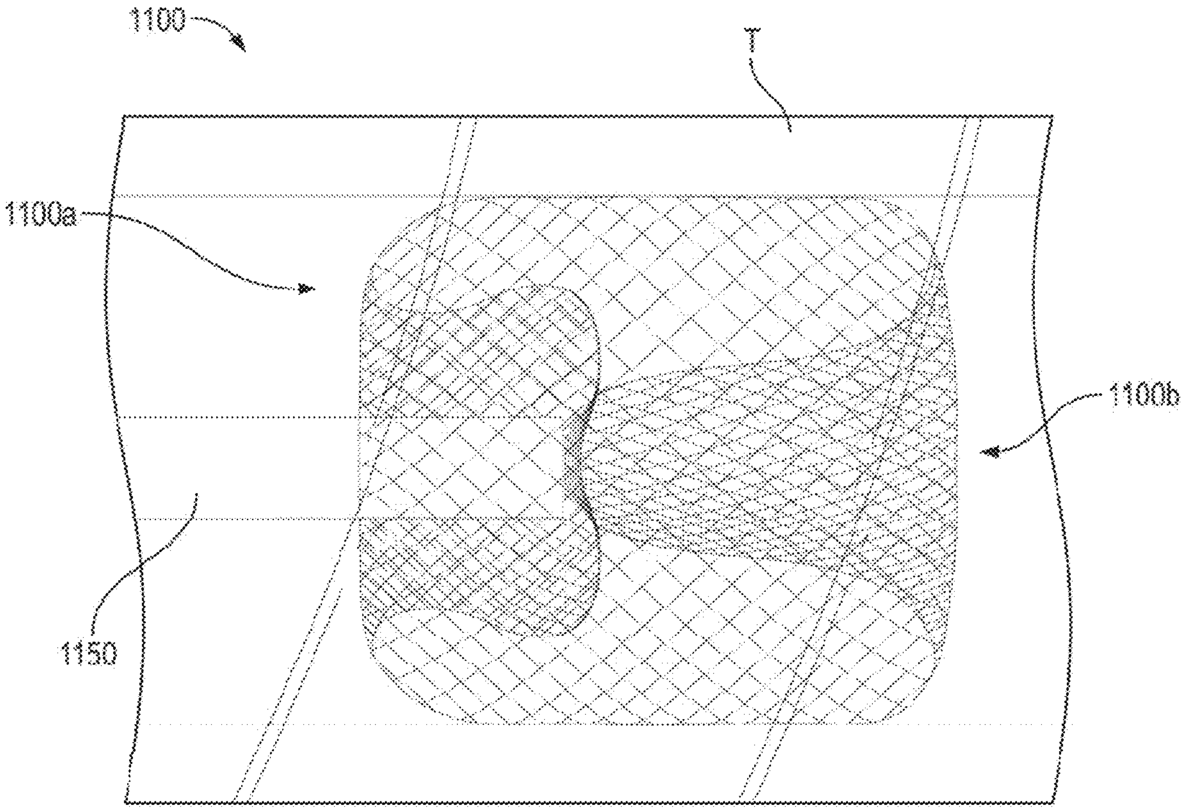
FIG. 12 is a side view of the occlusive member of FIGS. 11A and 11B shown deployed in a transparent tube.

FIGS. 11A and 11B are side and cross-sectional views, respectively, of an occlusive member 1100 configured in accordance with several embodiments of the present technology. As shown in FIGS. 11A and 11B, the occlusive member 1100 can have a double-layer delivery configuration. In some embodiments, the occlusive member 1100 has a first portion 1114 that extends proximally from the ridge 1110 then turns and extends distally towards the proximal coupler 1104. As such, the first and second portions extend longitudinally towards one another to meet at the proximal coupler 1104. FIG. 12 is a side view of the occlusive member of FIGS. 11A and 11B shown in an expanded, elongated configuration in a transparent tube.

Figure 13A:
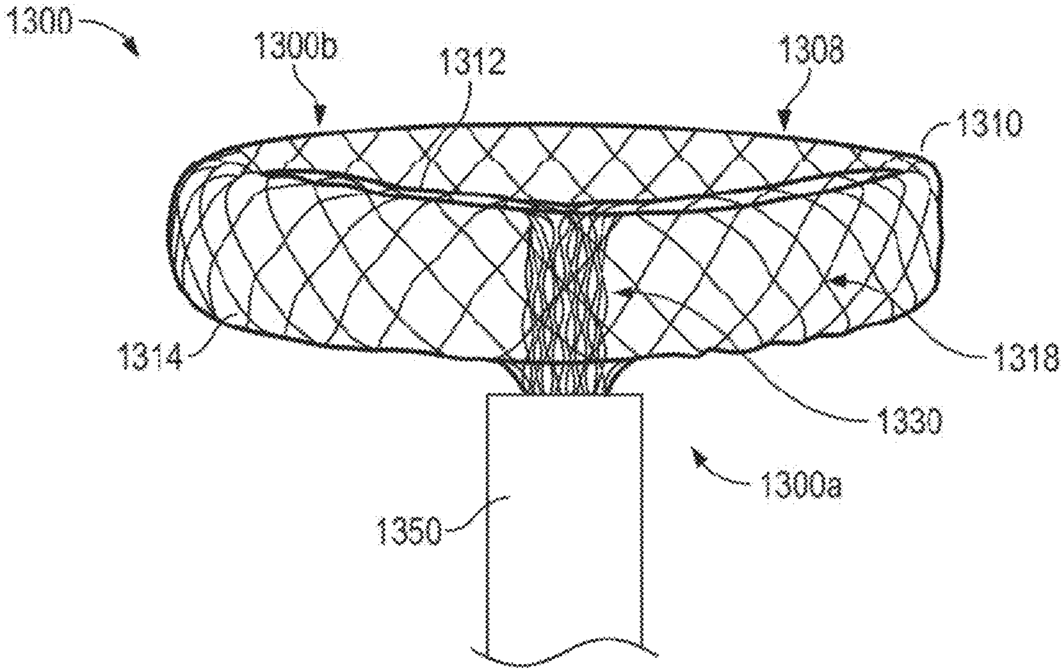
FIGS. 13A and 13B are side and cross-sectional views, respectively, of an occlusive member configured in accordance with several embodiments of the present technology.
Figure 13B:
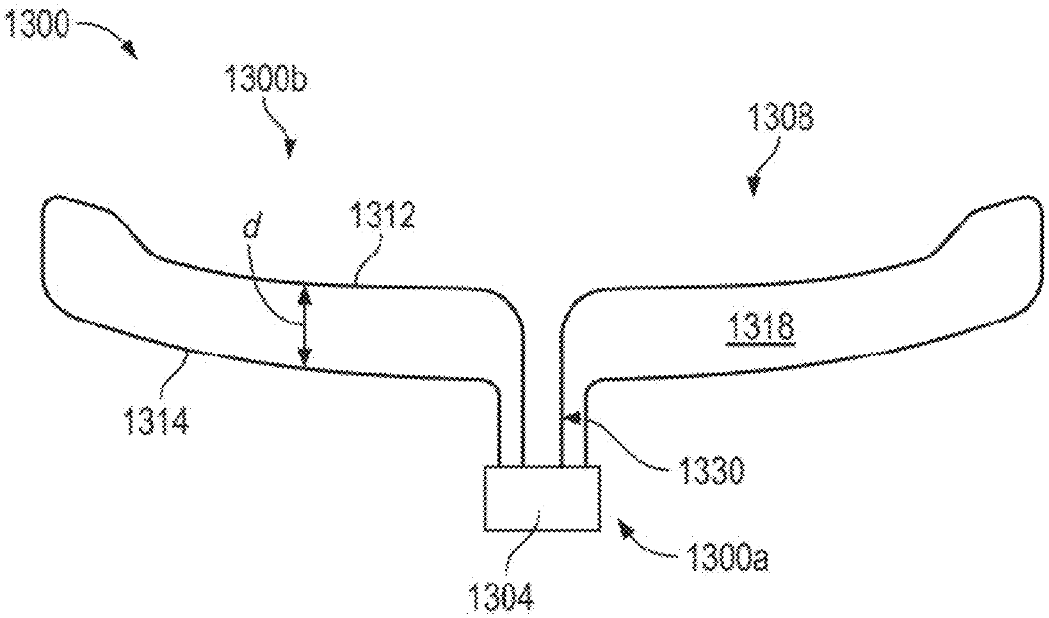

FIGS. 13A and 13B are side and cross-sectional views, respectively, of an occlusive member 1300 configured in accordance with several embodiments of the present technology. As shown in FIGS. 13A and 13B, the occlusive member 1300 can have a double-layer delivery configuration. In contrast to occlusive member 1100, occlusive member 1300 has a generally constant distance d between the first and second portions 1314, 1312 such that the occlusive member 1300 has a disc-shape in the first expanded state.

Figure 14A:
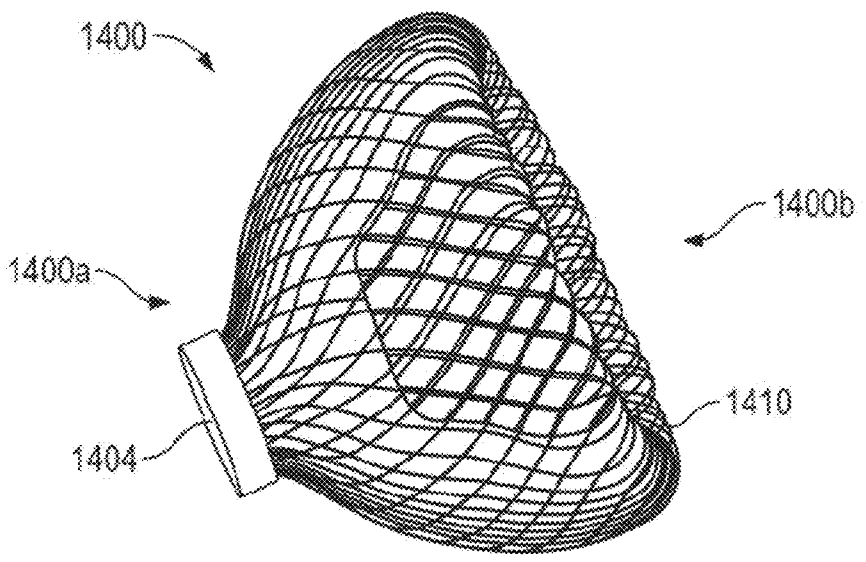
FIGS. 14A and 14B are side and cross-sectional views, respectively, of an occlusive member configured in accordance with several embodiments of the present technology.
Figure 14B:
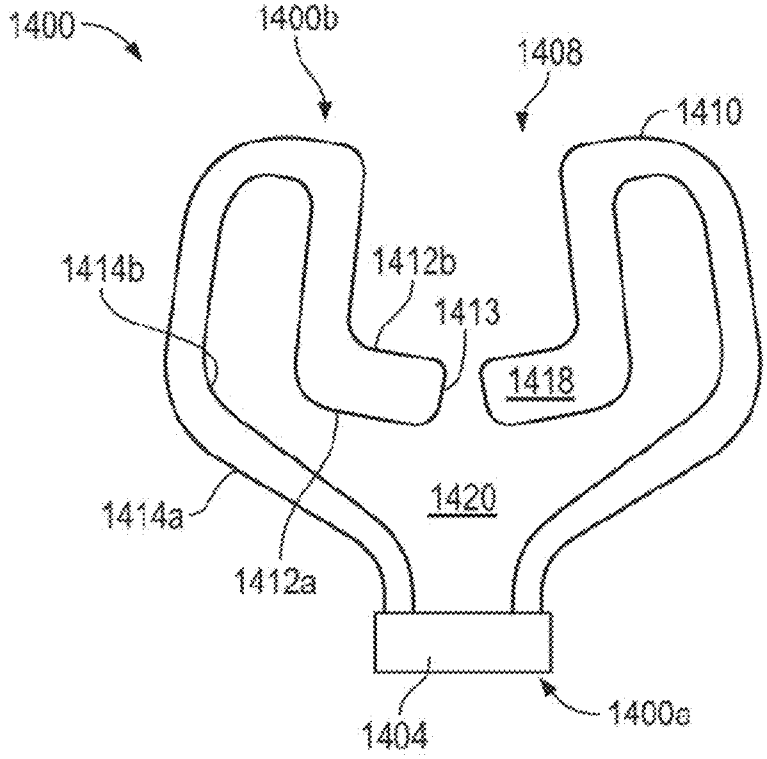

FIGS. 14A and 14B are side and cross-sectional views, respectively, of an occlusive member 1400 configured in accordance with several embodiments of the present technology. As shown in FIGS. 14A and 14B, the occlusive member 1400 has a "quadruple layer" delivery configuration in which portions 1414*a*, 1414*b*, 1412*a*, and 1412*b* radially overlap one another when the occlusive member 1400 is in a low profile state in a delivery catheter. In contrast to several of the previous embodiments, the ridge 1410 is formed by a bend in the first portion 1414*a*, and does not correspond to where the first and second portions 1414, 1412 meet. Instead, the first and second portions 1414, 1412 meet at fold 1413, which lies within the cavity 1408.

Figure 15A:
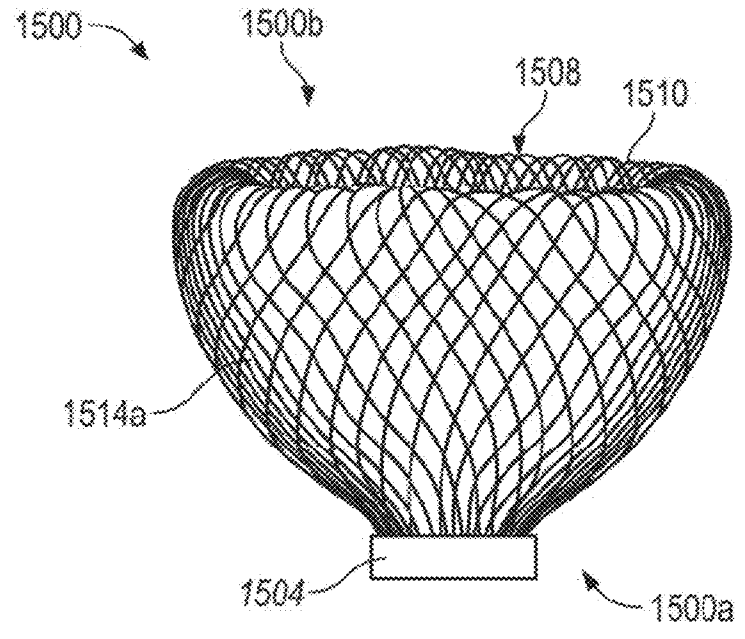
FIGS. 15A and 15B are side and cross-sectional views, respectively, of an occlusive member configured in accordance with several embodiments of the present technology.
Figure 15B:
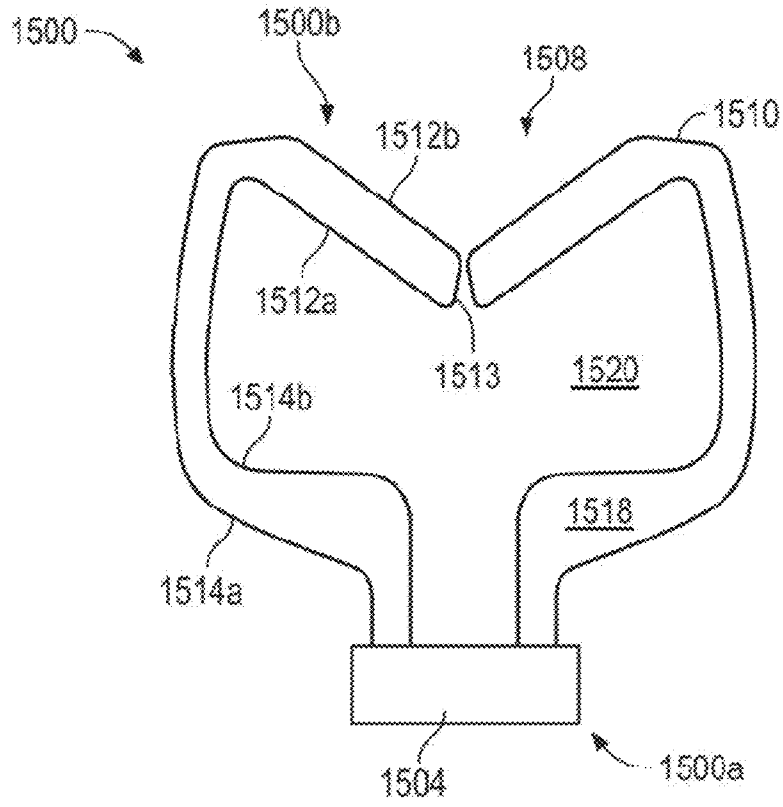

FIGS. 15A and 15B are side and cross-sectional views, respectively, of an occlusive member 1500 configured in accordance with several embodiments of the present technology. As shown in FIGS. 15A and 15B, the occlusive member 1500 has a "quadruple" layer delivery configuration. The occlusive member 1500 has a second portion 1512 with a substantially constant slope.

V. Selected Methods of Manufacturing

The present technology relates to occlusive devices and associated methods of manufacturing. Specific details of these and other methods of manufacturing the mesh structures of the present technology are described below with reference to FIGS. 16-21D.

Figure 16:
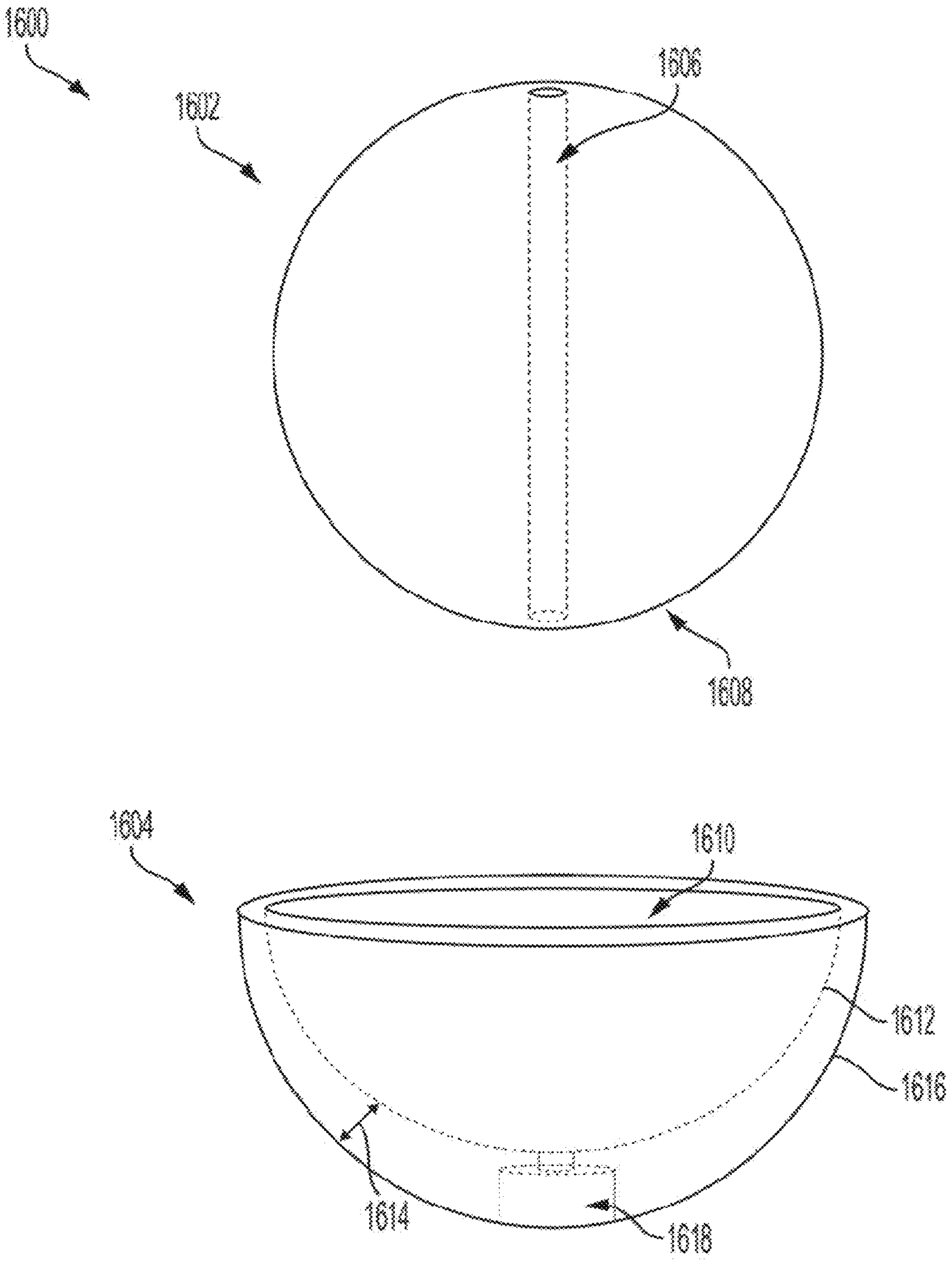
FIG. 16 depicts a forming assembly configured in accordance with several embodiments of the present technology.

In some embodiments, a forming assembly of the present technology comprises multiple forming members. For example, FIG. 16 depicts a forming assembly 1600 (or "assembly 1600") in accordance with several embodiments of the present technology, shown in an unassembled state. As shown in FIG. 16, the assembly 1600 can comprise a first member 1602 and a second member 1604 (collectively "members 1602, 1604"). The members 1602, 1604 may be configured to be positioned adjacent one another so that when a mesh is positioned between the members 1602, 1604, the mesh substantially conforms to a surface of each of the members 1602, 1604. A shape of each of the members 1602, 1604 may be based on a desired predetermined shape of the occlusive device and/or the geometry of the aneurysm to be treated. Suitable shapes of the members 1602, 1604 include, but are not limited to, spherical and non-spherical shapes, cylinders, hemispheres, polyhedrons (e.g., cuboids, tetrahedrons (e.g. pyramids), octahedrons, prisms, etc.), oblate spheroids, plates (e.g., discs, polygonal plates), bowls, non-spherical surfaces of revolution (e.g., toruses, cones, cylinders, or other shapes rotated about a center point or a coplanar axis), and combinations thereof.

According to some embodiments, for example as shown in FIG. 16, the first member 1602 has a generally globular shape. The first member 1602 may have a lumen 1606 extending through at least a portion of the first member 1602. For example, as shown in FIG. 16, the lumen 1606 may extend through a thickness of the first member 1602. Further, the lumen 1606 may extend along a longitudinal axis of the first member 1602. In some embodiments, a diameter of the lumen 1606 is based, at least in part, on a diameter of the tubular mesh. Additionally or alternatively, the diameter of the lumen 1606 may be selected to enable the first member 1602 to receive at least a portion of an elongate member, such as a mandrel, within the lumen 1606. The first member 1602 can have a first mating surface 1608 comprising at least a portion of an outer surface of the first member 1602. According to several embodiments, the first mating surface 1608 is configured to influence a shape of the contoured mesh produced as described herein, as at least a portion of the mesh may conform to the first mating surface 1608 during the shape-setting process.

As shown in FIG. 16, the second member 1604 can have a generally hemispherical shape defining a cavity 1610 with a second mating surface 1612 (e.g., a hollow hemispherical shape). The second mating surface 1612 may be arcuate (see FIG. 16). The second member 1604 may be configured to receive at least a portion of the first member 1602 within the cavity 1610 of the second member 1604. Accordingly, in some embodiments, the second mating surface 1612 has a shape based on a shape of the first mating surface 1608 of the first member 1602. The second member 1604 depicted in FIG. 16 comprises a thickness 1614 between an outer surface 1616 of the second member 1604 and the second mating surface 1612. The thickness 1614 can be uniform or nonuniform across the second member 1604. The second member 1604 can comprise a lumen 1618 extending through the second member 1604 and/or along a longitudinal axis of the second member 1604. The lumen 1618 can comprise a constant diameter or the diameter of the lumen 1618 may vary across a length of the lumen 1618. In some embodiments, a first portion of the lumen 1618 may have a first diameter sufficient to receive at least a portion of a mandrel and/or the mesh within the first portion of the lumen 1618. A second portion of the lumen 1618 may have a second diameter that is substantially equivalent to a diameter of the lumen 1606 of the first member 1602. Although not depicted in FIG. 16, the second member 1604 may comprise a protrusion extending from the outer surface 1616 and/or the second mating surface 1612. The protrusion may be configured to influence the shape of the mesh, facilitate coupling of the mesh to the second member 1604, align the mesh with the second member 1604, etc.

FIGS. 17A-17D depict various stages of an example method for forming a contoured mesh of an occlusive device using the assembly 1600 and a mesh 1720 comprising a first end portion 1720*a*, a second end portion 1720*b*, and intermediate portion 1720*c* therebetween. The mesh 1720 can have a tubular configuration with a lumen 1722 extending along a length of the mesh 1720. Although the mesh 1720 shown in FIG. 17A comprises a single layer, the mesh 1720 may comprise any suitable number of layers, as previously described. A mesh used to form an occlusive device of the present technology may initially comprise a tubular configuration, such as a braided mesh tube. The mesh tube may comprise one layer, two layers, three layers, or more. The number of layers may be selected based on a desired property of the occlusive device. For example, a mesh comprising two layers may have a lower porosity and may be able to apply greater radial force than a single-layered mesh. In some embodiments, the mesh is everted or inverted such that the tubular mesh comprises inner and outer layers meeting at a fold.

Figure 17B:
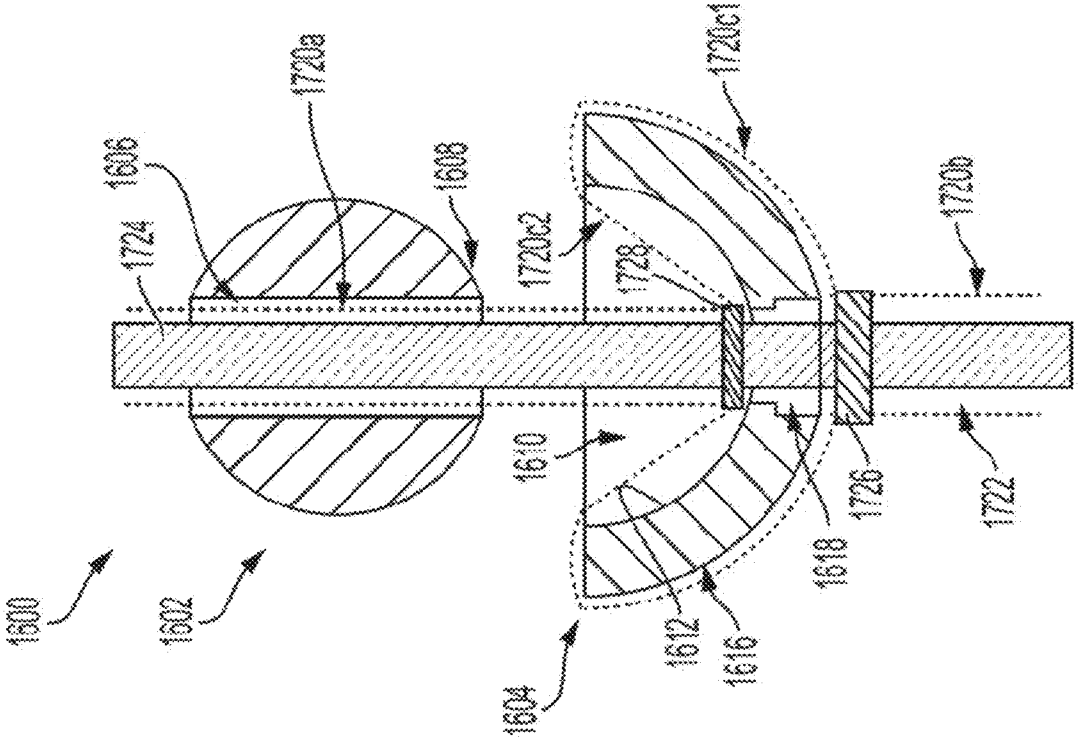
FIGS. 17A-17D are cross-sectional views of a forming assembly and a mesh at various stages of a method for making an occlusive device in accordance with several embodiments of the present technology.
Figure 17A:
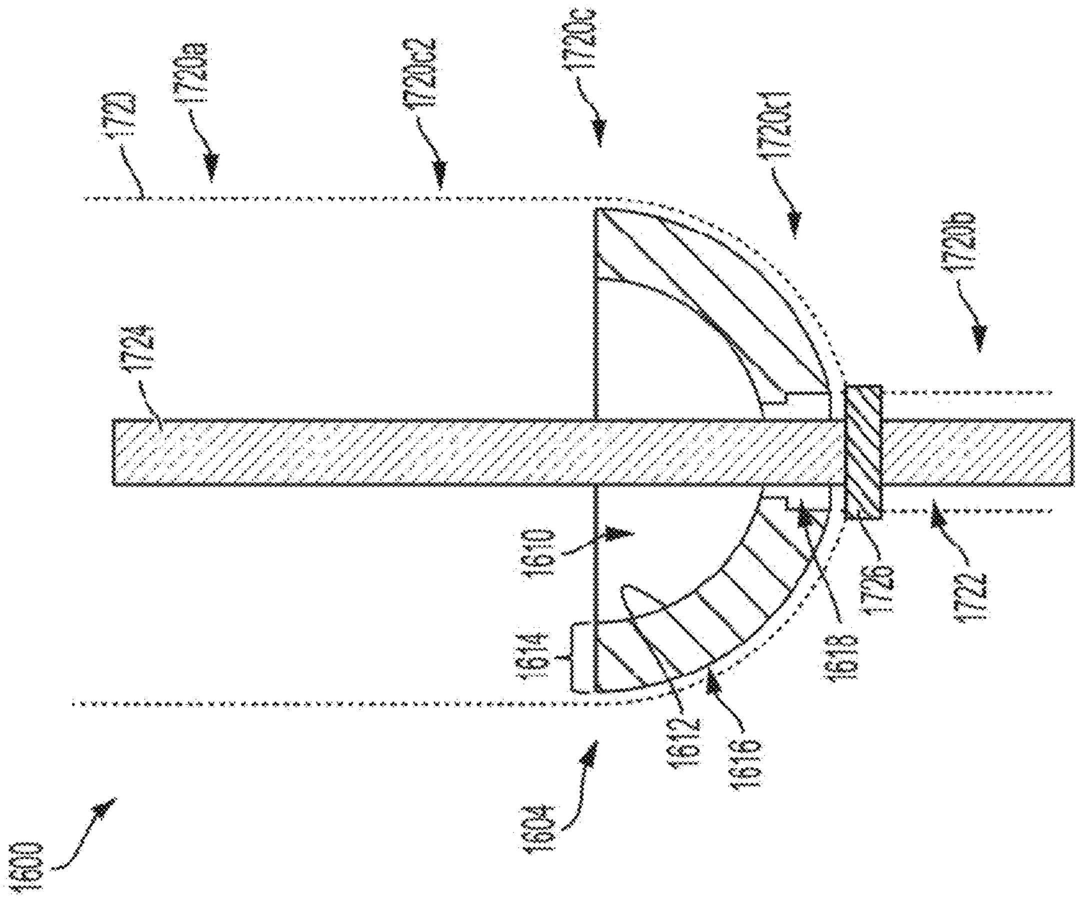

As shown in FIG. 17A, the method can include positioning at least a first portion 1720*c*1 of the intermediate portion 1720*c* of the mesh 1720 over the second member 1604 so that the first portion 1720*cl* substantially conforms to the outer surface 1616 of the second member 1604 and the first and second end portions 1720*a*, 1720*b* extend away from the second member 1604 in opposing directions. Positioning the first portion 1720*cl* of the intermediate portion 1720*c* of the mesh 1720 over the second member 1604 may comprise stretching the mesh 1720.

According to some embodiments, for example as shown in FIG. 17A, at least a portion of a mandrel 1724 is positioned within the lumen 1722 of the mesh 1720 and/or the lumen 1618 of the second member 1604. The mandrel 1724 can have a generally tubular shape with a circular cross-sectional shape. Additionally or alternatively, the mandrel 1724 may have another suitable cross-sectional shape including, but not limited to, rectangular, ovoidal, etc. The cross-sectional shape of the mandrel 1724 may be constant along a length of the mandrel 1724 or may vary along the length of the mandrel 1724. The mandrel 1724 can have a substantially constant thickness along the length of the mandrel 1724 or the thickness of the mandrel 1724 may vary along its length. In some embodiments, a first coupling element 1726 is employed to couple at least a portion of the mesh 1720 to the mandrel 1724 so that the mesh 1720 substantially conforms to the shape of the mandrel 1724. The first coupling element 1726 may removably or permanently couple to the mesh 1720 and/or mandrel. As shown in FIG. 17A, the first coupling element 1726 may circumferentially surround the mesh 1720. The first coupling element 1726 may be, for example, a wire tie, a coil, adhesive, a weld, a marker band, and/or other suitable coupling elements. The first coupling element 1726 may be radiopaque to facilitate visualization of the occlusive device. In some embodiments, multiple coupling elements 1726 are coupled to multiple portions of the mesh.

Moreover, one or more coupling elements may be employed to facilitate conforming the mesh 1720 to the first member 1602 and/or the second member 1604. For example, as shown in FIG. 17B, a second coupling element 1728 can be coupled to the mesh 1720 at a position adjacent to the second mating surface 1612 of the second member 1604 such that a second portion 1720*c*2 of the intermediate portion 1720*c* of the mesh 1720 is positioned within the cavity 1610 of the second member 1604. As described herein with reference to the first coupling element 1726, the second coupling element 1728 may be, for example, a wire tie, a coil, adhesive, a weld, a marker band, and/or other suitable coupling elements. The second coupling element 1728 may be removably or permanently coupled to the mesh 1720, the mandrel 1724, and/or the second member 1604. As shown in FIG. 17B, the second portion 1720*c*2 of the intermediate portion 1720*c* of the mesh 1720 may not exactly conform to the second mating surface 1612 of the second member 1604.

In some embodiments, additional coupling elements may be employed to cause the second portion **1720*c*2 to substantially conform to the second mating surface 1612 of the second member 1604. Alternatively or additionally, as described herein the first member 1602 may be at least partially received within the cavity 1610 of the second member 1604 to cause the second portion 1720*c*2 of the intermediate portion 1720*c* of the mesh 1720 to conform to the second mating surface 1612 of the second member 1604**.

In some embodiments, for example as shown in FIG. 17B, at least a portion of the first end portion **1720*a* of the mesh 1720 is positioned within the lumen 1606 of the first member 1602. Additionally or alternatively, at least a portion of the mandrel 1724 may be positioned within the lumen 1606 of the first member 1602 to facilitate aligning the first and second members 1602, 1604 and/or to facilitate positioning the first end portion 1720*a* of the mesh 1720 within the lumen 1606 of the first member 1602. In some embodiments, the lumen 1606 of the first member 1602 is configured to radially constrain the tubular first end portion 1720*a* of the mesh 1720** during the shape-setting process.

Figure 17D:
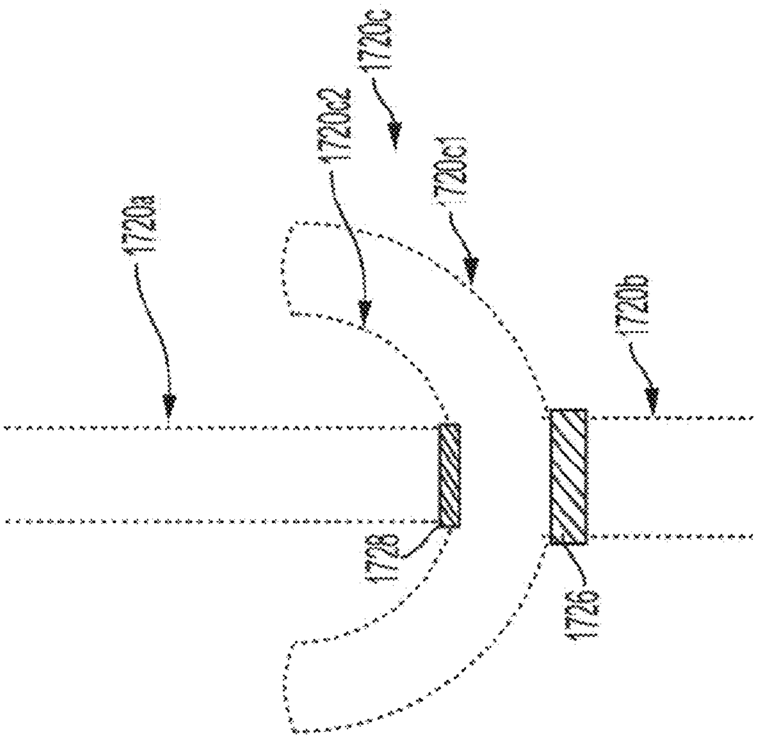
Figure 17C:
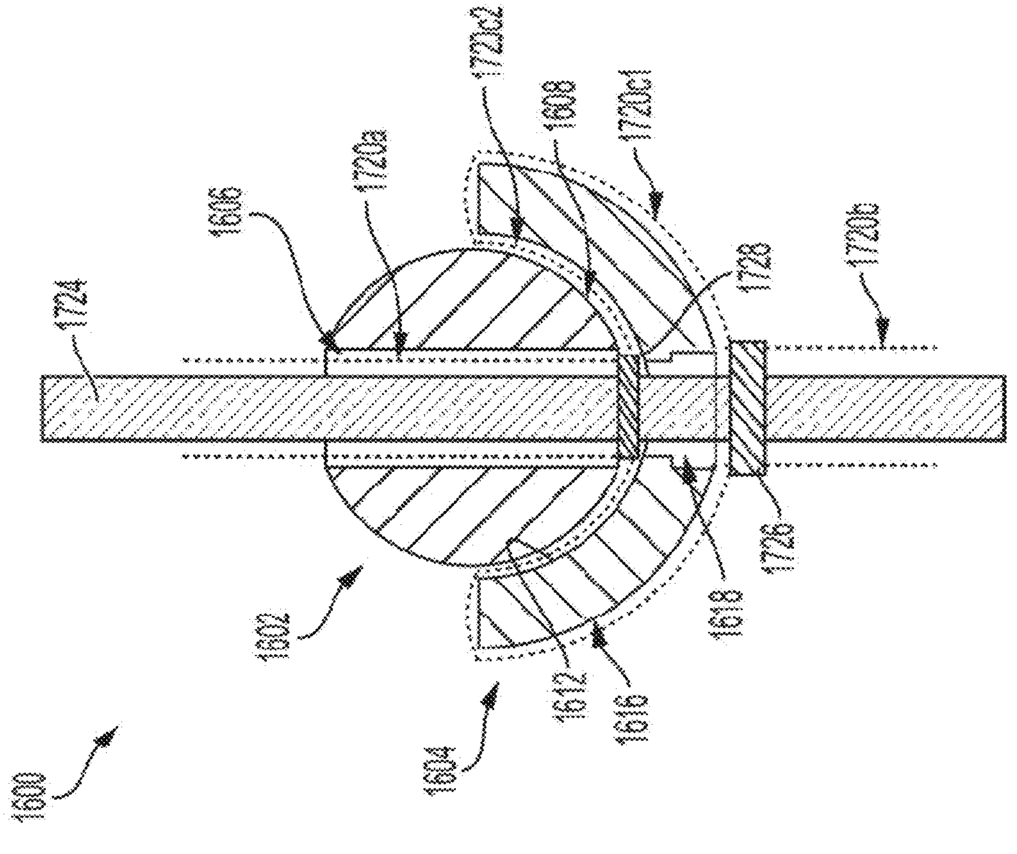

As shown in FIG. 17C, the method may include positioning the first member 1602 at least partially within the cavity 1610 of the second member 1604 so that the second portion **1720*c*2 of the intermediate portion 1720*c* of the mesh 1720 substantially conforms to the second mating surface 1612 of the second member 1604 and/or the first mating surface 1608 of the first member 1602. In some embodiments, the second portion 1720*c*2 is compressed between the first and second members 1602, 1604. The first and second members 1602, 1604 may be fixed in place prior to setting a shape of the mesh 1720**.

According to some embodiments, setting a shape of the mesh 1720 comprises subjecting the assembly 1600 and the mesh 1720 to a heat treatment procedure. One example of a heat treatment procedure can include heating the assembly 1600 and the mesh 1720 to a selected temperature (such as, but not limited to, between 540 and 660 degrees centigrade) for a selected period of time (such as, but not limited to, between 5 and 15 minutes), followed by rapid cooling. The rapid cooling can be achieved by any suitable cooling procedure such as, but not limited to water quench or air-cooling. In other examples, the time and temperature for heat treatment can be different than those discussed above, for example, based upon the desired material properties of the occlusive device. In particular examples, the heat treatment procedure may be carried out in an air or vacuum furnace, salt bath, fluidized sand bed or other suitable system. The heat treatment procedure may comprise a single procedure or multiple procedures. After completing the heat treatment, the mesh 1720 has a desired contoured shape and configuration (e.g., corresponding substantially to the assembly 1600). In other examples, other suitable heat-treating procedures may be employed including, but not limited to resistive heating or heating by running a current though the mesh 1720. In some embodiments, setting a shape of the mesh 1720 comprises a heat-free procedure such as mechanical deformation.

The contoured mesh 1720 may be separated and removed from the assembly 1600. In some embodiments, the first coupling element 1726 and/or the second coupling element 1728 may be removed from the mesh 1720. Alternatively, one or both of the first and second coupling elements 1726, 1728 may remain attached to the mesh 1720. One or more additional post processing operations may be provided on the contoured mesh 1720, including, but not limited to abrasive grit blasting, shot peening, polishing, chemical etching, electropolishing, electroplating, coating, ultrasonic cleansing, sterilizing or other cleaning or decontamination procedures.

FIG. 17D depicts a cross-sectional view of the contoured mesh 1720 separated from the assembly 1600 and having a predetermined shape in an expanded, unconstrained state. The first end portion **1720*a* and the second end portion 1720*b* of the contoured mesh 1720 may each comprise a generally tubular configuration. As shown in FIG. 17D, the first portion 1720*c*1 of the intermediate portion 1720*c* of the mesh 1720 may have a shape based on the outer surface 1616 of the second member 1604 and the second portion 1720*c*2 of the intermediate portion 1720*c* of the mesh 1720 may have a shape based on the first and second mating surfaces 1608, 1612. Accordingly, the intermediate portion 1720*c* of the mesh 1720 may form a dual-layered sidewall that encloses an open volume. The dual-layered sidewall may have a generally hollow, hemispherical shape, as shown in FIG. 17D. Moreover, the dual-layered sidewall may enclose an open volume having a substantially hemispherical shape. As such, the thickness 1614 of the second member 1604 influences the size of the open volume enclosed by the contoured mesh 1720. As shown in FIG. 17D and as previously described, the first coupling element 1726 and/or the second coupling element 1728 may remain coupled to the contoured mesh 1720. Prior to deployment of the occlusive device, the contoured mesh 1720** may be coupled to additional components (e.g., embolic materials, coupling elements, etc.) and/or assembled within a delivery system.

Figure 18A:
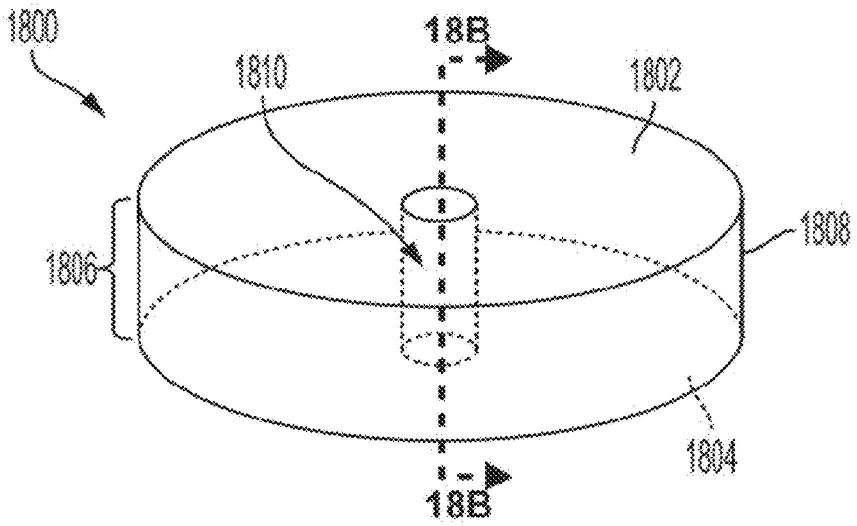
FIG. 18A depicts a forming member configured in accordance with several embodiments of the present technology.
Figure 18B:
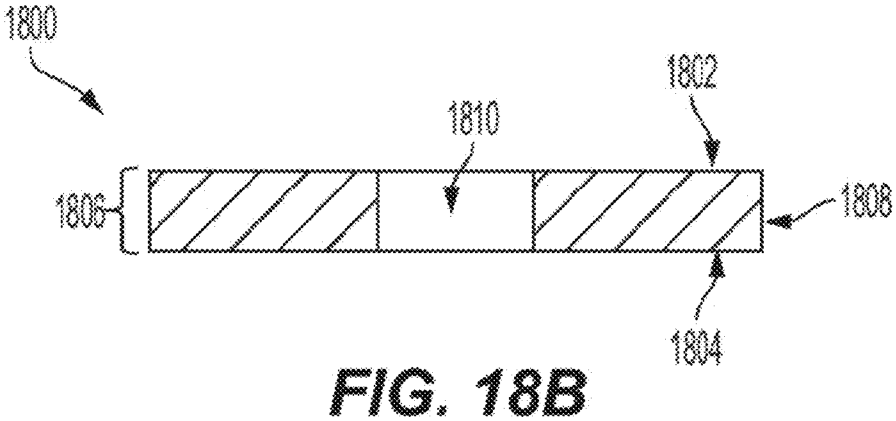
FIG. 18B is a cross-sectional view of the forming member shown in FIG. 18A, taken along line 18B-18B.

Although FIGS. 16-17D depict first and second members 1602, 1604 with generally globular and hemispherical shapes, respectively, members of a forming assembly of the present technology may each comprise any suitable shape, as previously described. For example, FIGS. 18A and 18B depict isometric and cross-sectional views, respectively, of a forming member 1800 configured in accordance with several aspects of the present technology. The forming member 1800 shown in FIGS. 18A and 18B may be used to form a dual-layered, contoured mesh having an open first end portion and a closed second end portion that is positioned at an angle with respect to the first end portion. The forming member 1800 may comprise a first surface 1802, a second surface 1804 opposite the first surface 1802 along a thickness 1806 of the forming member 1800, and a sidewall 1808 therebetween. In some embodiments, the first and second surfaces 1802, 1804 are generally circular and/or the sidewall 1808 is generally annular such that the forming member 1800 has a generally cylindrical shape. However, the forming member 1800 may comprise any suitable shape including, but not limited to, spherical, non-spherical, cylindrical, hemispherical, polyhedron (e.g., cuboid, tetrahedron (e.g. pyramids), octahedron, prism, etc.), oblate spheroid, plate (e.g., disc, polygonal plate), bowl, non-spherical surface of revolution (e.g., torus, cone, or another shape rotated about a center point or a coplanar axis), and combinations thereof. The thickness 1806 of the forming member 1800 may be constant along a length of the forming member 1800 or may vary along the length of the forming member 1800. As previously described, the thickness 1806 of the forming member 1800 can influence a size of an open volume of a contoured mesh formed with the forming member 1800. The forming member 1800 can comprise a lumen 1810 extending at least partially through the forming member 1800 between the first and second surfaces 1802, 1804 and/or along a longitudinal axis of the forming member 1800. As described herein, the lumen 1810 may comprise any suitable length and diameter.

Figure 19B:
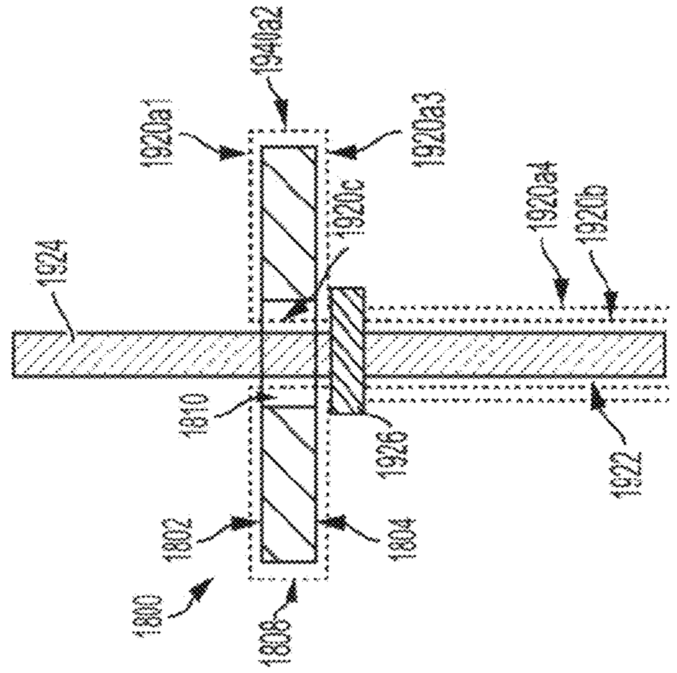
FIGS. 19A-19C are cross-sectional views of a forming member and a mesh at various stages of a method for making an occlusive device in accordance with several embodiments of the present technology.
Figure 19A:
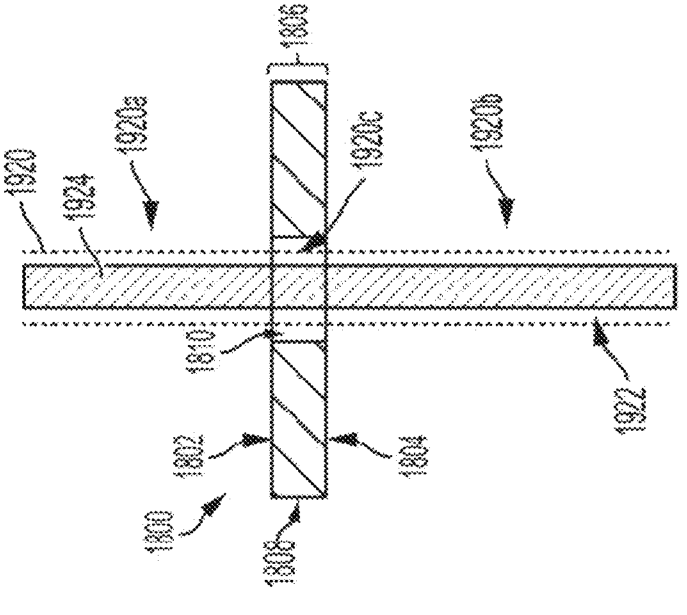
Figure 19C:
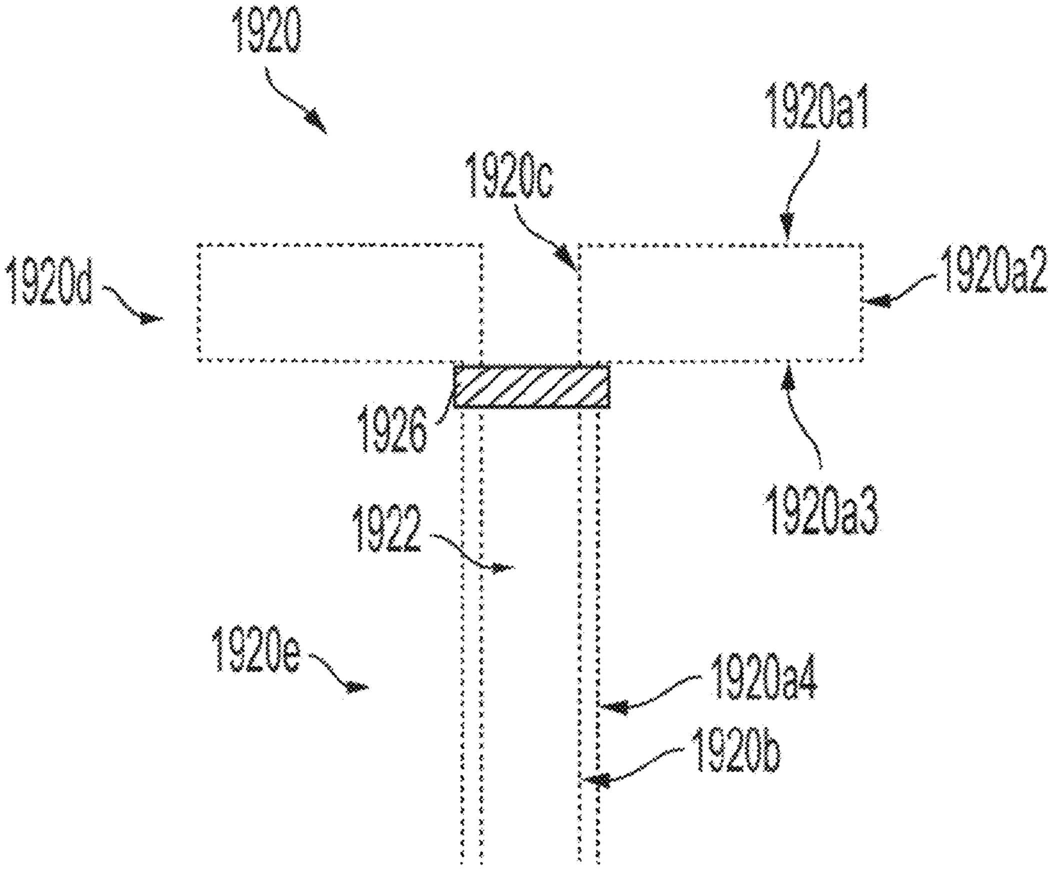

FIGS. 19A-19C depict various stages of an example method for forming a contoured mesh of an occlusive device using the forming member 1800 and a single-layer, tubular mesh 1920 having a first end portion 1920*a*, a second end portion 1920*b*, an intermediate portion 402*c* therebetween, and a lumen 1922 extending along a length of the mesh 1920. As shown in FIG. 19A, the method may include positioning the intermediate portion 1920*c* of the mesh 1920 within the lumen 1810 of the forming member 1800 so that the first end portion 1920*a* of the mesh 1920 extends away from the first surface 1802 of the forming member 1800 in a first direction and the second end portion 1920*b* of the mesh 1920 extends away from the second surface 1804 of the forming member 1800 in a second direction that is opposite the first direction. In some embodiments (see FIG. 19A), a mandrel 1924 is positioned within the lumen 1922 of the mesh 1920 and/or the lumen 1810 of the forming member 1800.

As shown in FIG. 19B, the method may comprise everting the mesh 1920 to position a first portion 1920*a*1 of the first end portion 1920*a* of the mesh 1920 over the first surface 1802 of the forming member 1800 and a second portion 1920*a*2 of the first end portion 1920*a* of the mesh 1920 over the sidewall 1808 of the forming member 1800. In some embodiments, for example as shown in FIG. 19B, a coupling element 1926 is coupled to the mesh 1920 and/or the mandrel 1924 to cause a third portion 1920*a*3 of the first end portion 1920*a* of the mesh 1920 to substantially conform to the second surface 1804 of the forming member 1800. As described herein, the coupling element 1926 may be, for example, a wire tie, adhesive, a weld, a marker band, and/or other suitable coupling elements. As shown in FIG. 19B, the coupling element 1926 may circumferentially surround the mesh 1920 and/or the mandrel 1924. Although FIG. 19B shows the coupling element 1926 coupled to only a portion of the mesh 1920, the coupling element 1926 may be coupled to any length of the mesh 1920 and/or mandrel 1924. The coupling element 1926 can be positioned adjacent the second surface 1804 of the forming member 1800, as shown in FIG. 19B, so that the third portion 1920*a*3 of the first end portion 1920*a* of the mesh 1920 extends along a substantially straight path between the sidewall 1808 of the forming member 1800 and the coupling element 1926, so that the third portion 1920*a*3 substantially conforms to the second surface 1804 of the forming member 1800. However, in some embodiments, the coupling element 1926 may be positioned further from the second surface 1804 of the forming member 1800 so that the third portion 1920*a*3 of the first end portion 1920*a* of the mesh 1920 extends along a substantially curved path between the sidewall 1808 of the forming member 1800 and the coupling element 1926. In several embodiments, no coupling elements are coupled to the mesh 1920. Additionally or alternatively, another forming member can be used to cause the mesh 1920 to conform to the forming member 1800 and/or to a desired shape. In any case, a fourth portion 1920*a*4 of the first end portion 1920*a* of the mesh 1920 extends away from the second surface 1804 of the forming member 1800 in the second direction. As previously described, setting a shape of the mesh 1920 may comprise subjecting the forming member 1800 and the mesh 1920 to a heat treatment procedure.

FIG. 19C depicts the dual-layered, contoured mesh 1920 resulting from the method depicted in FIGS. 19A and 19B and separated from the forming member 1800. The contoured mesh 1920 comprises a closed end portion 1920*d* formed by the intermediate portion 1920*c* and the first, second, and third portions 1920*a*1, 1920*a*2, 1920*a*3 of the first end portion 1920*a* of the mesh 1920. The contoured mesh 1920 also comprises an open end portion 1920*e* formed by the fourth end portion 1920*a*4 of the first end portion 1920*a* of the mesh 1920 and the second end portion 1920*b* of the mesh 1920. As shown in FIG. 19C, the open end portion 1920*e* of the mesh 1920 may have a substantially tubular configuration and the closed end portion 1920*d* of the mesh 1920 may be disposed at an angle to the open end portion 1920*e*. The closed end portion 1920*d* of the mesh 1920 encloses an open volume. In some embodiments, the open volume is substantially disc shaped. As previously described, the size of the open volume may be based, at least in part, on the thickness 1806 of the forming member 1800. The coupling element 1926 may remain positioned around the mesh 1920 (see FIG. 19C) or may be removed.

Figure 20B:
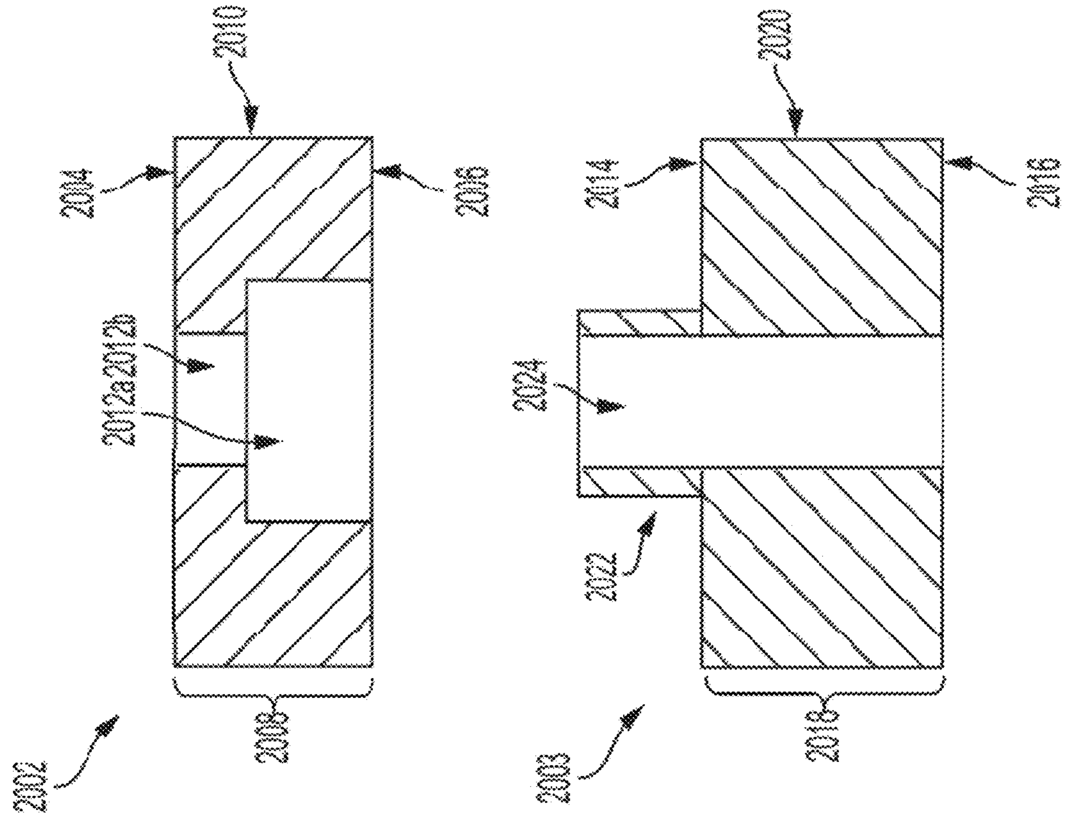
FIG. 20B is a cross-sectional view of the forming assembly shown in FIG. 20A, taken along line 20B-20B.
Figure 20A:
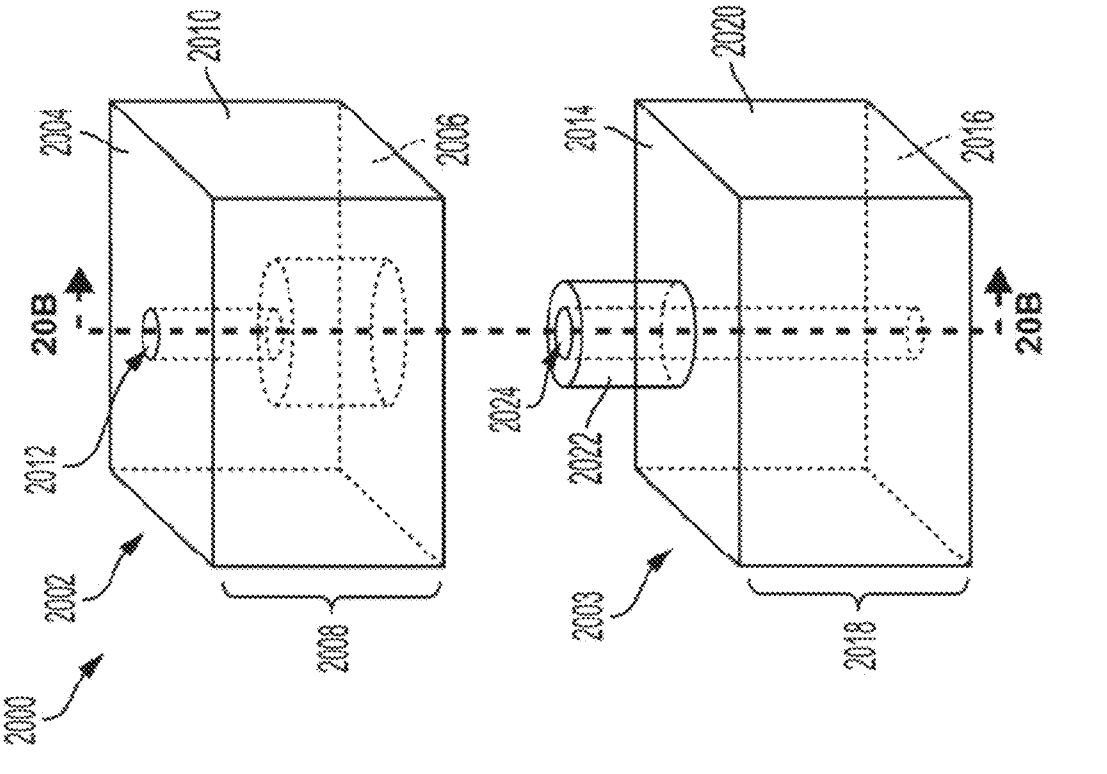
FIG. 20A depicts a forming assembly configured in accordance with several embodiments of the present technology.

According to some embodiments, setting a shape of a mesh to produce a contoured mesh may comprise a single shape-setting procedure. However, in certain embodiments setting a shape of the mesh may comprise two or more shape-setting procedures (e.g., two or more heat treatment processes). For example, a first contoured mesh (e.g., mesh 1920 shown in FIG. 19C) produced from a first shape-setting procedure using a first forming assembly or member (e.g., forming member 1800) may be coupled to a second forming assembly or member, such as forming assembly 2000 (or "assembly 2000") depicted in FIGS. 20A and 20B, and subjected to a second shape-setting procedure to produce a second contoured mesh. The assembly 2000 shown in FIGS. 20A and 20B comprises a first member 2002 and a second member 2003. The first member 2002 has a first surface 2004, a second surface 2006 opposite the first surface 2004 along a thickness 2008 of the first member 2002, and a sidewall 2010 therebetween. As shown in FIG. 20A, the first and second surfaces 2004, 2006 may be generally rectangular such that the first member 2002 has a shape generally corresponding to a rectangular prism. The first member 2002 can comprise a lumen 2012 extending at least partially through the thickness 2008 of the first member 2002. As shown in FIGS. 20A and 20B, in some embodiments, a diameter of the lumen 2012 may vary across the thickness 2008 of the first member 2002. For example, the lumen 2012 may comprise a first portion 2012*a* having a first diameter and a second portion 2012*b* having a second diameter different than the first diameter. The first portion 2012*a* of the lumen 2012 can be configured to receive at least a portion of the second member 2003 and/or the mesh. The second portion 2012*b* of the lumen 2012 can be configured to receive at least a portion of a mandrel and/or the mesh.

Similarly, the second member 2003 has a first surface 2014, a second surface 2016 opposite the first surface 2014 along a thickness 2018 of the second member 2003, and a sidewall 2020 therebetween. The second member 2003 may also have shape generally corresponding to a rectangular prism or another suitable shape. The thickness 2018 of the second member 2003 can be the same as the thickness 2008 of the first member 2002 or may differ from the thickness 2008 of the first member 2002. As shown in FIGS. 20A and 20B, in some embodiments the second member 2003 comprises a protrusion 2022 extending away from the first surface 2014 of the second member 2003 in a first direction. Although the protrusion 2022 is depicted as substantially cylindrical in FIG. 20A, the protrusion 2022 can have any suitable shape, based on a desired shape of the resulting contoured mesh. The second member 2003 can further comprise a lumen 2024 extending along the thickness 2018 of the second member 2003 between the first and second surfaces 2014, 2016. The lumen 2024 may have a constant diameter (see FIGS. 20A and 20B) or may vary in diameter along the thickness 2018 of the second member 2003. The lumen 2024 can be configured to receive at least a portion of the mesh and/or a mandrel.

Figure 21B:
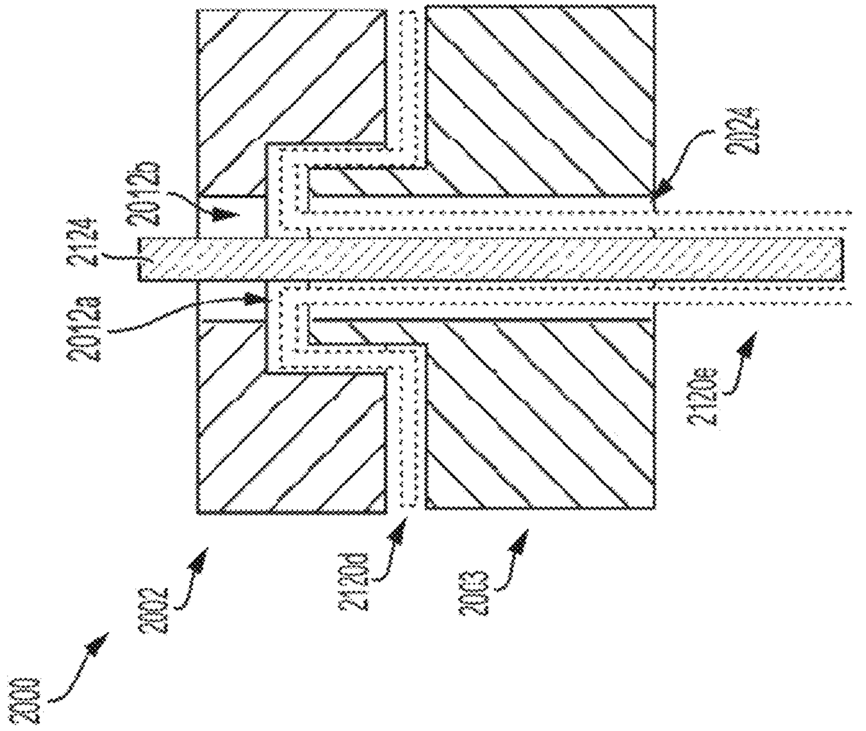
FIGS. 21A-21C are cross-sectional views of a forming assembly and a mesh at various stages of a method for making an occlusive device in accordance with several embodiments of the present technology.
Figure 21A:
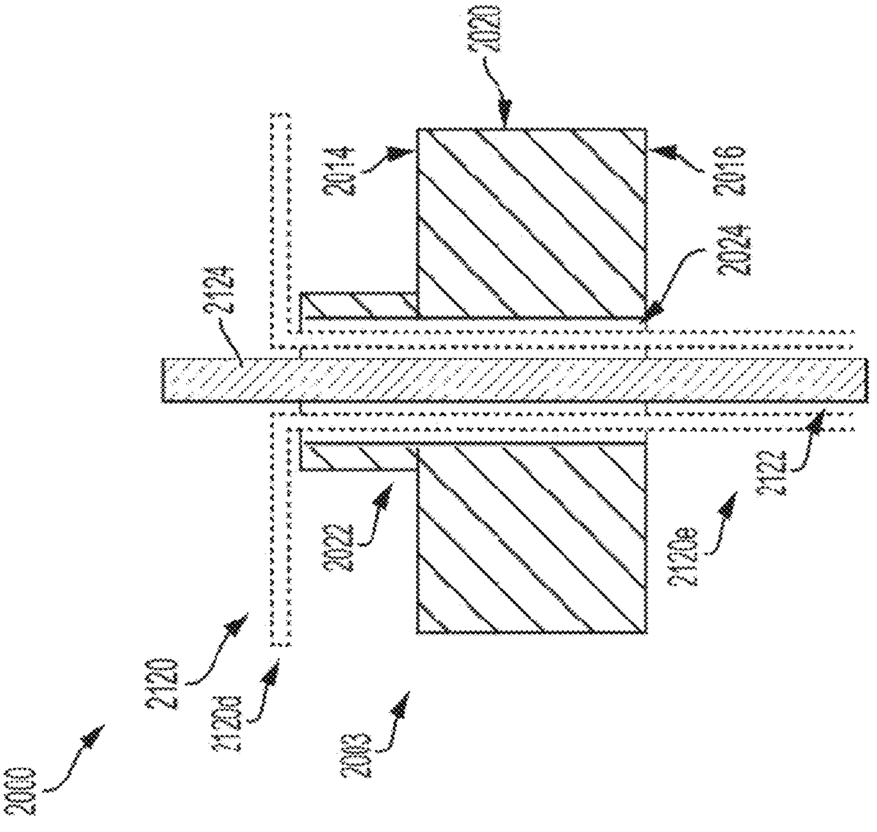
Figure 21D:
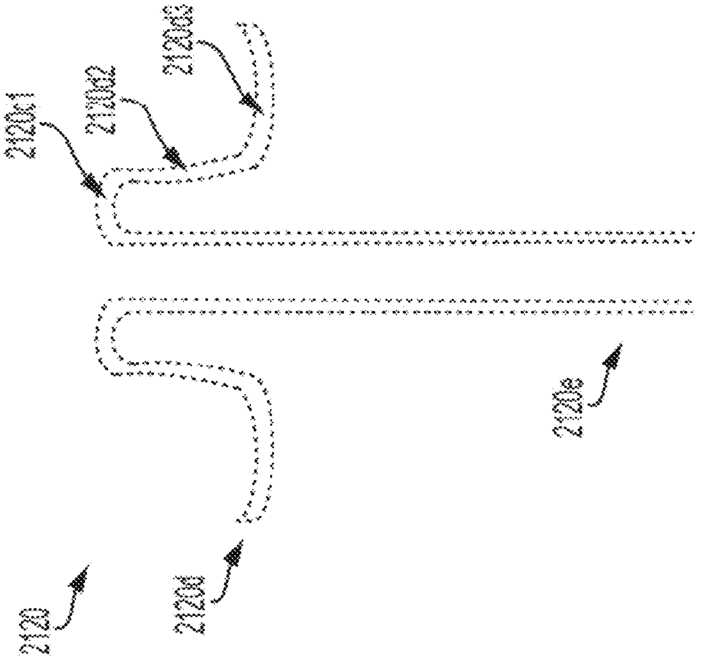
FIG. 21D is a cross-sectional view of a mesh configured in accordance with several embodiments of the present technology.
Figure 21C:
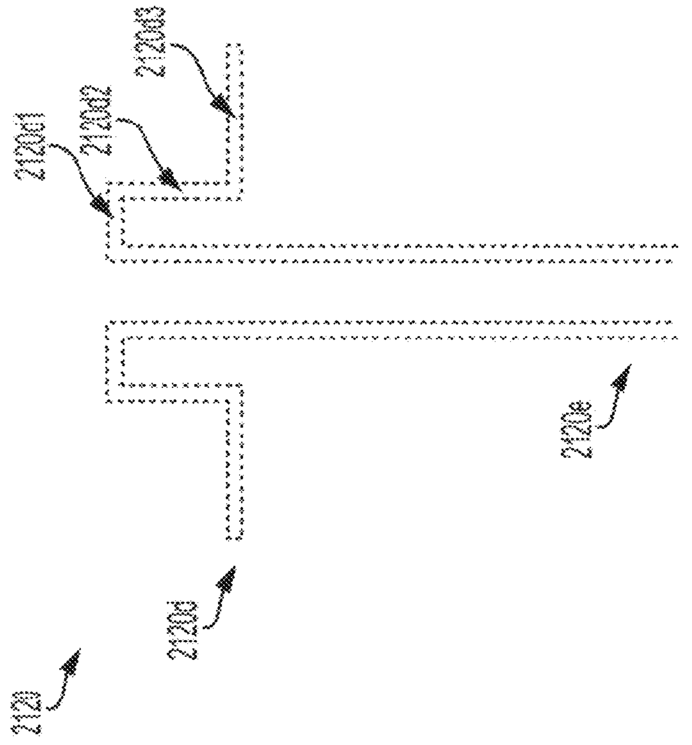

FIGS. 21A-21C depict various stages of an example method for contouring a mesh 2120 using the assembly 2000. The mesh 2120 may be a contoured mesh that was previously shape-set. For example, the dual-layered mesh 2120 shown in FIGS. 21A-21C has a shape similar to the shape of the mesh 1920 shown in FIG. 19C. The mesh 2120 comprises a closed end portion 2120*d* and an open end portion 2120*e* disposed at an angle to the closed end portion 2120*d*. In other examples, the assembly 2000 may be used to create a contoured mesh from a mesh with a shape (e.g., a tubular shape) different from the shape of mesh 2120 shown in FIGS. 21A-21C. As depicted in FIG. 21A, at least a portion of the open end portion 2120*e* of the mesh 2120 can be positioned within the lumen 2024 of the second member 2003 so that at least a portion of the closed end portion 2120*d* of the mesh 2120 is positioned over the protrusion 2022 of the second member 2003. As described herein, in some embodiments a mandrel 624 is positioned within a lumen of the mesh 2120 and/or the lumen 2024 of the second member 2003. Additionally or alternatively, one or more coupling elements may be coupled to the mesh 2120, as described herein. The one or more coupling elements may be coupled to the mesh 2120 before setting a shape of the mesh 2120, while setting a shape of the mesh 2120, or after setting a shape of the mesh 2120. The one or more coupling elements may be coupled to the mesh 2120 while the mesh 2120 conforms to the assembly 2000 and/or after the mesh 2120 has been removed from the assembly 2000.

As shown in FIG. 21B, the method may include causing the closed end portion 2120*d* of the mesh 2120 to substantially conform to the protrusion 2022 and/or the first surface 2014 of the second member 2003. For example, as shown in FIG. 21B, the method may include positioning the first member 2002 adjacent to the second member 2003 so that a first portion 2120*d*1 of the closed end portion 2120*d* of the mesh 2120 and at least a portion of the protrusion 2022 are received within the first portion 2012*a* of the lumen 2012 of the first member 2002. A second portion 2120*d*2 of the closed end portion 2120*d* of the mesh 2120 may substantially conform to a sidewall of the protrusion and a third portion 2120*d*3 of the closed end portion 2120*d* of the mesh 2120 may substantially conform to the first surface 2014 of the second member 2003 and the second surface 2006 of the first member 2002. As previously described, in some embodiments at least a portion of the mandrel 624 may be positioned within the lumen 2012. In some embodiments, the mesh 2120 is compressed between the first and second members 2002, 2003. The first and second members 2002, 2003 may be fixed in place prior to setting a shape of the mesh 2120. As described herein, setting a shape of the mesh 2120 may comprise subjecting the assembly 2000 and mesh 2120 to a heat treatment procedure.

FIG. 21C depicts the dual-layered, contoured mesh 2120 resulting from the method depicted in FIGS. 21A and 21B. The mesh 2120 has a closed end portion 2120*d* and an open end portion 2120*e* disposed at an angle to the closed end portion 2120*d*. The open end portion 2120*e* can have a substantially tubular configuration. In some embodiments, for example as shown in FIG. 21C, the closed end portion 2120*d* encloses an open volume that is substantially disc shaped with a protruding region formed by the first and second portions 2120*d*1, 2120*d*2 of the closed end portion 2120*d* of the mesh 2120. The protruding region may have a shape based on the shape of the protrusion 2022 of the second member 2003. For example, the protruding region may be substantially cylindrical when formed over a cylindrical protrusion 2022. The first portion 2120*d*1 of the closed end portion 2120*d* may be generally parallel to the third portion 2120*d*3 of the closed end portion 2120*d* of the mesh 2120. As shown in FIG. 21C, the first portion 2120*d*1 may be offset from the third portion 2120*d*3 by a length of the second portion 2120*d*2. The second portion 2120*d*2 may be substantially perpendicular to the first and third portions 2120*d*1, 2120*d*3.

Although the mesh 2120 shown in FIG. 21C depicts the first, second, and third portions 2120*d*1, 2120*d*2, 2120*d*3 extending along substantially straight paths, in some embodiments the first portion 2120*d*1, the second portion 2120*d*2, and/or the third portion 2120*d*3 of the closed end portion 2120*d* and/or the open end portion 2120*e* extend along curved paths (see FIG. 21D). Moreover, although FIG. 21C depicts the first and third portions 2120*d*1, 2120*d*3 disposed at an angle of about 90 degrees to the second portion 2120*d*2 and the first portion 2120*d*1 disposed at an angle of about 90 degrees of the closed end portion 2120*d* of the mesh 2120, in some embodiments the above-noted angles may be different than 90 degrees.

CONCLUSION

Although many of the embodiments are described above with respect to methods of manufacturing occlusive devices, the technology is applicable to other applications and/or other approaches. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-21D.

As used herein, the terms “generally,” “substantially,” “about,” and similar terms are used as terms of approximation and not as terms of degree, and are intended to account for the inherent variations in measured or calculated values that would be recognized by those of ordinary skill in the art. The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word “or” is expressly limited to mean only a single item exclusive from the other items in reference to a list of two or more items, then the use of “or” in such a list is to be interpreted as including (a) any single item in the list, (b) all of the items in the list, or (c) any combination of the items in the list. Additionally, the term “comprising” is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method for making an occlusive device, the method comprising:

obtaining a tubular mesh having a lumen extending therethrough and a porosity configured to substantially prevent blood flow through the mesh, the mesh comprising first and second end portions and an intermediate portion therebetween;

obtaining a forming assembly comprising:

a first member having a lumen extending therethrough, wherein the first member has a first mating surface comprising at least a portion of an outer surface of the first member; and a second member having a cavity with an arcuate surface, the second member having a lumen extending therethrough;

positioning at least a first portion of the intermediate portion of the mesh over an outer surface of the second member;

positioning at least a portion of the first end portion of the mesh within the lumen of the first member;

positioning at least a second portion of the intermediate portion of the mesh between the first mating surface of the first member and the arcuate surface of the second member such that the second portion substantially conforms to the first mating surface and the arcuate surface;

setting a shape of the mesh while the mesh is positioned on the forming assembly.

2. The method of claim 1, wherein positioning the second portion of the intermediate portion of the mesh between the first mating surface of the first member and the arcuate surface of the second member comprises positioning the first member at least partially within the cavity of the second member.

3. The method of claim 1, further comprising folding at least a portion of the intermediate portion of the mesh over the first member such that a third portion of the intermediate portion of the mesh conforms to a second mating surface comprising at least a portion of the outer surface of the first member.

4. The method of claim 1, wherein setting the shape of the mesh comprises heat-treating the mesh while the mesh is positioned on at least one member of the forming assembly.

5. The method of claim 1, further comprising positioning an elongate member within the lumen of the tubular mesh and the lumen of the second member.

6. The method of claim 5, further comprising, after positioning the elongate member within the lumen of the tubular mesh and the lumen of the second member, conforming the first and second end portions of the mesh to an outer surface of the elongate member.

7. The method of claim 1, wherein the mesh comprises a plurality of braided filaments.

8. The method of claim 1, further comprising coupling a coupling element to the first and second end portions of the mesh at a location adjacent to an outer surface of the second member.

9. The method of claim 1, further comprising:

obtaining a third member having a mating surface; and conforming the third portion of the intermediate portion of the mesh to the mating surface of the third member.

10. A method for making an occlusive device, the method comprising:

obtaining a tubular mesh having a first end portion, a second end portion opposite the first end portion along a length of the mesh, and an intermediate portion therebetween;

obtaining a first forming member having an outer surface and an inner surface spaced apart from the outer surface by a thickness of the first forming member, the inner surface defining an opening of the first forming member;

obtaining a second forming member having a mating surface with a shape at least partially corresponding to a shape of the inner surface of the first forming member;

positioning at least a first portion of the intermediate portion of the mesh over an outer surface of the second member;

positioning the second forming member within the opening of the first forming member such that a second portion of the intermediate portion of the mesh is positioned between and conforms to the inner surface of the first forming member and the mating surface of the second forming member;

folding the intermediate portion of the mesh over the first forming member such that a third portion of the intermediate portion of the mesh conforms to the outer surface of the first forming member; and setting a shape of the mesh while the mesh is positioned on the forming assembly.

11. The method of claim 10, wherein the first portion of the intermediate portion of the mesh conformed to the outer surface of the second forming member is separated from the third portion of the intermediate portion of the mesh conformed to the outer surface of the first forming member by the thickness of the first forming member.

12. The method of claim 10, wherein the second forming member includes a lumen extending therethrough.

13. The method of claim 10, wherein the thickness of the first forming member is nonuniform.

14. The method of claim 10, further comprising positioning an elongate member within the lumen of the tubular mesh and the lumen of the second member.

15. The method of claim 14, further comprising, after positioning the elongate member within the lumen of the tubular mesh and the lumen of the second member, conforming the first and second end portions of the mesh to an outer surface of the elongate member.

16. The method of claim 10, further comprising coupling a coupling element to the first and second end portions of the mesh at a location adjacent to an outer surface of the second member.

17. The method of claim 10, wherein setting the shape of the mesh comprises heat-treating the mesh while positioned on at least one of the first and second forming members.

18. The method of claim 10, wherein, after setting the shape of the mesh, the mesh comprises a contoured configuration in which the first and second end portions of the mesh have a substantially tubular shape and the intermediate portion of the mesh is substantially chalice-shaped.

19. The method of claim 10, wherein the mesh comprises a plurality of braided filaments.

20. The method of claim 10, wherein the mesh comprises a resilient and/or superelastic material.

* * * * *